(12) United States Patent
Schweighoffer et al.

(10) Patent No.: US 8,003,375 B2
(45) Date of Patent: *Aug. 23, 2011

(54) QUALITATIVE DIFFERENTIAL SCREENING

(75) Inventors: Fabien Schweighoffer, Vincennes (FR);
Laurent Bracco, Paris (FR); Bruno Tocque, Courbevoie (FR)

(73) Assignee: ExonHit Therapeutics S.A., Paris (FR)

( * ) Notice: Subject to any disclaimer, the term of this patent is extended or adjusted under 35 U.S.C. 154(b) by 0 days.

This patent is subject to a terminal disclaimer.

(21) Appl. No.: 12/622,364

(22) Filed: Nov. 19, 2009

(65) Prior Publication Data

US 2010/0144550 A1   Jun. 10, 2010

Related U.S. Application Data

(63) Continuation of application No. 10/833,440, filed on Apr. 28, 2004, now abandoned, which is a continuation of application No. 09/623,828, filed as application No. PCT/FR99/00547 on Mar. 11, 1999, now Pat. No. 6,881,571, and a continuation-in-part of application No. 09/046,920, filed on Mar. 24, 1998, now Pat. No. 6,251,590.

(30) Foreign Application Priority Data

Mar. 11, 1998  (FR) ...................................... 98 02997

(51) Int. Cl.
*C07H 21/04* (2006.01)
*C12Q 1/68* (2006.01)
*C12M 1/34* (2006.01)

(52) U.S. Cl. ...................... 435/287.2; 435/6.1; 435/91.1; 435/91.2; 536/23.1; 536/22.1; 536/24.3; 536/24.31; 536/24.32; 536/24.33

(58) Field of Classification Search ......................... None
See application file for complete search history.

(56) References Cited

U.S. PATENT DOCUMENTS 4,888,278 A   12/1989   Singer et al.
4,965,188 A   10/1990   Mullis et al.

(Continued)

FOREIGN PATENT DOCUMENTS

EP   0 330 781   9/1989

(Continued)

OTHER PUBLICATIONS

Kusiak et al. (Mol. Brain Research, vol. 20, pp. 64-70, 1993).*

(Continued)

*Primary Examiner* — Jeanine A Goldberg
(74) *Attorney, Agent, or Firm* — Clark & Elbing LLP

(57) ABSTRACT

The invention concerns a method for identifying and/or cloning nucleic acid regions representing qualitative differences associated with alternative splicing events and/or with insertions, deletions located in RNA transcribed genome regions, between two physiological situations, comprising either hybridization of RNA derived from the test situation with cDNA's derived from the reference situation and/or reciprocally, or double-strand hybridization of cDNA derived from the test situation with cDNA's derived from the reference situation; and identifying and/or cloning nucleic acids representing qualitative differences. The invention also concerns compositions or banks of nucleic acids representing qualitative differences between two physiological situations, obtainable by the above method, and their use as probe, for identifying genes or molecules of interest, or still for example in methods of pharmacogenomics, and profiling of molecules relative to their therapeutic and/or toxic effects. The invention further concerns the use of dysregulation of splicing RNA as markers for predicting molecule toxicity and/or efficacy, and as markers in pharmacogenomics.

24 Claims, 26 Drawing Sheets

U.S. PATENT DOCUMENTS

Figure 1A:
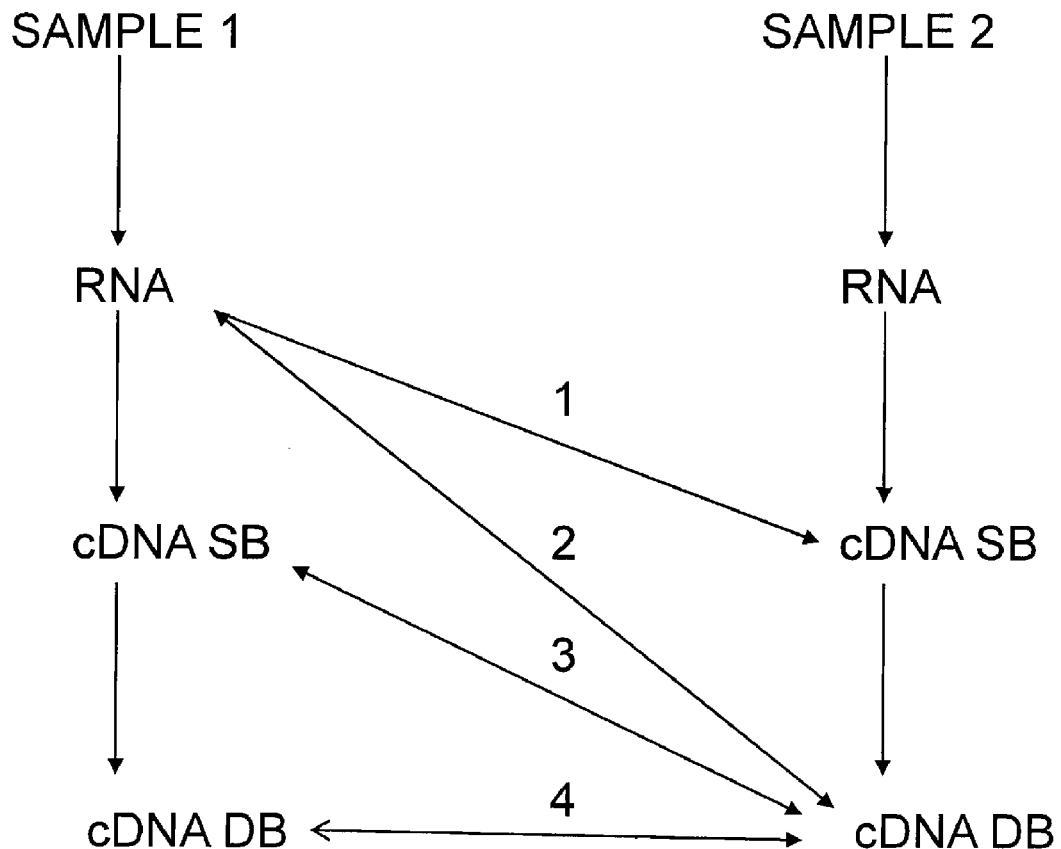

| | | | |
|---|---|---|---|
| 5,057,410 | A | 10/1991 | Kawasaki et al. |
| 5,143,854 | A | 9/1992 | Pirrung et al. |
| 5,215,882 | A | 6/1993 | Bahl et al. |
| 5,445,934 | A | 8/1995 | Fodor et al. |
| 5,474,796 | A * | 12/1995 | Brennan ............... 427/2.13 |
| 5,484,702 | A | 1/1996 | Ludwig |
| 5,521,297 | A | 5/1996 | Daggett et al. |
| 5,643,729 | A | 7/1997 | Taniguchi et al. |
| 5,674,682 | A | 10/1997 | Croce et al. |
| 5,679,541 | A | 10/1997 | Bonini et al. |
| 5,770,421 | A | 6/1998 | Morris et al. |
| 5,807,522 | A | 9/1998 | Brown et al. |
| 5,830,645 | A | 11/1998 | Pinkel et al. |
| 5,837,832 | A | 11/1998 | Chee et al. |
| 5,858,671 | A | 1/1999 | Jones |
| 5,908,920 | A | 6/1999 | Sidransky |
| 5,922,535 | A | 7/1999 | Huo |
| 5,985,549 | A | 11/1999 | Singer et al. |
| 6,027,889 | A | 2/2000 | Barany et al. |
| 6,060,240 | A | 5/2000 | Kamb et al. |
| 6,083,697 | A | 7/2000 | Beecher et al. |
| 6,107,088 | A | 8/2000 | Korneluk et al. |
| 6,160,105 | A | 12/2000 | Cunningham et al. |
| 6,168,920 | B1 | 1/2001 | Hillman et al. |
| 6,251,590 | B1 | 6/2001 | Schweighoffer et al. |
| 6,268,170 | B1 | 7/2001 | Siddique et al. |
| 6,303,301 | B1 | 10/2001 | Mack |
| 6,309,822 | B1 | 10/2001 | Fodor et al. |
| 6,334,316 | B1 | 1/2002 | Maeda et al. |
| 6,344,316 | B1 | 2/2002 | Lockhart et al. |
| 6,368,794 | B1 | 4/2002 | Daniel et al. |
| 6,368,799 | B1 | 4/2002 | Chee |
| 6,372,432 | B1 | 4/2002 | Tocque et al. |
| 6,475,789 | B1 | 11/2002 | Cech et al. |
| 6,509,153 | B1 | 1/2003 | Tocque et al. |
| 6,617,110 | B1 | 9/2003 | Cech et al. |
| 6,625,545 | B1 | 9/2003 | Amitai et al. |
| 6,699,659 | B2 | 3/2004 | Webster |
| 6,713,257 | B2 | 3/2004 | Shoemaker et al. |
| 6,849,400 | B1 | 2/2005 | Harvey et al. |
| 6,881,571 | B1 * | 4/2005 | Schweighoffer et al. .. 435/287.2 |
| 6,951,924 | B2 | 10/2005 | Rosen et al. |
| 6,974,666 | B1 * | 12/2005 | Lockhart et al. ............... 435/6 |
| 7,833,779 | B2 | 11/2010 | Srinivasan et al. |
| 2002/0119455 | A1 | 8/2002 | Chan |
| 2003/0059788 | A1 | 3/2003 | Tocque et al. |
| 2003/0092033 | A1 | 5/2003 | Weiner et al. |
| 2003/0165931 | A1 | 9/2003 | Tocque et al. |
| 2004/0191828 | A1 | 9/2004 | Schweighoffer et al. |
| 2007/0042400 | A1 | 2/2007 | Choi et al. |

FOREIGN PATENT DOCUMENTS

| | | |
|---|---|---|
| EP | 0 709 397 | 5/1996 |
| EP | 0 791 660 | 8/1997 |
| EP | 0 806 478 | 11/1997 |
| FR | 2 664 287 | 1/1992 |
| FR | 2 775 984 | 3/1998 |
| WO | WO 89/10977 | 11/1989 |
| WO | WO 94/12631 | 6/1994 |
| WO | WO 95/27052 | 10/1995 |
| WO | WO 96/26272 | 8/1996 |
| WO | WO 96/30512 | 10/1996 |
| WO | WO 97/04092 | 2/1997 |
| WO | WO 97/10365 | 3/1997 |
| WO | WO 97/13877 | 4/1997 |
| WO | WO 97/27317 | 7/1997 |
| WO | WO 97/29212 | 8/1997 |
| WO | WO 97/46679 | 12/1997 |
| WO | WO 98/02576 | 1/1998 |
| WO | WO 99/10529 | 3/1999 |
| WO | WO 99/42606 | 8/1999 |
| WO | WO 99/46403 | 9/1999 |
| WO | WO 00/12760 | 3/2000 |

OTHER PUBLICATIONS

Virts et al. (Molecular Immunology, vol. 35, pp. 167-176, 1998).*
Rice et al. (Gynecologic Oncology, vol. 65, pp. 149-157, 1997).*
Chee et al. (Science, vol. 274, pp. 610-614, Oct. 1996).*
Zhu et al. (Int. J. Cancer, vol. 72, pp. 574-580, 1997).*
Baldi et al., "Genomic Structure of the Human Retinoblastoma-Related Rb2/p130 Gene," *Proc. Natl. Acad. Sci. USA* 93:4629-4632, 1996.
Di Segni et al., "Cis- and Trans-Splicing of mRNAs Mediated by tRNA Sequences in Eukaryotic Cells," *Proc. Natl. Acad. Sci. USA* 105:6864-6869, 2008.
Famiglietti et al., "Tyrosine Residue in Exon 14 of the Cytoplasmic Domain of Platelet Endothelial Cell Adhesion Molecule-1 (PECAM-1/CD31) Regulates Ligand Binding Specificity," *Journal of Cell Biology* 138:1425-1435, 1997.
Hacia et al., "Enhanced High Density Oligonucleotide Array-Based Sequence Analysis Using Modified Nucleoside Triphosphates," *Nucleic Acids Res.* 26: 4975-4982, 1998.
Le Fur et al., "Selective Increase in Specific Alternative Splice Variants of Tyrosinase in Murine Melanomas: A Projected Basis for Immunotherapy, "*Proc. Natl. Acad. Sci. USA* 94:5332-5337, 1997.
Lockhart et al., "Genomics, Gene Expression and DNA Arrays," *Nature* 405:827-836, 2000.
Norgren et al., "Regulation of Human Insulin Receptor RNA Splicing in Hepg2 Cells: Effects of Glucocorticoid and Low Glucose Concentration," *Biochemical and Biophysical Research Communications* 199:277-284, 1994.
Pelicci et al., "A Novel Transforming Protein (SHC) with an SH2 Domain is Implicated in Mitogenic Signal Transduction," *Cell* 70:93-104, 1992.
Perret et al., "Improved Differential Screening Approach to Analyse Transcriptional Variations in Organized cDNA Libraries," *Gene* 208:103-115, 1998.
Romani et al., Detection and Analysis of Spliced Chimeric mRNAs in Sequence Databanks, *Nucleic Acids Research* 31:e17, 2003.
Shapiro et al., "Multiple Mechanisms of p16$^{INK4A}$ Inactivation in Non-Small Lung Cancer Cell Lines," *Cancer Research* 55:6200-6209, 1995.
Virts et al., "Expression of CD45 isoforms lacking exons 7, 8 and 10," Mol. Immunol. 35:167-176, 1998.
Alnemri, et al., "Cloning and Expression of Four Novel Isoforms of Human Interleukin-1β Converting Enzyme with Different Apoptotic Activities," *J. Biol. Chem.* 270:4312-4317, 1995.
Alon et al., "Broad Patterns of Gene Expression Revealed by Clustering Analysis of Tumor and Normal Colon Tissues Probed by Oligionucleotide Arrays," *Proc. Natl. Acad. Sci. USA* 96:6745-6750, 1999.
Alphey, "PCR-Based Method for Isolation of Full-Length Clones and Splice Variants from cDNA Libraries," *BioTechniques* 22: 481-482 and 485-486, 1997.
Ambartsumian et al., "Characterization of Two Splice Variants of Metastasis-Associated Human *mts1*Gene," *Gene* 159:125-130, 1995.
Ardley et al., "Rapid Isolation of Genomic Clones for Individual Members of Human Multigene Families: Identification and Localisation of UBE2L4, A Novel Member of a Ubiquitin Conjugating Enzyme Dispersed Gene Family," *Cytogenet. Cell Genet.* 79:188-192, 1997.
Black, "Protein Diversity From Alternative Splicing: A Challenge for Bioinformatics and Post-Genome Biology," *Cell* 103:367-370, 2000.
Bloom et al., "Identification and Tissue-Specific Expression of PDE7 Phosphodiesterase Splice Variants," *Proc. Natl. Acad. Sci. USA* 93:14188-14192, 1996.
Bonass et al., "The Rat Amelogenin Gene—Some Aspects of Evolution and Expression," *Adv. Dent. Res.* 10:182-186, 1996.
Canton et al., "Identification, Molecular Cloning, and Distribution of a Short Variant of the 5-Hydroxytryptamine$_{2C}$ Receptor Produced by Alternative Splicing," *Mol. Pharmacol.* 50:799-807, 1996.
Chee et al., "Accessing Genetic Information with High-Density DNA Arrays," *Science* 274:610-614, 1996.
Cheng et al., "Protection from Fat-Mediated Apoptosis by a Soluble Form of the Fat Molecule," *Science* 263:1759-1762, 1994.
Cichon et al., "Pharmacogenetics of Schizophrenia," *Am. J. Med. Genet.* 97:98-106, 2000.

Cooper et al., "Gene Therapy Advances: Utilization of Alternative Splicing as a Control Element in the Chimeric-Enzyme/Prodrug Therapy (cept) Approach to Primary and Metastatic Tumors," *J. Clin. Ligand Assay* 19:80-84, 1996.

Diatchenko et al., "Suppression Subtractive Hybridization: A Method for Generating Differentially Regulated or Tissue-Specific cDNA Probes and Libraries," *Proc. Natl. Acad. Sci. USA* 93:6025-6030, 1996.

Drmanac et al., "Gene-Representing cDNA Clusters Defined by Hybridization of 57,419 Clones from Infant Brain Libraries with Short Oligonucleotide Probes," *Genomics* 37:29-40, 1996.

Fong et al., "Epidermal Growth Factor Induces Gadd45 (Growth Arrest and DNA Damage Inducible Protein) Expression in A431 Cells," *Biochem. Biophys. Acta.* 1517:250-256, 2001.

Gelfand et al., "ASDB: Database of Alternatively Spliced Genes," *Nucleic Acids Res.* 27: 301-302, 1999.

Ion et al., "A Novel Mutation in the Putative DNA Helicase *XH2* is Responsible for Male-to-Female Sex Reversal Associated with an Atypical Form of the ATR-X Syndrome," *Am. J. Hum. Genet* 58:1185-1191, 1996.

Komarova et al., "Stress-Induced Secretion of Growth Inhibitors: A Novel Tumor Suppressor Function of p53," *Oncogene* 17:1089-1096, 2003.

Kusiak et al., "A Splice Variant of the N-Methyl-D-Aspartate (NMDAR1) Receptor," *Molecular Brain Research* 20:64-70, 1993.

Lisitsyn et al., "Comparative Genomic Analysis of Tumors: Detection of DNA Losses and Amplification," *Proc. Natl. Acad. Sci. USA* 92:151-155, 1995.

Lorson et al., "A Single Nucleotide in the *SMN* Gene Regulates Splicing and is Responsible for Spinal Muscular Atrophy," *Proc. Natl. Acad. Sci. USA* 96:6307-6311, 1999.

Miller et al., "Improved Phenol Emulsion DNA Reassociation Technique (PERT) Using Thermal Cycling," *Nucleic Acids Res.* 23:2339-2340, 1995.

Morgan et al., "Three Splicing Patterns Are Used to Excise the Small Intron Common to all Minute Virus of Mice RNAs," *J. Virol.* 60:1170-1174, 1986.

Nakajima et al., "A New Alternative Splice Variant of the Mouse FAS Antigen with a Deletion in the N-Terminal Portion of the Extracellular Domain," *Life Sci.* 58:761-768, 1996.

Prashar et al., "Analysis of Differential Gene Expression by Display of 3' End Restriction Fragments of cDNAs," *Proc. Natl. Acad. Sci. USA* 93:659-663, 1996.

Raben, "A Model of mRNA Splicing in Adult Lysosomal Storage Disease (Glycogenosis Type II)," *Hum. Mol. Genet.* 5:995-1000, 1996.

Rice et al., "Estrogen Receptor mRNA Splice Variants in Pre- and Postmenopausal Human Endometrium and Endometrial Carcinoma," *Gynecol. Oncol.* 65:149-157, 1997.

Roemer et al., "p53 Transactivation Domain Mutant Q22, S23 is Impaired for Repression of Promoters and Mediation of Apoptosis," *Oncogene* 12:2069-2079, 1996.

Roth et al., "Retrovirus-Mediated Wild-Type p53 Gene Transfer to Tumors of Patients with Lung Cancer," *Nat. Med.* 2:985-991, 1996.

Sabbatini et al., "Essential Role for p53-Mediated Transcription in E1A-Induced Apoptosis," *Genes Dev.* 9:2184-2192, 1995.

Schena et al., "Parallel Human Genome Analysis: Microarray-Based Expression Monitoring of 1000 Genes," *Proc. Natl. Acad. Sci. USA* 93:10614-10619, 1996.

Spilsbury et al., "Isolation of a Novel Macrophage-Specific Gene by Differential cDNA Analysis," *Blood* 85:1620-1629, 1995.

Sugai et al., "Isolation of Differentially Expressed Genes Upon Immunoglobulin Class Switching by a Subtractive Hybridization Method Using Uracil DNA Glycosylase," *Nucleic Acids Research* 26(4):911-918, 1998.

Tröster et al., "One Gene, Two Transcripts; Isolation of an Alternative Transcript Encoding for the Autoantigen La/SS-B from a cDNA Library of a Patient with Primary Sjögrens' Syndrome," *J. Exp. Med.* 180:2059-2067, 1994.

Varesco et al., "Mutation in a Splice-Donor Site of the APC Gene in a Family with Polyposis and Late Age of Colonic Cancer Death," *Hum. Genet.* 93:281-286, 1994.

von Stein et al., "A High Throughput Screening for Rarely Transcribed Differentially Expressed Genes," *Nuc. Acids Res.* 25:2598-2602, 1997.

Wang et al., "Identification of the Genes Responsive to Etoposide-Induced Apoptosis: Application of DNA Chip Technology," *FEBS Lett.* 445:269-273, 1999.

Wang et al., "Systematic Screening for RNA with Skipped Exons—Splicing Mutations of the Ferrochelatase Gene," *Biochim. Biophys. Acta* 1271:358-362, 1995.

Watanabe et al., "Splicing Isoforms of Rat Ash/Grb2," *Biol. Chem.* 270:13733-13739, 1995.

Zhang et al., "Reconstruction of DNA Sequencing by Hybridization," *Bioinformatics* 19:14-21, 2003.

Zhao et al., "High-Density cDNA Filter Analysis: A Novel Approach for Large-Scale, Quantitative Analysis of Gene Expression," *Gene,* 156:207-213, 1995.

Zhu et al., "Deletion within the Src Homology Doman 3 of Bruton's Tyrosine Kinase Resulting in X-linked Agammaglobulinemia (XLA)," J. Exp. Med. 180:461-470, 1994.

Zhu et al., "Identification of an Exon 3 Deletion Splice Variant Androgen Receptor mRNA in Human Breast Cancer," *Int. J. Cancer* 72:574-580, 1997.

\* cited by examiner path. RNA/normal cDNA hybrids
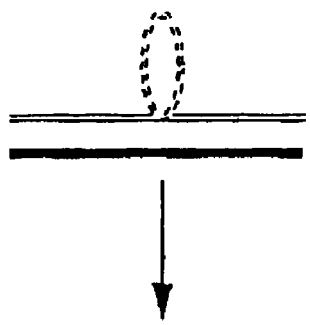
non spliced sequences after RNase H digestion
desired sequence which is 5'- and 3'-labelled by two oligonucleotides
PCR-amplified fragment
cloning and sequencing
FIGURE 3

Figure 8
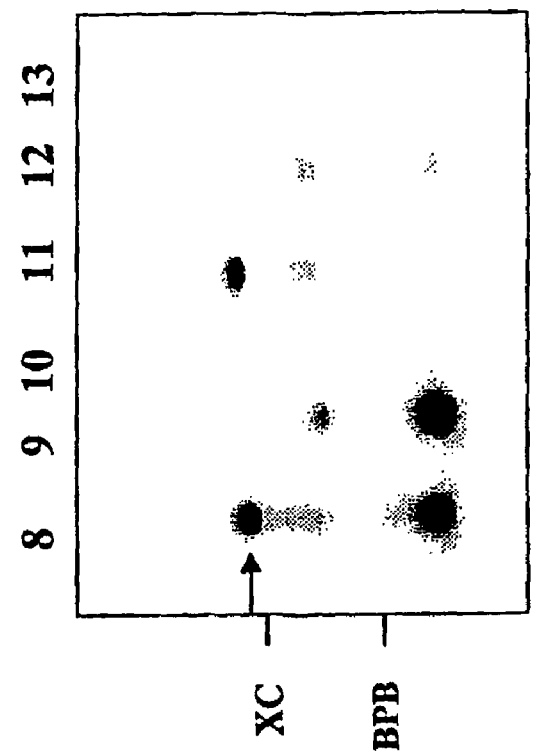
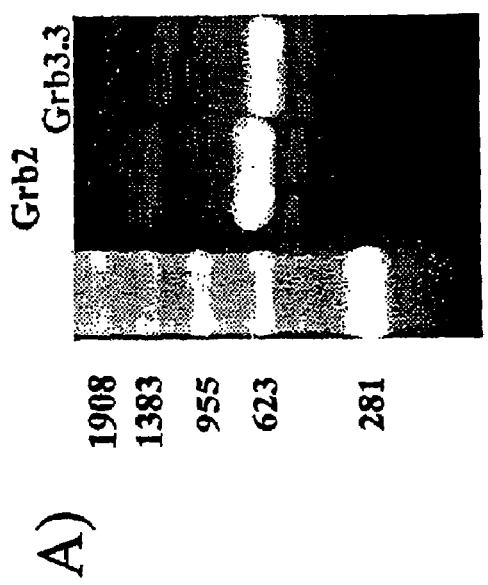
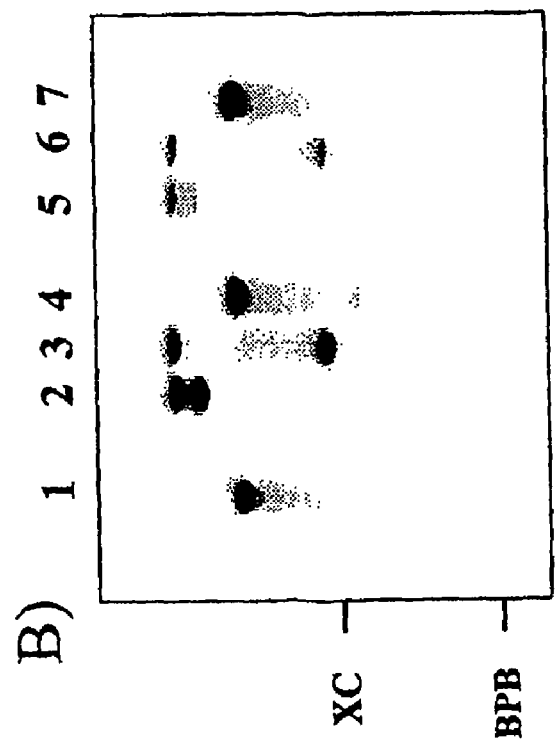

A)
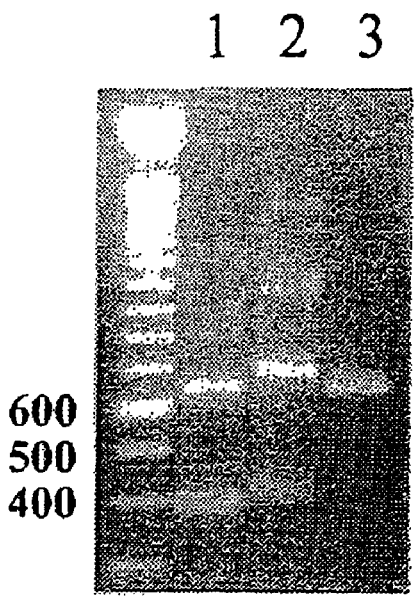
B)
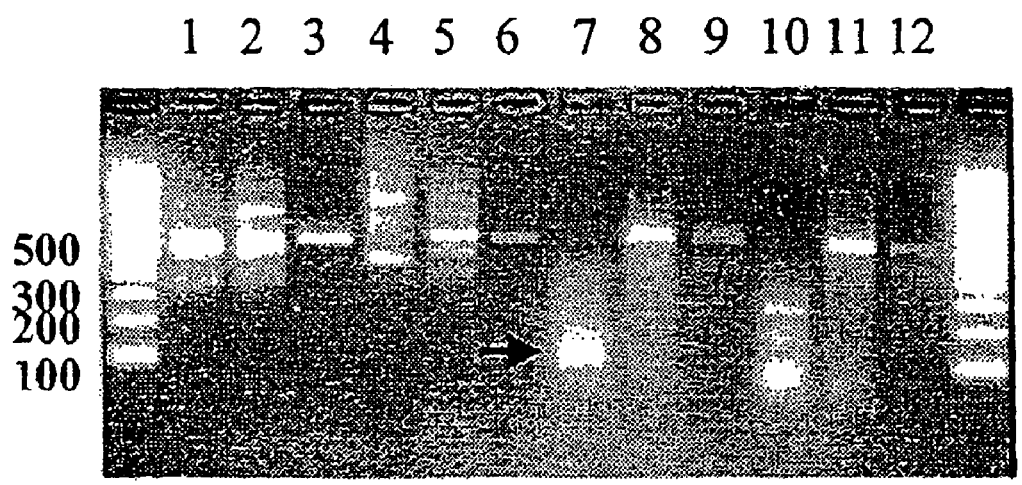
Figure 11

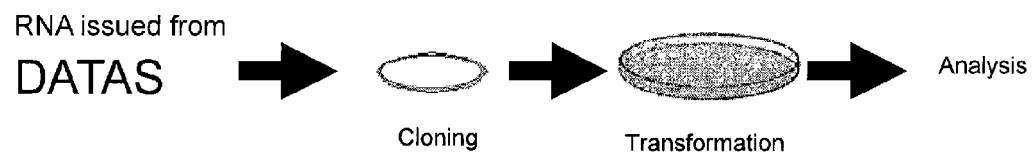
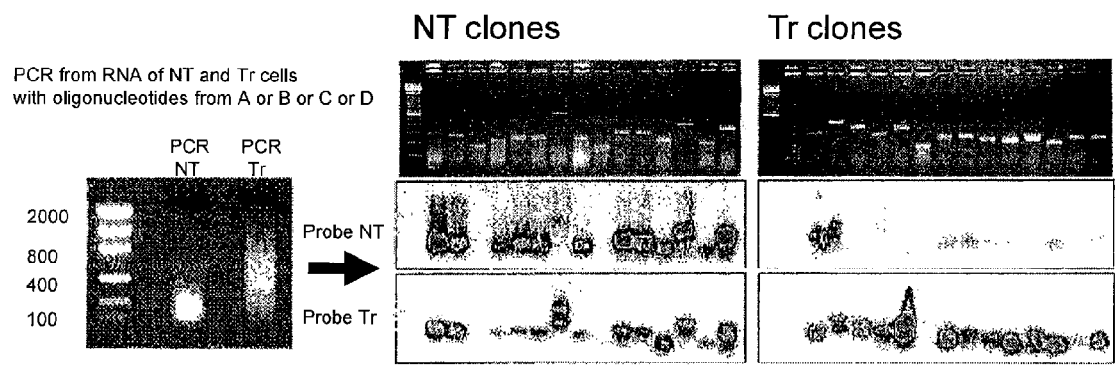
FIGURE 12

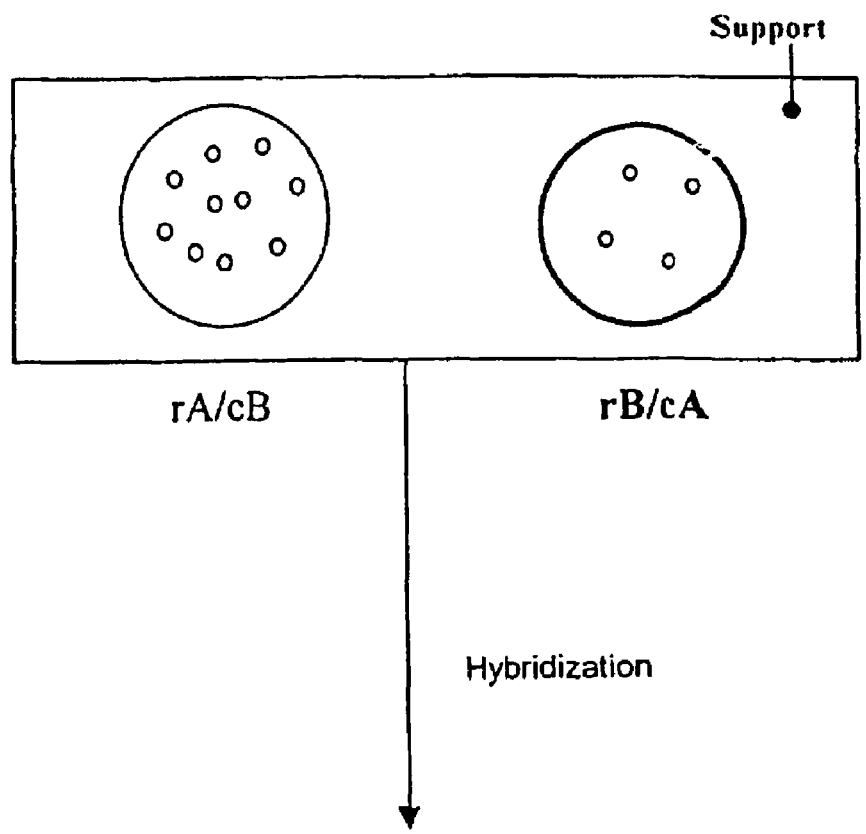
rA/cB    rB/cA
Hybridization
responder-derived biopsy samples
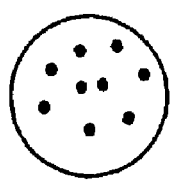    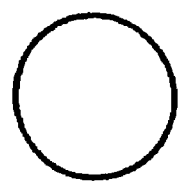
unresponder-derived biopsy samples
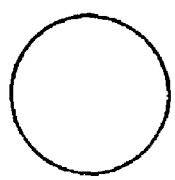    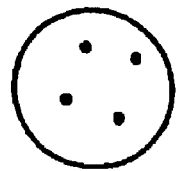
FIGURE 15

Peptidic Sequence of ΔSHC (SEQ ID NO: 9)

```
1
MNKLSGGGGR  RTRVEGGQLG  GEEWTRHGSF  VNKPTRGWLH  PNDKVMGPGV
SYLVRYMGCV  EVLQSMRALD  FNTRTQVTRE  AISLVCEAVP  GAKGATRRRK
PCSRPLSSIL  GRSNLKFAGM  PITLTVSTSS  LNLMAADCKQ  IIANHHMQSI
SFASGGDPDT  AEYVAYVAKD  PVNQRACHIL  ECPEGLAQDV  ISTIGQAFEL
RFKQYLRNPP  KLVTPHDRMA  GFDGSAWDEE  EEEPPDHQYY  NDFPGKEPPL
GGVVDMRLRE  GAAPGAARPT  APNAQTPSHL  GATLPVGQPV  GGDPEVRKQM
PPPPPCPGRE  LFDDPSYVNV  QNLDKARQAV  GGAGPPNPAI  NGSAPRDLFD
MKPFEDALRV  PPPPQSVSMA  EQLRGEPWFH  GKLSRREAEA  LLQLNGDFLV
RTKDHRFESV  SHLISYHMDN  HLPIISAGSE  LCLQQPVERKL
                                                    441
```

Nucleic Sequence of ΔSHC (SEQ ID NO: 10)

```
atgaacaagc  tgagtggagg  cggcgggcgc  aggactcggg  tggaagggggg   50
ccagcttggg  ggcgaggagt  ggacccgcca  cgggagcttt  gtcaataagc   100
ccacgcgggg  ctggctgcat  cccaacgaca  aagtcatggg  acccggggtt   150
tcctacttgg  ttcggtacat  gggttgtgtg  gaggtcctcc  agtcaatgcg   200
tgccctggac  ttcaacaccc  ggactcaggt  caccagggag  gccatcagtc   250
tggtgtgtga  ggctgtgccg  ggtgctaagg  gggcgacaag  gaggagaaag   300
ccctgtagcc  gcccgctcag  ctctatcctg  ggggaggagta  acctgaaatt   350
tgctggaatg  ccaatcactc  tcaccgtctc  caccagcagc  ctcaacctca   400
tggccgcaga  ctgcaaacag  atcatcgcca  accaccacat  gcaatctatc   450
tcatttgcat  ccggcgggga  tccggacaca  gccgagtatg  tcgcctatgt   500
tgccaaagac  cctgtgaatc  agagagcctg  ccacattctg  gagtgtcccg   550
aagggcttgc  ccaggatgtc  atcagcacca  ttggccaggc  cttcgagttg   600
cgcttcaaac  aatacctcag  gaacccaccc  aaactggtca  cccctcatga   650
caggatggct  ggctttgatg  gctcagcatg  ggatgaggag  gaggaagagc   700
cacctgacca  tcagtactat  aatgacttcc  cggggaagga  accccccttg   750
gggggggtgg  tagacatgag  gcttcgggaa  ggagccgctc  cagggctgc    800
tcgacccact  gcacccaatg  cccagacccc  cagccacttg  ggagctacat   850
tgcctgtagg  acagcctgtt  ggggggagatc  cagaagtccg  caaacagatg   900
```

FIGURE 17A

```
ccacctccac caccctgtcc aggcagagag cttttttgatg atccctccta  950
tgtcaacgtc cagaacctag acaaggcccg gcaagcagtg ggtggtgctg 1000
ggccccccaa tcctgctatc aatggcagtg caccccggga cctgtttgac 1050
atgaagccct tcgaagatgc tcttcgggtg cctccacctc cccagtcggt 1100
gtccatggct gagcagctcc gaggggagcc ctggttccat gggaagctga 1150
gccggcggga ggctgaggca ctgctgcagc tcaatgggga cttcttggtt 1200
cggactaagg atcaccgctt tgaaagtgtc agtcacctta tcagctacca 1250
catggacaat cacttgccca tcatctctgc gggcagcgaa ctgtgtctac 1300
agcaacctgt ggagcggaaa ctgtga                           1326
```

FIGURE 17B

Figure 18A:
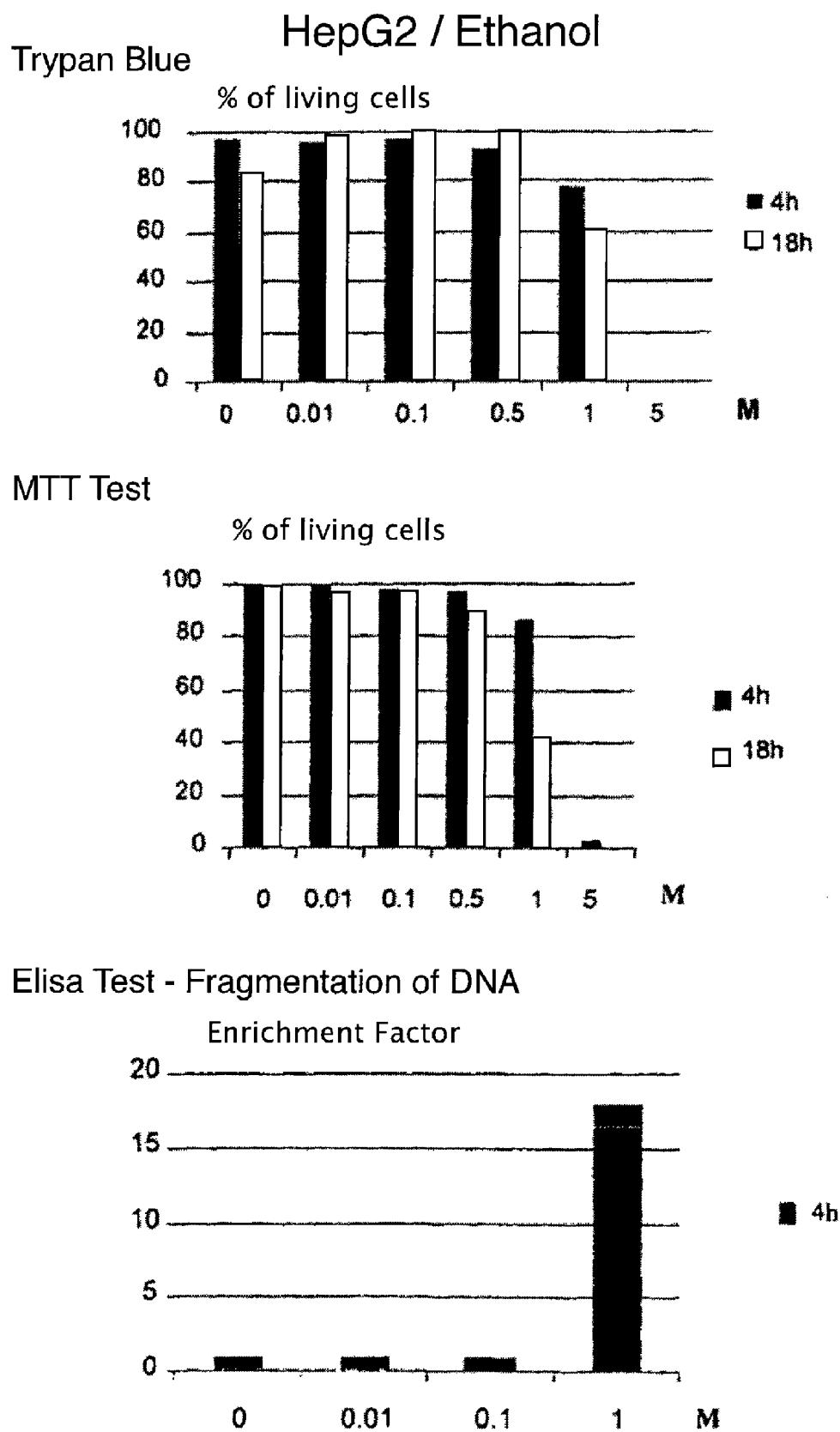

Trypan Blue
HepG2 / Camptothecin
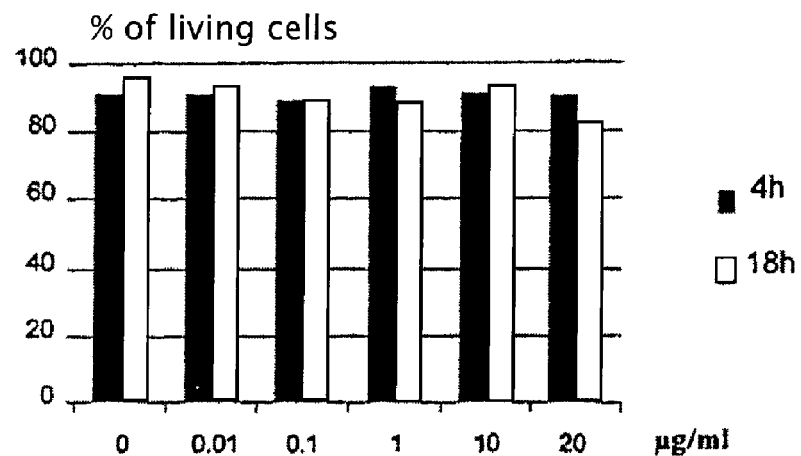
MTT Test
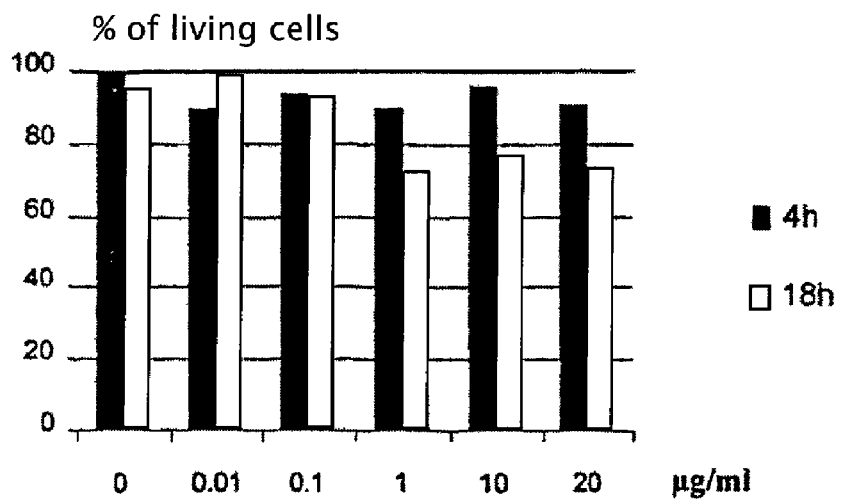
Elisa Test - Fragmentation of DNA
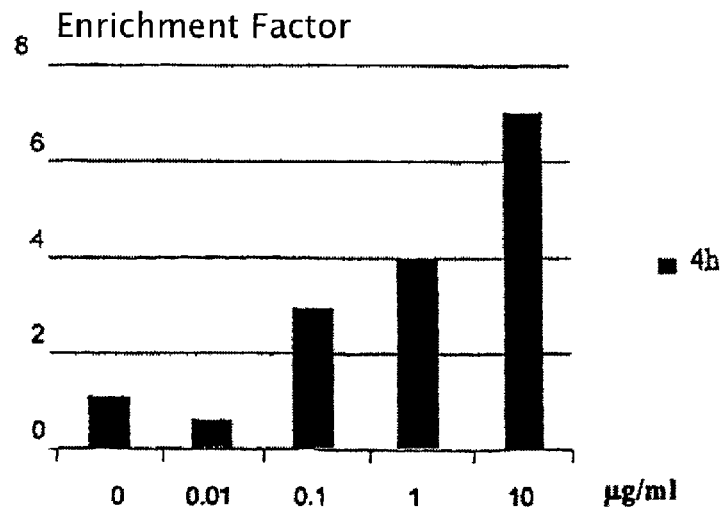
FIGURE 18B

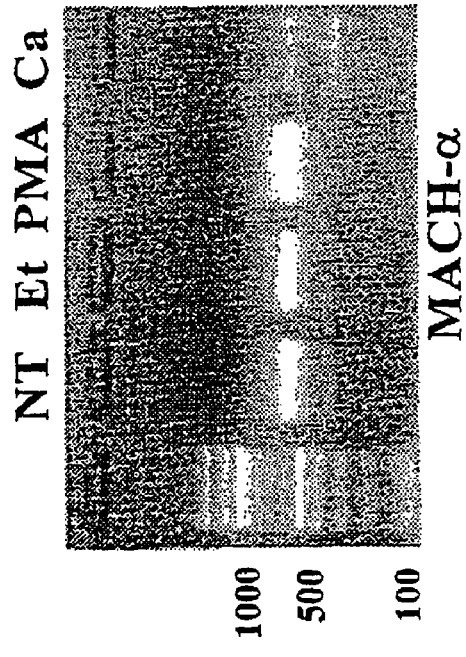
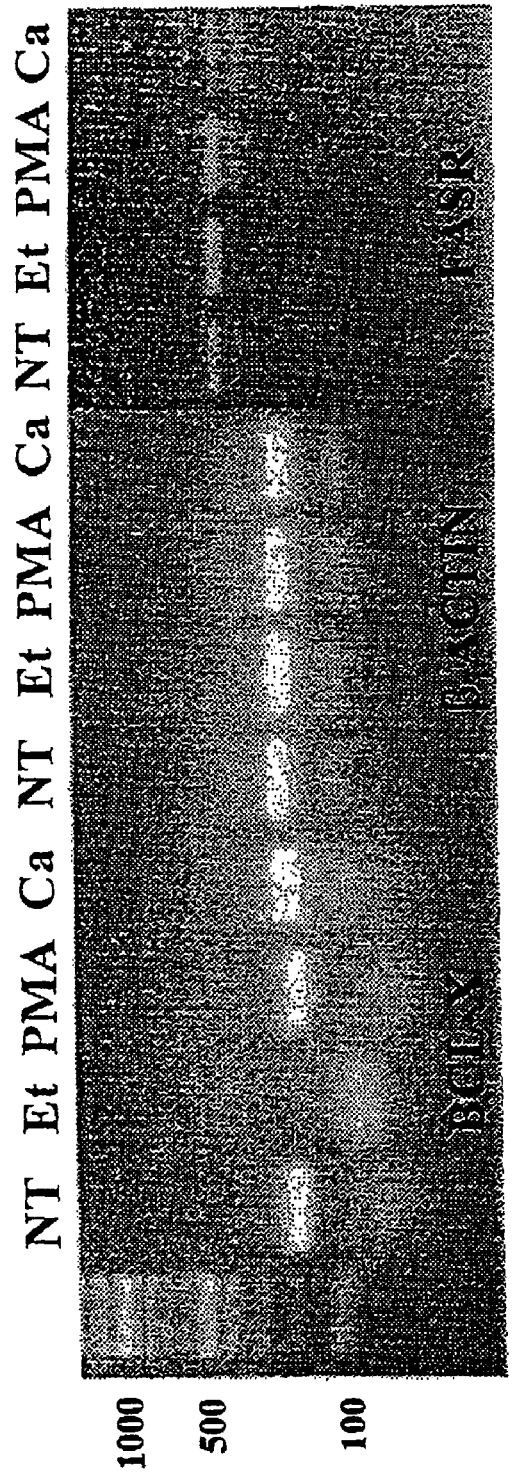
Figure 19

QUALITATIVE DIFFERENTIAL SCREENING

CROSS-REFERENCE TO RELATED APPLICATIONS

This application is a continuation of U.S. Ser. No. 10/833,440, filed Apr. 28, 2004, which is a continuation of U.S. Ser. No. 09/623,828, filed Sep. 8, 2000, which is a U.S. National Phase Application of PCT/FR99/00547, filed Mar. 11, 1999, and a continuation-in-part of U.S. Ser. No. 09/046,920, filed Mar. 24, 1998. This application also claims priority from French Patent Application No. 98 02997, filed Mar. 11, 1998. Each of these application is incorporated by reference herein in their entirety.

The present invention relates to the fields of biotechnology medicine, biology and biochemistry. Applications thereof are aimed at human health, animal and plant care. More particularly, the invention makes it possible to identify nucleic acid sequences whereby both novel screening methods for identifying molecules of therapeutic interest and novel gene therapy tools can be developed, and it further provides information on the toxicity and potency of molecules, as well as pharmacogenomic data.

The present invention primarily describes a set of original methods for identifying nucleic acid sequences which rely on demonstrating qualitative differences between RNAs derived from two distinct states being compared, in particular those derived from a diseased organ or tissue and healthy equivalents thereof. More specifically, these methods are intended to specifically clone alternative exons and introns which are differentially spliced with respect to a pathological condition and a healthy state or with respect to two physiological conditions one wishes to compare. These qualitative differences in RNAs can also be due to genome alterations such as insertions or deletions in the regions to be transcribed to RNA. This set of methods is identified by the acronym DATAS: Differential Analysis of Transcripts with Alternative Splicing.

The characterization of gene expression alterations which underlie or are linked to a given disorder raises substantial hope regarding the discovery of novel therapeutic targets and of original diagnostic tools. However, the identification of a genomic or complementary DNA sequence, whether through positional cloning or quantitative differential screening techniques, yields little, if any, information on the function, and even less on the functional domains, involved in the regulation defects related to the disease under study. The present invention describes a set of original methods aimed at identifying differences in RNA splicing occurring between two distinct pathophysiological conditions. Identifying such differences provides information on qualitative but not on quantitative differences as has been the case for techniques described so far. The techniques disclosed in the present invention are hence all encompassed under the term of "qualitative differential screening", or DATAS. The methods of the invention may be used to identify novel targets or therapeutic products, to devise genetic research and/or diagnostic tools, to construct nucleic acid libraries, and to develop methods for determining the toxicological profile or potency of a compound for example.

A first object of the invention is based more particularly on a method for identifying and/or cloning nucleic acid regions which correspond to qualitative genetic differences occurring between two biological samples, comprising hybridizing a population of double stranded cDNAs or RNAs derived from a first biological sample, with a population of cDNAs derived from a second biological sample (FIG. 1A).

As indicated hereinabove, the qualitative genetic differences may be due to alterations of RNA splicing or to deletions and/or insertions in the regions of the genome which are transcribed to RNA.

In a first embodiment, the hybridization is carried out between RNAs derived from a first biological sample and cDNAs (single stranded or double stranded) derived from a second biological sample.

In another embodiment, the hybridization is carried out between double stranded cDNAs derived from a first biological sample, and cDNAs (double stranded or, preferably, single stranded) derived from a second biological sample.

A more specific object of the invention is to provide a method for identifying differentially spliced nucleic acid regions occurring between two physiological conditions, comprising hybridizing a population of RNAs or double stranded cDNAs derived from a test condition with a population of cDNAs originating from a reference condition and identifying nucleic acids which correspond to differential splicing events.

Another object of the invention is to provide a method for cloning differentially spliced nucleic acids occurring between two physiological conditions, comprising hybridizing a population of RNAs or double stranded cDNAs derived from the test condition with a population of cDNAs originating from the reference condition and cloning nucleic acids which correspond to differential splicing events.

In a particular embodiment, the method of nucleic acid identification and/or cloning according to the invention comprises running two hybridizations in parallel consisting of:

(a) hybridizing RNAs derived from the first sample (test condition) with cDNAs derived from the second sample (reference condition);

(b) hybridizing RNAs derived from the second sample (reference condition) with cDNAs derived from the first sample (test condition); and (c) identifying and/or cloning, from the hybrids formed in steps (a) and (b), those nucleic acids corresponding to qualitative genetic differences.

The present invention is equally directed to the preparation of nucleic acid libraries, to the nucleic acids and libraries thus prepared, as well as to uses of such materials in all fields of biology/biotechnology, as illustrated hereinafter.

In this respect, the invention is equally directed to a method for preparing profiled nucleic acid compositions or libraries, representative of qualitative differences occurring between two biological samples, comprising hybridizing RNAs derived from a first biological sample with cDNAs originating from a second biological sample.

The invention further concerns a method for profiling a cDNA composition, comprising hybridizing this composition with RNAs, or vice versa.

As indicated hereinabove, the present invention relates in particular to methods for identifying and cloning nucleic acids representative of a physiological state. In addition, the nucleic acids identified and/or cloned represent the qualitative characteristics of a physiological state in that these nucleic acids are generally involved to a great extent in the physiological state being observed. Thus, the qualitative methods of the invention afford direct exploration of genetic elements or protein products thereof, playing a functional role in the development of a pathophysiological state.

The methods of the invention are partly based on an original step consisting of cross hybridization between RNAs and cDNAs belonging to distinct physiological states. This or these cross hybridization procedures advantageously allow one to demonstrate, in the hybrids formed, unpaired regions, i.e. regions present in RNAs in a given physiological condition and not in RNAs from another physiological condition. Such regions essentially correspond to alternative forms of splicing typical of a physiological state, but may also be a reflection of genetic alterations such as insertions or deletions, and thus form genetic elements particularly useful in the fields of therapeutics and diagnostics as set forth below. The invention therefore consists notably in keeping the complexes formed after cross hybridization(s), so as to deduce therefrom the regions corresponding to qualitative differences. This methodology can be distinguished from quantitative subtraction techniques known to those skilled in the art (Sargent and Dawid (1983), Science, 222: 135-139; Davis et al. (1984), PNAS, 81: 2194-2198; Duguid and Dinauer (1990), Nucl. Acid Res., 18: 2789-2792; Diatchenko et al. (1996), PNAS, 93: 6025-6030), which discard the hybrids formed after hybridization(s) so as to conserve only the non-hybridized nucleic acids.

The invention therefore first deals with a method for identifying nucleic acids of interest comprising hybridizing the RNAs of a test sample with the cDNAs of a reference sample. This hybridization procedure makes it possible to identify, in the complexes formed, qualitative genetic differences between the conditions under study, and thus to identify and/or clone for example the splicings which are characteristic of the test condition.

Figure 1B:
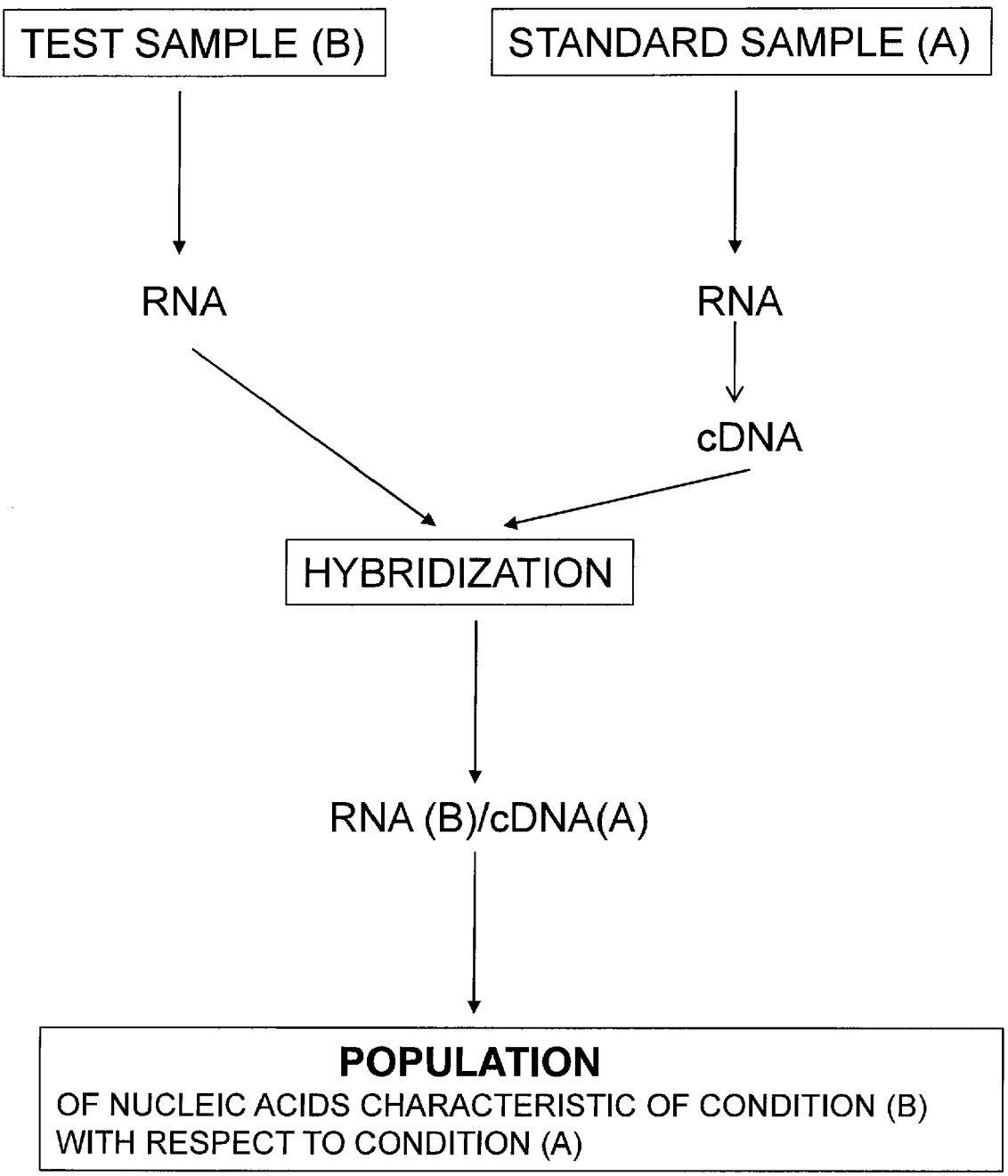
Figure 1C:
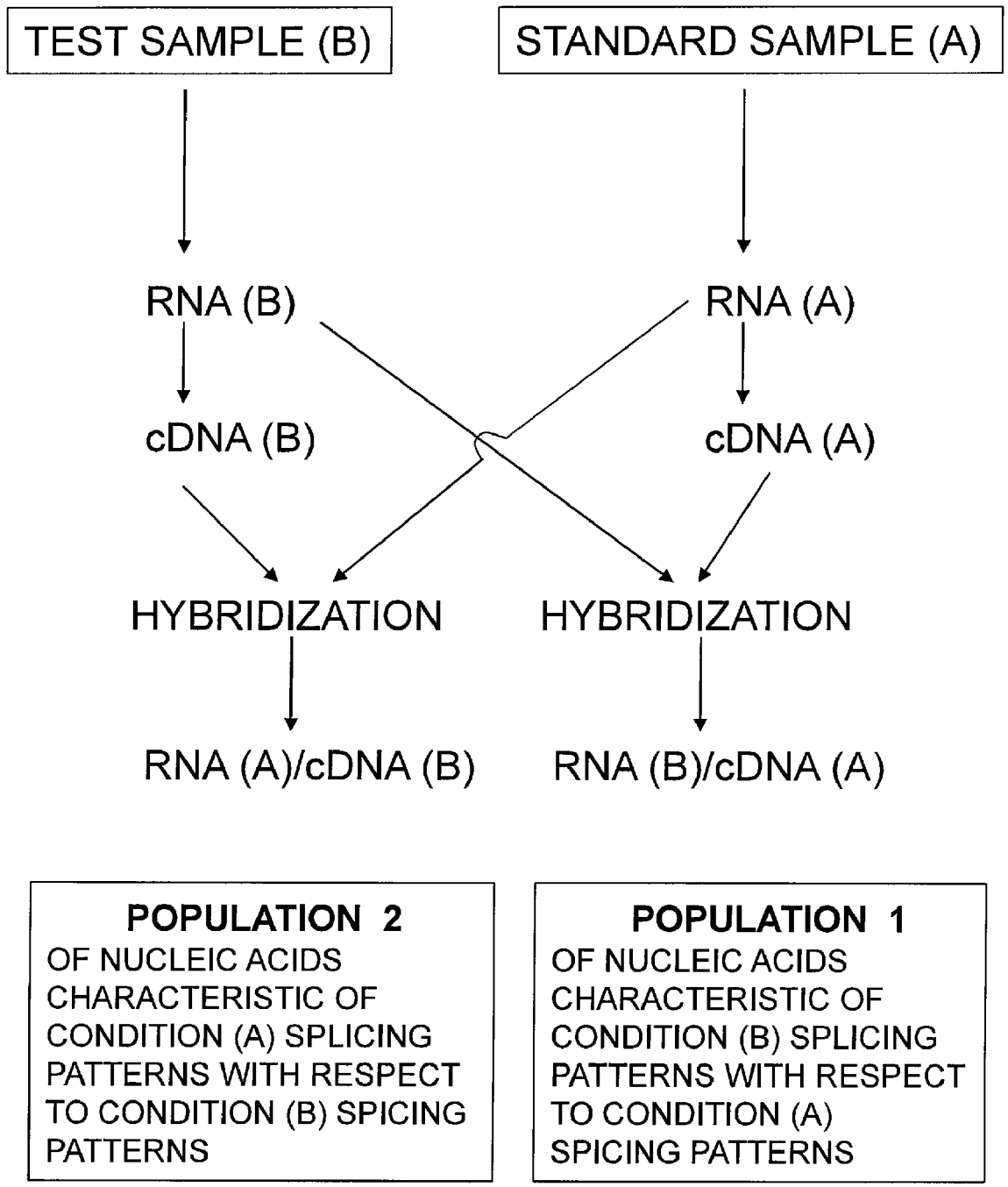
Figure 1D:
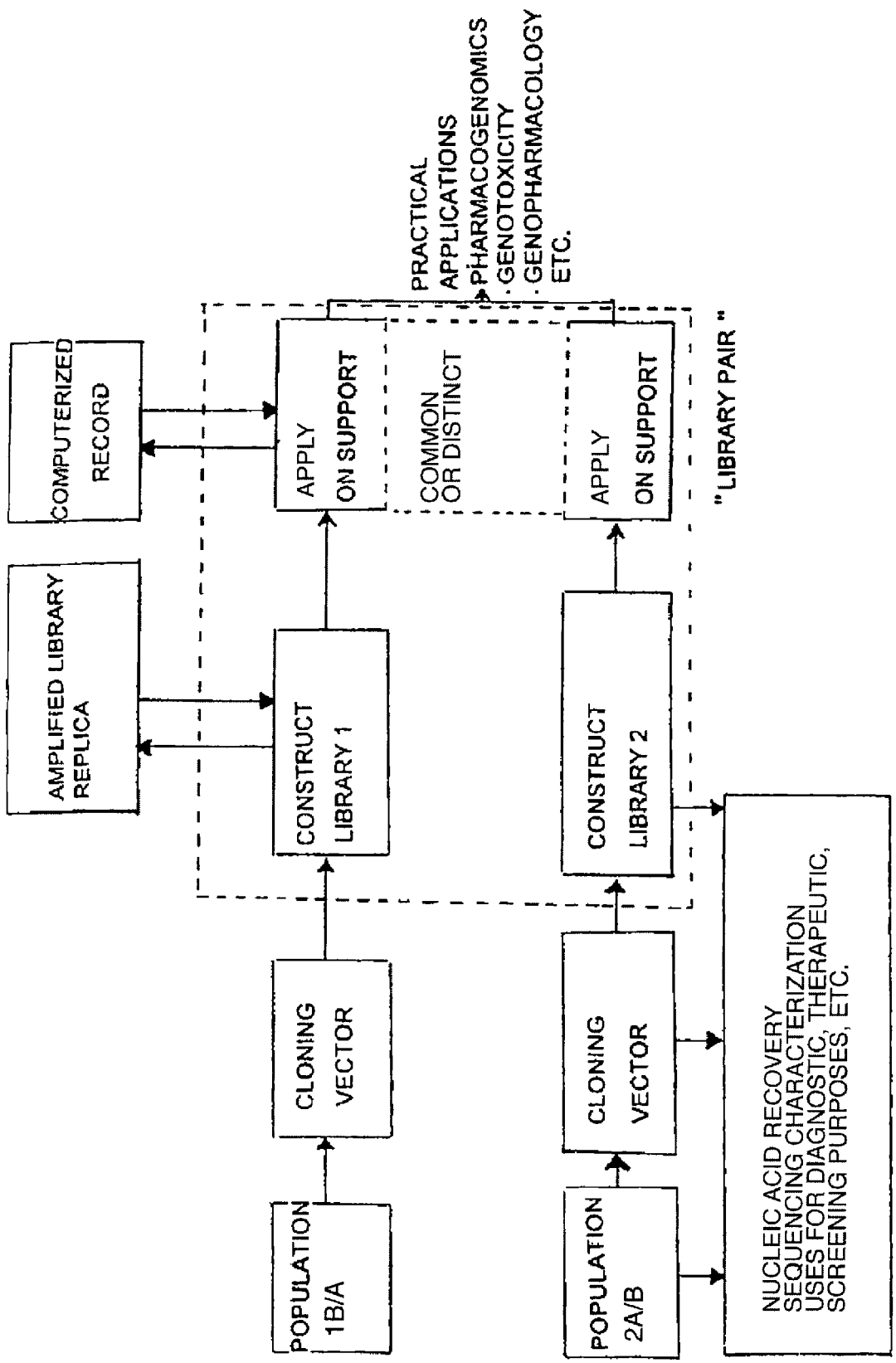

According to a first variant of the invention, the method therefore allows one to generate a nucleic acid population characteristic of splicing events that occur in the physiological test condition as compared to the reference condition (FIG. 1A, 1B). As indicated hereinafter, this population can be used for the cloning and characterization of nucleic acids, their use in diagnostics, screening, therapeutics and antibody production or synthesis of whole proteins or protein fragments. This population can also be used to generate libraries that may be used in different fields of application as shown hereinafter and to generate labeled probes (FIG. 1D).

According to another variant of the invention, the method comprises a first hybridization as described hereinbefore and a second hybridization, conducted in parallel, between RNAs derived from the reference condition and cDNAs derived from the test condition. This variant is particularly advantageous since it allows one to generate two nucleic acid populations, one representing the qualitative characteristics of the test condition with respect to the reference condition, and the other representing the qualitative characteristics of the reference condition in relation to the test condition (FIG. 1C). These two populations can also be utilized as nucleic acid sources, or as libraries which serve as genetic fingerprints of a particular physiological condition, as will be more fully described in the following (FIG. 1D).

The present invention may be applied to all types of biological samples. In particular, the biological sample can be any cell, organ, tissue, sample, biopsy material, etc. containing nucleic acids. In the case of an organ, tissue or biopsy material, the samples can be cultured so as to facilitate access to the constituent cells. The samples may be derived from mammals (especially human beings), plants, bacteria and lower eukaryotes (yeasts, fungal cells, etc.). Relevant materials are exemplified in particular by a tumor biopsy, neurodegenerative plaque or cerebral zone biopsy displaying neurodegenerative signs, a skin sample, a blood sample obtained by collecting blood, a colorectal biopsy, biopsy material derived from bronchioalveolar lavage, etc. Examples of cells include notably muscle cells, hepatic cells, fibroblasts, nerve cells, epidermal and dermal cells, blood cells such as B and T lymphocytes, mast cells, monocytes, granulocytes and macrophages.

As indicated hereinabove, the qualitative differential screening according to the present invention allows the identification of nucleic acids characteristic of a given physiological condition (condition B) in relation to a reference physiological condition (condition A), that are to be cloned or used for other applications. By way of illustration, the physiological conditions A and B being investigated may be chosen among the following:

| CONDITION A | CONDITION B |
|---|---|
| Healthy subject-derived sample | Pathological sample |
| Healthy subject-derived sample | Apoptotic sample |
| Healthy subject-derived sample | Sample obtained after viral infection |
| X-sensitive sample | X-resistant sample |
| Untreated sample | Treated sample (for example by a toxic compound) |
| Undifferentiated sample | Sample that has undergone cellular or tissue differentiation |

RNA Populations

The present invention can be carried out by using total RNAs or messenger RNAs. These RNAs can be prepared by any conventional molecular biology methods, familiar to those skilled in the art. Such methods generally comprise cell, tissue or sample lysis and RNA recovery by means of extraction procedures. This can be done in particular by treatment with chaotropic agents such as guanidium thiocyanate (which disrupts the cells without affecting RNA) followed by RNA extraction with solvents (phenol, chloroform for instance). Such methods are well known in the art (see Maniatis et al., Chomczynski et al., (1987), Anal. Biochem., 162: 156). These methods may be readily implemented by using commercially available kits such as for example the US73750 kit (Amersham) or the Rneasy kit (Quiagen) for total RNAs. It is not necessary that the RNA be in a fully pure state, and in particular, traces of genomic DNA or other cellular components (protein, etc.) remaining in the preparations will not interfere, in as much as they do not significantly affect RNA stability and as the modes of preparation of the different samples under comparison are the same. Optionally, it is further possible to use messenger RNA instead of total RNA preparations. These may be isolated, either directly from the biological sample or from total RNAs, by means of polyT sequences, according to standard methods. In this respect, the preparation of messenger RNAs can be carried out using commercially available kits such as for example the US72700 kit (Amersham) or the kit involving the use of oligo-(dT) beads (Dynal). An advantageous method of RNA preparation consists in extracting cytosolic RNAs and then cytosolic polyA+ RNAs. Kits allowing the selective preparation of cytosolic RNAs that are not contaminated by premessenger RNAs bearing unspliced exons and introns are commercially available. This is the case in particular for the Rneasy kit marketed by Qiagen (example of catalog number 74103). RNAs can also be obtained directly from libraries or other samples prepared beforehand and/or available from collections, stored under suitable conditions.

Generally, the RNA preparations used advantageously comprise at least 0.1 µg of RNA, preferably at least 0.5 µg of RNA. Quantities can vary depending on the particular cells and methods being used, while keeping the practice of the invention unchanged. In order to obtain sufficient quantities of RNA (preferably at least 0.1 µg), it is generally recommended to use a biological sample including at least $10^5$ cells. In this respect, a typical biopsy specimen generally comprises from $10^5$ to $10^8$ cells, and a cell culture on a typical petri dish (6 to 10 cm in diameter) contains about $10^8$ cells, so that sufficient quantities of RNA can be readily obtained.

The RNA preparations may be used extemporaneously or stored, preferably in a cold place, as a solution or in the frozen state, for later use.

cDNA Populations

The cDNA used within the scope of the present invention may be obtained by reverse transcription according to conventional molecular biology techniques. Reference is made in particular to Maniatis et al. Reverse transcription is generally carried out using an enzyme, reverse transcriptase, and a primer.

In this respect, many reverse transcriptases have been described in the literature and are commercially available (1483188 kit, Boehringer). Examples of the most commonly employed reverse transcriptases include those derived from avian virus AMV (Avian Myeloblastosis Virus) and from murine leukemia virus MMLV (Moloney Murine Leukemia Virus). It is also worth mentioning certain thermostable DNA polymerases having reverse transcriptase activity such as those isolated from *Thermus flavus* and *Thermus thermophilus* HB-8 (commercially available; Promega catalog numbers M1941 and M2101). According to an advantageous variant, the present invention is practiced using AMV reverse transcriptase since this enzyme, active at 42° C. (in contrast to that of MMLV which is active at 37° C.), destabilizes certain RNA secondary structures that might stop elongation, and therefore allows reverse transcription of RNA of greater length, and provides cDNA preparations in high yields that are much more faithful copies of RNA.

According to a further advantageous variant of the invention, a reverse transcriptase devoid of RNaseH activity is employed. The use of this type of enzyme has several advantages, particularly that of increasing the yield of cDNA synthesis and avoiding any degradation of RNAs, which will then be engaged in heteroduplex formation with the newly synthesized cDNAs, thereby optionally making it possible to omit the phenol extraction of the latter. Reverse transcriptases devoid of RNaseH activity may be prepared from any reverse transcriptase by deletion(s) and/or mutagenesis. In addition, such enzymes are also commercially available (for example Life Technologies, catalog number 18053-017).

The operating conditions that apply to reverse transcriptases (concentration and temperature) are well known to those skilled in the art. In particular, 10 to 30 units of enzyme are generally used in a single reaction, in the presence of an optimal $Mg^{2+}$ concentration of 10 mM.

The primer(s) used for reverse transcription may be of various types. It might be, in particular, a random oligonucleotide comprising preferably from 4 to 10 nucleotides, advantageously a hexanucleotide. Use of this type of random primer has been described in the literature and allows random initiation of reverse transcription at different sites within the RNA molecules. This technique is especially employed for reverse transcribing total RNA (i.e. comprising mRNA, tRNA and rRNA in particular). Where it is desired to carry out reverse transcription of mRNA only, it is advantageous to use an oligo-dT oligonucleotide as primer, which allows initiation of reverse transcription starting from polyA tails specific to messenger RNAs. The oligo-dT oligonucleotide may comprise from 4 to 20-mers, advantageously about 15-mers. Use of such a primer represents a preferred embodiment of the invention. In addition, it might be advantageous to use a labeled primer for reverse transcription. As a matter of fact, this allows recognition and/or selection and/or subsequent sorting of RNA from cDNA. This may also allow one to isolate RNA/DNA heteroduplexes the formation of which represents a crucial step in the practice of the invention. Labeling of the primer may be done by any ligand-receptor based system, i.e. providing affinity mediated separation of molecules bearing the primer. It may consist for instance of biotin labeling, which can be captured on any support (bead, column, plates, etc.) previously coated with streptavidin. Any other labeling system allowing separation without affecting the properties of the primer may be likewise utilized.

In typical operating conditions, this reverse transcription generates single stranded complementary DNA (cDNA). This represents a first advantageous embodiment of the present invention.

In a second variant of practicing the invention, reverse transcription is accomplished such that double stranded cDNAs are prepared. This result is achieved by generating, following transcription of the first cDNA strand, the second strand using conventional molecular biology techniques involving enzymes capable of modifying DNA such as phage T4 DNA ligase, DNA polymerase I and phage T4 DNA polymerase.

The cDNA preparations may be used extemporaneously or stored, preferably in a cold place, as a solution or in the frozen state, for later use.

Hybridizations

As set forth hereinabove, the methods according to the invention are partly based on an original cross hybridization step between RNAs and cDNAs derived from biological samples in distinct physiological conditions or from different origins. In a preferred embodiment, hybridization according to the invention is advantageously performed in the liquid phase. Furthermore, it may be carried out in any appropriate device, such as for example tubes (Eppendorff tubes, for instance), plates or any other suitable support that is commonly used in molecular biology. Hybridization is advantageously carried out in volumes ranging from 10 to 1000 µl, for example from 10 to 500 µl. It should be understood that the particular device as well as the volumes used can be easily adapted by those skilled in the art. The amounts of nucleic acids used for hybridization are equally well known in the art. In general, it is sufficient to use a few micrograms of nucleic acids, for example in the range of 0.1 to 100 µg.

An important factor to be considered when performing hybridization is the respective quantities of nucleic acids used. Thus, it is possible to use nucleic acids in a cDNA/RNA ratio ranging from 50 to 0.02 approximately, preferably from 40 to 0.1. In a more particularly advantageous manner, the cDNA/RNA ratio is preferably close to or greater than 1. Indeed, in such experiments, RNA forms the tester compound and cDNA forms the driver. Accordingly, in order to improve the is specificity of the method, it is preferred to choose operating conditions where the driver is in excess relative to the tester. In fact, in such conditions, the cooperativity effect between nucleic acids occurs and mismatches are strongly disfavored. As a result, the only mismatches that are observed are generally due to the presence of regions in the tester RNA which are absent from the driver cDNA and which can therefore be considered as specific. In order to enhance the specificity of the method, hybridization is therefore advantageously performed using a cDNA/RNA ratio comprised between about 1 and about 10. It is understood that this ratio can be adapted by those skilled in the art depending on the operating conditions (nucleic acid quantities available, physiological conditions, required results, etc.). The other hybridization parameters (time, temperature, ionic strength) are also adaptable by those skilled in the art. Generally speaking, after denaturation of the tester and driver (by heating for instance), hybridization is accomplished for about 2 to 24 hours, at a temperature of approximately 37° C. (and by optionally performing temperature shifts as set forth below), and under standard ionic strength conditions (ranging from 0.1 M to 5 M NaCl for instance). It is known that ionic strength is one of the factors that defines hybridization, stringency, notably in the case of hybridization on a solid support.

According to a specific embodiment of the invention, hybridization is carried out in phenol emulsion, for instance according to the PERT technique (Phenol Emulsion DNA Reassociation Technique) described by Kohne D. E. et al (Biochemistry, (1977), 16 (24): 5329-5341). Advantageously, use is made within the scope of the present invention of phenol emulsion hybridization under temperature cycling (temperature shifts from about 37° C. to about 60/65° C.) instead of stirring, according to the technique of Miller and Riblet (NAR, (1995), 23: 2339). Any other liquid phase hybridization technique, notably in emulsion phase, may be used within the scope of the present invention. Thus, in another particularly advantageous embodiment, hybridization is carried out in a solution containing 80% formamide, at a temperature of 40° C. for instance.

Hybridization may also be carried out with one of the partners fixed to a support. Advantageously, the cDNA is immobilized. This may be done by taking advantage of cDNA labeling (see hereinabove), especially by using biotinylated primers. Biotin moieties are contacted with magnetic beads coated with streptavidin molecules. cDNAs can then be held in contact with the filter or the microtiter dish well by applying a magnetic field. Under appropriate ionic strength conditions, RNAs are subsequently contacted with cDNAs. Unpaired RNAs are eliminated by washing. Hybridized RNAs as well as cDNAs are recovered upon removal of the magnetic field.

Where the cDNA is double stranded, the hybridization conditions used are essentially similar to those described hereinabove, and adaptable by those skilled in the art. In this case, hybridization is preferably performed in the presence of formamide and the complexes are exposed to a range of temperatures varying for instance from 60 to 40° C., preferably from 56° C. to 44° C., so as to promote the formation of R-loop complexes. In addition, it is desirable to add, following hybridization, a stabilizing agent to stabilize the triplex structures formed, once formamide is removed from the medium, such as glyoxal for example (Kaback et al., (1979), Nuc. Acid Res., 6: 2499-2517).

These cross hybridizations according to the invention thus generate compositions comprising cDNA/RNA heteroduplex or heterotriplex structures, representing the qualitative properties of each physiological condition being tested. As already noted, in each of the present compositions, nucleic acids essentially corresponding to differential alternative splicing or to other genetic alterations, specific to each physiological condition, can be identified and/or cloned.

The invention therefore advantageously relates to, a method for identifying and/or cloning nucleic acid regions representative of genetic differences occurring between two physiological conditions, comprising hybridizing RNAs derived from a biological sample in a first physiological condition with single stranded cDNAs derived from a biological sample in a second physiological condition, and identifying and/or cloning, from the hybrids thus formed, unpaired RNA regions.

Figure 2:
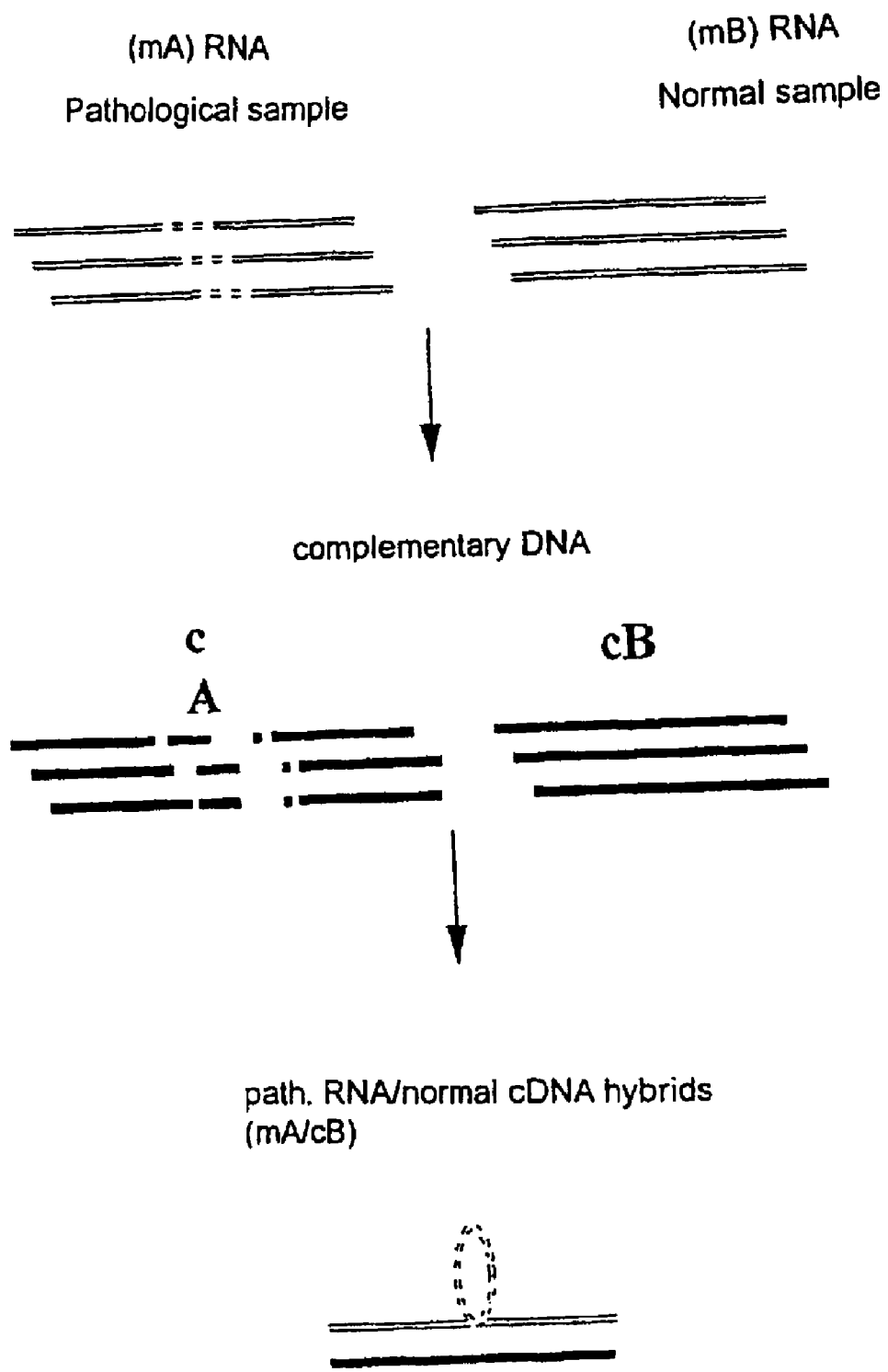
Figure 4:
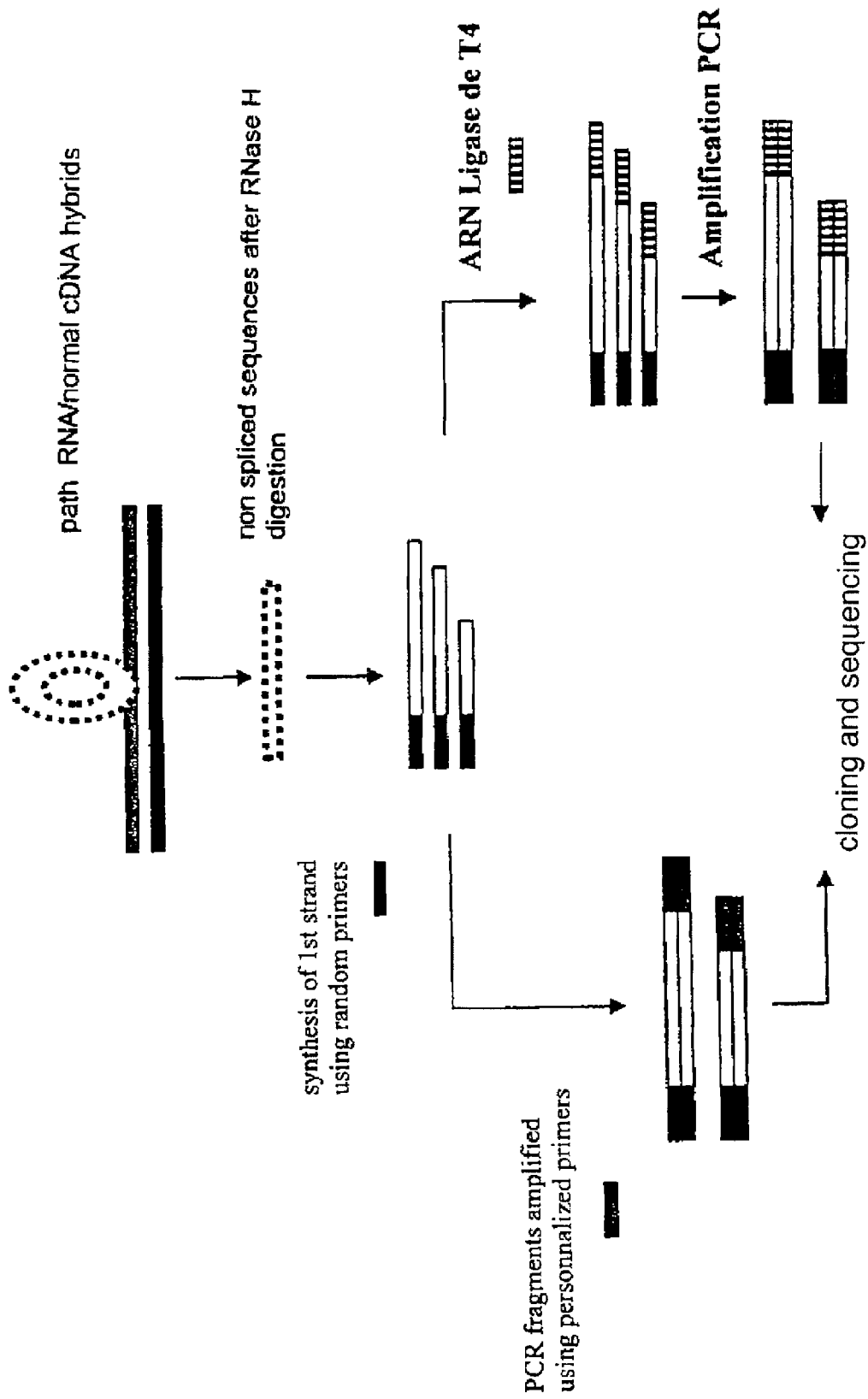

This first variant is more specifically based upon the formation of heteroduplex structures between RNAs and single stranded cDNAs (see FIGS. 2-4). This variant is advantageously implemented using messenger RNAs or cDNAs produced by reverse transcription of essentially messenger mRNAs, i.e. in the to presence of an oligo-dT primer.

In a particular embodiment, the method for identifying and/or cloning nucleic acids according to the invention comprises:

(a) hybridizing RNAs derived from the test condition with single stranded cDNAs derived from the reference condition;

(b) hybridizing RNAs derived from the reference condition with single stranded cDNAs derived from the test condition; and (c) identifying and/or cloning, from the hybrids formed in steps (a) and (b), unpaired RNA regions.

In a particular alternative mode of execution, the method of the invention comprises the following steps:

(a) obtaining RNAs from a biological sample in a physiological condition A (rA);

(b) obtaining RNAs from an identical biological sample in a physiological condition B (rB);

(c) preparing cDNAs from a portion of rA RNAs provided in step (a) (cA cDNAs) and from a portion of rB RNAs provided in step B (cB cDNAs) by means of polyT primers, (d) hybridizing in liquid phase a portion of rA RNAs with a portion of cB DNAs (to generate rA/cB heteroduplexes)

(e) hybridizing in liquid phase a portion of rB RNAs with a portion of cA DNAs (to generate rB/cA heteroduplexes), (f) identifying and/or cloning unpaired RNA regions within the rA/cB and rB/cA heteroduplexes obtained in steps (d) and (e).

According to an alternative mode of practicing the invention, the method of the invention comprises hybridizing RNAs derived from the test condition with double stranded cDNAs derived from the reference condition, and identifying and/or cloning the resulting double stranded DNA regions. This second variant is more specifically based upon the formation of heterotriplex structures between RNAs and double stranded cDNAs, derived from R-loop type structures (see FIG. 5). This variant is equally preferentially practiced by using messenger RNAs or cDNAs produced by reverse transcription of essentially messenger RNA, i.e. in the presence of a polyT primer. In this variant again, a particular embodiment comprises running two hybridizations in parallel, whereby two nucleic acid populations according to the invention are generated. In this variant, the desired regions, specific of alternative splicing events, are not the unpaired RNA regions, but instead double stranded DNA which was not displaced by a homologous RNA sequence (see FIG. 5).

In another variant of the invention, the method to detect qualitative genetic differences (eg., alternative splicing events) occurring between two samples, comprises hybridizing double stranded cDNAs derived from a first biological sample with cDNAs (double stranded or, preferably single stranded) derived from a second biological sample (FIG. 6). Unlike the variants described hereinabove, this variant does not make use of DNA/RNA heteroduplex or heterotriplex structures, but instead of DNA/DNA homoduplexes. This variant is advantageous in that it reveals not only alternative introns and exons but also, and within a same nucleic acid library, specific junctions formed by deletion of an exon or an intron. Furthermore, the sequences in such a library give information about the flanking sequences of alternative introns and exons.

Figure 6A:
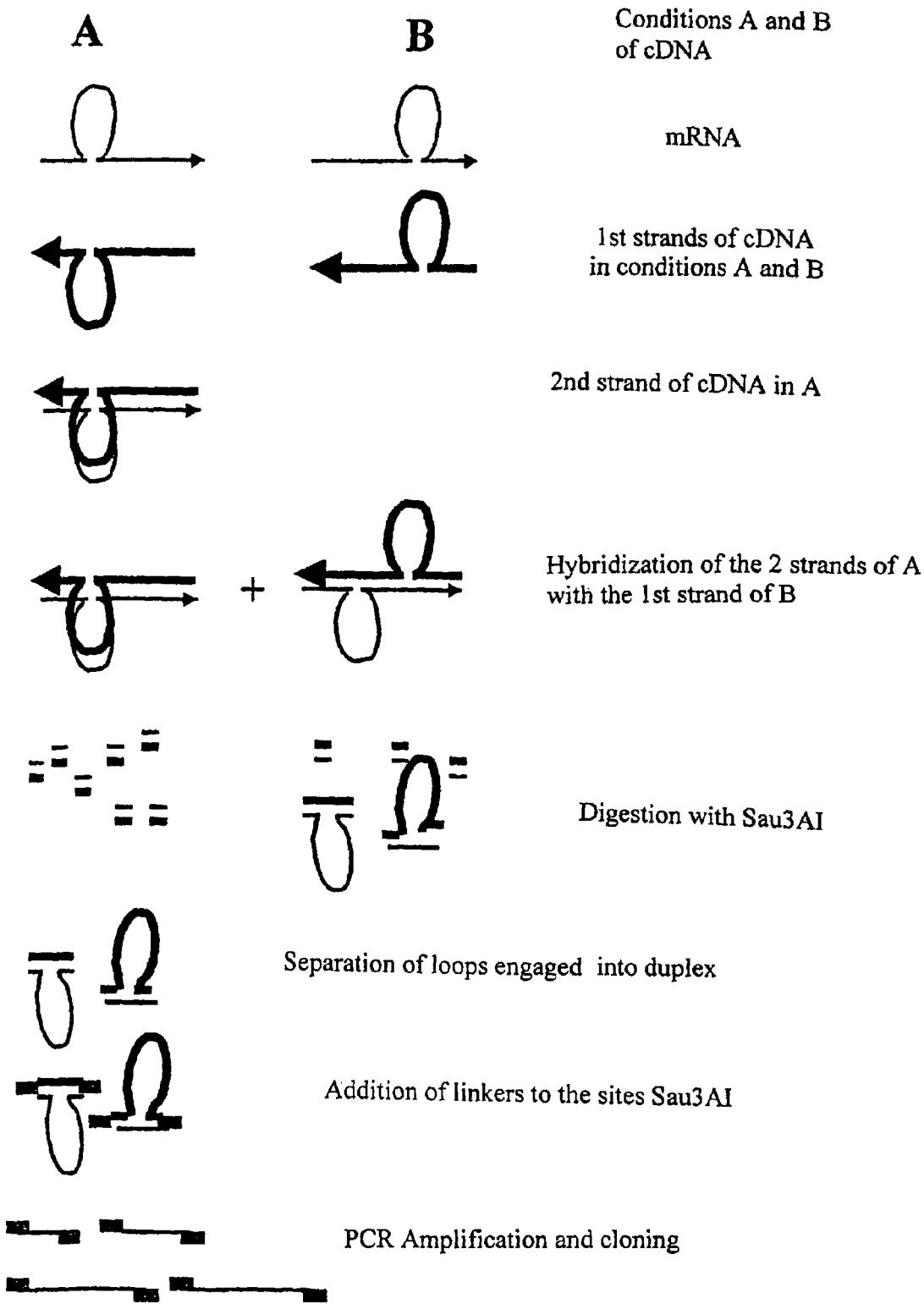

For both samples (i.e. pathophysiological conditions) under study, cytosolic polyA+ RNAs are extracted by techniques known in the art and described previously. These RNAs are converted to cDNA through the action of a reverse transcriptase with or without intrinsic RNase H activity, as described hereinabove. One of these single stranded cDNAs is then converted to double stranded cDNA by priming with random hexamers and according to techniques known to those skilled in the art. For one of the conditions under study one therefore has a single stranded cDNA (called a "driver") and for the other condition, a double-stranded cDNA (called a "tester"). These cDNAs are denatured by heating and then mixed such that the driver is in excess relative to the tester. This excess is chosen between 1 and 50-fold, advantageously 10-fold. In a given experiment, conducted starting with two pathophysiological conditions, the choice of the condition which generates the driver is arbitrary and must not affect the nature of the data collected. As a matter of fact, as in the case of the approaches described hereinabove, the strategy for identifying qualitative differences occurring between two mRNA populations is based on cloning these differences present in common messengers: the strategy is based on cloning sequences present within duplexes instead of single strands corresponding to unique sequences or sequences in excess in one of the conditions under study. The to mixture of cDNAs is precipitated, then taken up in a solution containing formamide (for example, 80%). Hybridization is carried out for 16 hours to 48 hours, advantageously for 24 hours. The hybridization products are precipitated, then subjected to the action of a restriction endonuclease having a 4-base recognition site for double stranded DNA. Such a restriction enzyme will therefore cleave the double stranded cDNA formed during the hybridization on average every 256 bases. This enzyme is advantageously chosen so as to generate cohesive ends. Such enzymes are exemplified by restriction enzymes such as Sau3AI, HpaII, TaqI and MseI. The double stranded fragments digested by these enzymes are therefore accessible to a cloning strategy making use of the cleaved restriction sites. Such fragments are of two types: fully hybridized fragments, the two strands of which are fully complementary, and partially hybridized fragments, i.e. comprising a single stranded loop flanked by double stranded regions (FIG. 6A). These latter fragments, which are in the minority, contain the information of interest. In order to separate them from fully hybridized fragments, which are in the majority since they are derived from most of the cDNA length, separation methods on a gel or on any other suitable matrix are used. These methods take advantage of the slower migration, during electrophoresis or gel filtration in particular, of DNA fragments which contain a single stranded DNA loop. In this manner the minority fragments which contain the desired information can be preparatively separated from the majority of fragments corresponding to identical DNA regions in both populations. This variant, which makes it possible to isolate, from a same population, positive and negative fingerprints linked to qualitative differences, can also be practiced with RNA/DNA heteroduplex structures. In this respect, an example of slower migration of a RNA/DNA heteroduplex in which a portion of the RNA is not paired, as compared to a homologous heteroduplex in which all the sequences are paired, is illustrated in the grb2/grb33 model described in the examples (in particular see FIG. 8, lanes 2 and 3).

Identification and/or Cloning

Starting from nucleic acid populations generated by hybridization, the regions characterizing qualitative differences (eg., differential alternative splicing events), may be identified by any technique known to those skilled in the art.

Identification and/or Cloning Starting with RNA/DNA Heteroduplexes

Hence, in case of an RNA/DNA heteroduplex (first variant of this method), these regions essentially appear as unpaired RNA regions (RNA loops), as shown in FIG. 3. These regions may thus be identified and cloned by separating the heteroduplexes and single stranded nucleic acids (DNA, RNA) (unreacted nucleic acids in excess), selectively digesting the double stranded RNA (portions engaged in heteroduplex structures) and finally separating the resulting single stranded RNA from the single stranded DNA.

In this respect, according to a first approach illustrated in FIG. 3, the unpaired RNA regions are identified, by treatment of heteroduplexes by means of an enzyme capable of selectively digesting the RNA domains engaged in RNA/DNA heteroduplexes. Enzymes having such activity are known from the prior art and are commercially available. It can be mentioned RNases H, such as in particular, those derived from *E. coli* by recombinant techniques and commercially available (Promega catalog number M4281; Life Technologies catalog number 18021). This first treatment thus generates a mixture comprising unpaired single stranded RNA regions and single stranded cDNA. The RNAs may be separated from cDNAs by any technique known in the art, and notably on the basis of labeling of those primers used to prepare cDNA (see above). These RNAs can be used as a source of material for identifying targets, gene products of interest or for any other application. These RNAs can be equally converted into cDNA, and then cloned into vectors, as described hereinafter.

In this regard, cloning RNAs may be done in different ways. One way is to insert at each RNA end oligonucleotides acting as templates for a reverse transcription reaction in the presence of compatible primers. Primers may be appended according to techniques well known to those skilled in the art by means of an enzyme, such as for example RNA ligase derived from phage T4 and which catalyzes intermolecular phosphodiester bond formation between a 5' phosphate group of a donor molecule and a 3' hydroxyl group of an acceptor molecule. Such an RNA ligase is commercially available (for example Life Technologies—GIBCO BRL catalog number 18003). The cDNAs thus obtained may then be amplified by conventional techniques (PCR for example) using the appropriate primers, as illustrated in FIG. 3. This technique is especially adapted to cloning short RNA molecules (less than 1000 bases).

Another approach for cloning and/or identifying specific RNA regions involves for example a reverse transcription reaction, performed upon the digests of an enzyme acting specifically on double stranded RNA, such as RNase H, using random primers, which will randomly initiate transcription along RNAs. cDNAs thus obtained are then amplified according to conventional molecular biology techniques, for example by PCR using primers formed by appending oligonucleotides to cDNA ends by means of T4 phage DNA ligase (commercially available; for example from Life Technologies—GIBCO BRL catalog number 18003). This second technique is illustrated in FIG. 4 and in the examples. This technique is especially adapted to long RNAs, and provides a sufficient part of the sequence data to subsequently reconstruct the entire initial sequence.

A further approach for cloning and/or identifying specific RNA regions is equally based on a reverse transcription reaction using random primers (FIG. 4). However, according to this variant, the primers used are at least in part semi-random primers, i.e. oligonucleotides comprising:
- a random (degenerated) region,
- a minimal priming region having a defined degree of constraint, and
- a stabilizing region.

Preferably, these are oligonucleotides comprising, in the 5'→3' direction:
- a stabilizing region comprising 8 to 24 defined nucleotides, preferably 10 to 18 nucleotides. This stabilizing region may itself correspond to the sequence of an oligonucleotide used to reamplify fragments derived from initial amplifications performed by means of the semi-random primers of the invention. In addition, the stabilizing region may comprise the sequence of one or more sites, preferably non-palindromic, corresponding to restriction enzymes. This makes it possible for example to simplify the cloning of the fragments thus amplified. A particular example of a stabilizing region is given by the sequence GAG AAG CGT TAT (residues 1 to 12 of SEQ ID NO:1);
- a random region having 3 to 8 nucleotides, more particularly 5 to 7 nucleotides, and
- a minimal priming region defined such that the oligonucleotide hybridizes on average at least about every 60 base pairs, preferably about every 250 base pairs. More preferentially, the priming region comprises 2 to 4 defined nucleotides, preferably 3 or 4, such as for example AGGX, where X is one of the four bases A, C, G or T. The presence of such a priming region gives the oligonucleotide the capacity to hybridize on average about every 256 base pairs.

In an especially preferential manner, the oligonucleotides have the formula:

GAGAAGCGTTATNNNNNNNAGGX (SEQ ID NO: 1)

where the fixed bases are ordered so as to minimize background due to self-pairing in PCR experiments, where N indicates that the four bases may be present in a random fashion at the indicated position, and where X is one of the four bases A, C, G or T. Such oligonucleotides equally constitute an object of the present invention.

In this respect, so as to increase the priming events on the RNAs to be cloned, reactions may be carried out in parallel with oligonucleotides such as:

```
GAGAAGCGTTATNNNNNNNAGGT    (oligonucleotides A)

GAGAAGCGTTATNNNNNNNAGGA    (oligonucleotides B)

GAGAAGCGTTATNNNNNNNAGGC    (oligonucleotides C)

GAGAAGCGTTATNNNNNNNAGGG    (oligonucleotides D)
``` each oligonucleotide population (A, B, C, D) being able to be used alone or in combination with another.

After the reverse transcription reaction, the cDNAs are amplified by PCR using oligonucleotides A or B or C or D.

As indicated hereinabove, depending on the complexity and the specificity of the desired oligonucleotide population, the number of degenerated positions may range from 3 to 8, preferably from 5 to 7. Below 3 hybridizations are limited and above 8 the oligonucleotide population is too complex to ensure good amplification of specific bands.

Furthermore, the length of the fixed 3' end (constrained priming region) of these oligonucleotides may also be modified: while the primers described above, with 4 fixed bases, allow amplification of 256 base pair fragments on average, primers with 3 fixed bases allow amplification of shorter fragments (64 base pairs on average). In a first preferred embodiment of the invention, one uses oligonucleotides in which the priming region comprises 4 fixed bases. In another preferred embodiment of the invention, one uses oligonucleotides having a priming region of 3 fixed bases. In fact, as exons have an average size of 137 bases, they are advantageously amplified with such oligonucleotides. In this respect, refer also to oligonucleotides with sequence SEQ ID NO: 2, 3 and 4, for example.

Finally, in general, the identification and/or cloning step of RNA is based on different methods of PCR and cloning, so as to generate as much information as possible.

Identification and/or Cloning Starting with Heterotriplexes.

Figure 5:
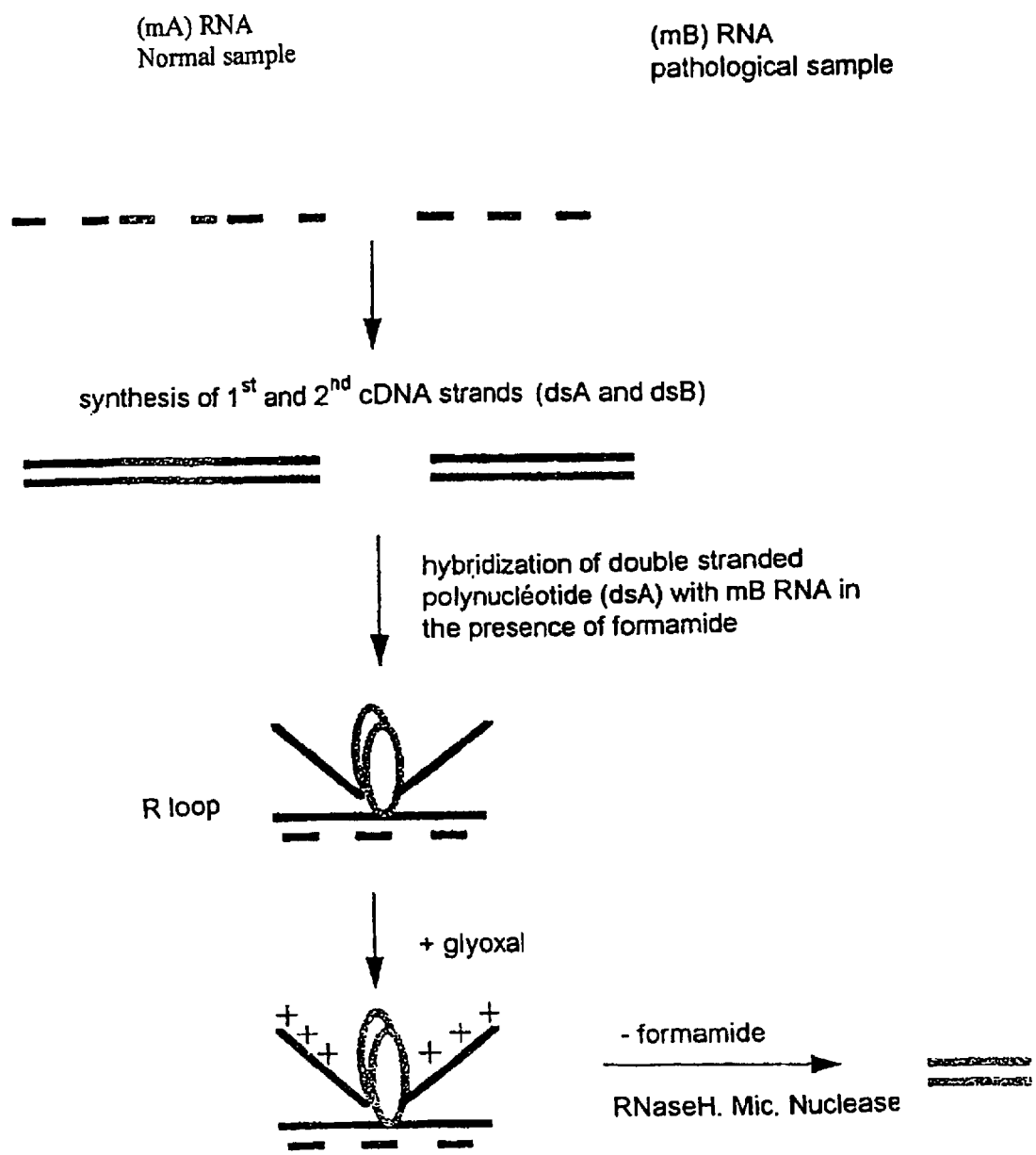

In the case of heterotriplex structures (another variant of the method), the qualitatively different regions (insertions, deletions, differential splicing) appear essentially in the form of double stranded DNA regions, as shown in FIG. 5. Such regions may thus be identified and cloned by treating them in the presence of appropriate enzymes such as an enzyme capable of digesting RNA, and next by an enzyme capable of digesting single stranded DNA. The nucleic acids are thus directly obtained in the form of double stranded DNA and can be cloned into any suitable vector, such as the vector pMos-Blue (Amersham, RPN 5110), for example. This methodology should be distinguished from previously described approaches using RNAs or oligonucleotides of predetermined sequences, modified so as to have nuclease activity (Landgraf et al., (1994), Biochemistry, 33: 10607-10615).

Identification and/or Cloning Starting with DNA/DNA Homoduplexes (FIG. 6).

The fragments isolated on the basis of their atypical structures are then ligated, at each of their ends, to adaptors, or linkers, having cleaved restriction sites at one of their ends. This step may be carried out according to the techniques known to those skilled in the art, for example by ligation with phage T4 DNA ligase. The restriction sites thus introduced are chosen to be compatible with the sites of the cDNA fragments. The linkers introduced are double stranded cDNA sequences, of known sequence, making it possible to generate the primers for enzymatic amplifications (PCR). Since the next step consists in amplifying, the two strands which each bear the qualitative differences to be identified, it is necessary to use linkers with phosphorylated 5' ends. Thus after heat denaturation of double stranded cDNA appended with linkers, each of these cDNA ends is covalently linked to a specific priming sequence. Following PCR by means of appropriate specific primers, two categories of double stranded cDNA are obtained: fragments which contain sequences specific of qualitative differences which distinguish the two pathophysiological conditions, and fragments which comprise the negative fingerprint of these splicing events. Cloning these fragments generates an alternative splicing library in which, for each splicing event, positive and negative fingerprints are present. This library therefore gives access not only to alternative exons and introns but also to the specific junctions formed by excision of these spliced sequences. In a same library, this differential genetic information may be derived from two pathophysiological conditions indiscriminately. Furthermore, so as to check the differential nature of the identified splicing events and so as to determine the condition in which they are specifically elicited, the clones in the library may be hybridized with probes derived from each of the total mRNA populations.

The cDNA fragments derived from the qualitative differences so identified have two principal uses:
- cloning into suitable vectors so as to construct libraries representative of the qualitative differences occurring between the two pathophysiological conditions under study,
- use as probes to screen a DNA library allowing identification of differential splicing events.

The vectors used in the invention can be in particular plasmids, cosmids, phages, YAC, HAC, etc. These nucleic acids may thus be stored as such, or introduced into microorganisms compatible with the cloning vector being used, for replication and/or stored in the form of cultures.

The time interval required for carrying out the methods herein described for each sample is generally less than two months, in particular less than 6 weeks. Furthermore, these different methods may be automated so that the total length of time is reduced and treatment of a large number of samples is simplified.

In this regard, another object of the invention concerns nucleic acids that have been identified and/or cloned by the methods of the invention. As already noted, these nucleic acids may be RNAs or cDNAs. More generally, the invention concerns a nucleic acid composition, essentially comprising nucleic acids corresponding to alternative splicings which are distinctive of two physiological conditions. More particularly, these nucleic acids correspond to alternative splicings identified in a biological test sample and not present in the same biological sample under a reference condition. The invention is equally concerned with the use of the nucleic acids thus cloned as therapeutic or diagnostic products, or as screening tools to identify active molecules, as set forth hereinafter.

The different methods disclosed hereinabove thus all lead to the cloning of cDNA sequences representative of differentially spliced genetic information between two pathophysiological conditions. The whole set of clones derived from one of these methods makes it thus possible to construct a library representative of qualitative differences occurring between two conditions of interest.

Generation of Qualitative Libraries

In this respect, the invention is further directed to a method for preparing nucleic acid libraries representative of a given physiological state of a biological sample. This method advantageously comprises cloning nucleic acids representative of qualitative markers of genetic expression (for example alternative splicings) of said physiological state but not present in a reference state, to generate libraries specific to qualitative differences occurring between the two states being investigated.

These libraries are constituted by cDNA inserted in plasmid or phage vectors. Such libraries can be deposited on nitrocellulose filters or any other support known to those skilled in the art, such as chips or biochips.

One of the features as well as one of the original characteristics of qualitative differential screening is that this technique leads not to one but advantageously to two differential libraries which represent the whole set of qualitative differences occurring between two given conditions: a library pair (see FIG. 1D).

Thus, the invention preferentially concerns any nucleic acid composition or library that can be obtained by hybridizing RNAs derived from a first biological sample with cDNAs derived from a second biological sample. More preferentially, the libraries or compositions of the invention comprise nucleic acids representative of qualitative differences in expression between two biological samples, and are generated by a method comprising (i) at least one hybridization step between RNAs derived from a first biological sample and cDNAs derived from a second biological sample, (ii) selecting those nucleic acids representative of qualitative differences in expression and, optionally, (iii) cloning said nucleic acids.

Furthermore, once such libraries are constructed, it is possible to proceed with a step of clone selection in order to improve the specificity of the resulting libraries. Indeed, it may be that certain mismatches observed are not due solely to qualitative differences (eg., to differential alternative splicings) but might result from reverse transcription defects for example. Although such events are not generally significant, it is preferable to prevent them or reduce their incidence prior to nucleic acid cloning. To accomplish this, the library clones may be hybridized with the cDNA populations occurring in both physiological conditions being investigated (cf. step © hereinabove). The clones which hybridize in a non-differential manner with both populations would be considered as nonspecific and optionally discarded or treated as second priority (in fact, the appearance of a new isoform in the test sample does not always indicate that the initial isoform present in the reference sample has disappeared from this test sample). Clones hybridizing with only one of either populations or hybridizing preferentially with one of the populations are considered specific and could be selected in priority to constitute enriched or refined libraries.

A refining step may be equally performed by hybridizing and checking the identify of clones by means of probes derived from a statistically relevant number of pathological samples.

The present application is therefore equally directed to any nucleic acid library comprising nucleic acids specific to alternative splicings typical of a physiological condition. These libraries advantageously comprise cDNAs, generally double stranded, corresponding to RNA regions specific of alternative splicing. Such libraries may be comprised of nucleic acids, generally incorporated within a cloning vector, or of cell cultures containing said nucleic acids.

The choice of initial RNAs partly determines the characteristics of the resulting libraries:
- the RNAs of both conditions A and B are mRNAs or total mature RNAs isolated according to techniques known to those skilled in the art. The libraries are thus so-called restricted qualitative differential screening libraries, since they are restricted to qualitative differences that characterize the mature RNAs of both pathophysiological conditions.
- the RNAs of one of either conditions are mRNAs or mature total RNAs whereas the RNAs of the other condition are premessenger RNAs, not processed by splicing, isolated according to techniques known to those skilled in the art, from cell nuclei. In this situation the resulting libraries are so-called complex differential screening libraries, as being not restricted to differences between mature RNAs but rather comprising the whole set of spliced transcripts in a given condition which are absent from the other, including all introns.
- finally, the RNAs could arise from a single pathophysiological condition and in this case the differential screening involves mature RNAs and premessenger RNAs of the same sample. In such a case, the resulting libraries are autologous qualitative differential screening libraries. The usefulness of such libraries lies in that they include exclusively the whole range of introns transcribed in a given condition. Whether they hybridize with a probe derived from mature RNAs of a distinct condition allows one to quickly ascertain if the condition under study is characterized by persisting introns while providing for their easy identification.

Generally speaking, the libraries are generated by spreading, on a solid medium (notably on agar medium), of a cell culture transformed by the cloned nucleic acids. Transformation is done by any technique known to those skilled in the art (transfection, calcium phosphate precipitation, electroporation, infection with bacteriophage, etc.). The cell culture is generally a bacterial culture, such as for example E. coli. It may also be a eukaryotic cell culture, notably lower eukaryotic cells (yeasts for example). This spreading step can be performed in sterile conditions on a dish or any other suitable support. Additionally, the spread cultures on agar medium can be stored in a frozen state for example (in glycerol or any other suitable agent). Naturally, these libraries can be used to produce "duplicates", i.e. copies made according to common techniques more fully described hereinafter. Furthermore, such libraries are generally used to prepare an amplified library, i.e. a library comprising each clone in an amplified state. An amplified library is prepared as follows: starting from a spread culture, all cellular clones are recovered and packaged for storage in the frozen state or in a cold place, using any compatible medium. This amplified library is advantageously prepared from E. coli bacterial cultures, and is stored at 4° C., in sterile conditions. This amplified library allows preparation and unlimited replication of any subsequently prepared library containing such clones, on different supports, for a variety of applications. Such a library further allows the isolation and characterization of any clone of interest. Each clone composing the libraries of the invention is indeed a characteristic element of a physiological condition, and constitutes therefore a particularly interesting target for various studies such as the search for markers, antibody production, diagnostics, gene transfer therapy, etc. These different applications are discussed in more detail below. The library is generally prepared as described above by spreading the cultures in an agar medium, on a suitable support (petri dish for example). The advantage of using an agar medium is that each colony can be separated and distinctly recognized. Starting from this culture, identical duplicates may be prepared in substantial amounts simply by replica-plating on any suitable support according to techniques known in the art. Thus, the duplicate may be obtained by means of filters, membranes (nylon, nitrocellulose, etc.) on which cell adhesion is possible. Filters may then be stored as such, at 4° C. for example, in a dried state, in any packing medium that does not alter nucleic acids. Filters may equally be treated in such a manner as to discard cells, proteins, etc., and to retain only such components as nucleic acids. These treatment procedures may notably comprise the use of proteases, detergents, etc. Treated filters may be equally stored in any device or under any condition acceptable for nucleic acids.

The nucleic acid libraries can be equally directly prepared from nucleic acids, by transfer onto biochips or any other suitable device.

The invention is equally directed to any library comprising oligonucleotides specific of alternative splicing events that distinguish two physiological conditions. These are advantageously single stranded oligonucleotides comprising from 5 to 100-mers, preferably less than 50-mers, for example in the range of 25-mers.

These oligonucleotides are specific of alternative splicings representative of a given condition or type of physiological condition. Thus, such oligonucleotides may for example be oligonucleotides representative of alternative splicing events characteristic of apoptotic states. Indeed, it has been reported in the literature that certain alternative splicing events are observed in apoptotic conditions. This holds especially true for splicing within Bclx, Bax, Fas or Grb2 genes for example. By referring to published data or sequences available in the literature and/or in databases, it is possible to generate oligonucleotides specific to spliced or unspliced forms. These oligonucleotides may for example be generated according to the following strategy:

(a) identifying a protein or a splicing event characteristic of an apoptotic condition and the sequence of the spliced domain. This identification procedure can be based upon published data or a compilation of available sequences in databases;

(b) synthesizing artificially one or more oligonucleotides corresponding to one or more regions of this domain, which therefore allow the identification of the unspliced form in the RNAs of a test sample through hybridization;

(c) synthesizing artificially one or more oligonucleotides corresponding to the junction region between two domains separated by the spliced domain. These oligonucleotides therefore allow the identification of the spliced form in the RNAs of a test sample through hybridization;

(d) repeating steps (a) to (c) listed above with other proteins or splicing events characteristic of apoptotic conditions;

(e) transferring upon a first suitable support one or a plurality of oligonucleotides specific to apoptotic forms of messengers identified hereinabove and, upon another suitable support, one or a plurality of oligonucleotides specific to non-apoptotic forms.

The two supports thus obtained may be used to assess the physiological state of cells or test samples, and particularly their apoptotic state, through hybridization of a nucleic acid preparation derived from such cells or samples.

Other similar libraries can be generated using oligonucleotides specific to different pathophysiological states (neurodegeneration, toxicity, proliferation, etc.), thus broadening the range of applications.

Alternative intron or exon libraries can also be in the form of computerized data base systems compiled by systematically analyzing databases in which information about genomes of individual organisms, tissues or cell cultures is recorded. In such a case, the data obtained by elaboration of such virtual databases may be used to generate oligonucleotide primers that will serve in testing two pathophysiological conditions in parallel.

The computerized databases may further be used to derive versatile nucleotide probes, representative of a given class of proteins, or specific of a particular sequence. These probes can then be deposited on the clone libraries derived from different alternative intron and exon cloning techniques in order to appreciate the complexity of these molecular libraries and rapidly determine whether a given class of protein or a given defined sequence is differentially spliced when comparing two distinct pathophysiological states.

A further nucleic acid composition or library according to the invention is an antisense library, generated from the sequences identified according to the methods of the invention (DATAS). To generate this type of library, such sequences are cloned so as to be expressed as RNA fragments corresponding to an antisense orientation relative to the messenger RNAs used for DATAS. This results in a so-called antisense library. This approach preferentially makes use of the cloning variant which allows orientation of the cloned fragments. The usefulness of such an antisense library is that it allows transfection of cell lines and monitoring of all phenotypic alterations whether morphological or enzymatic, or revealed by the use of reporter genes or genes that confer resistance to a selective agent. Analysis of phenotypic variations subsequent to the introduction of an antisense expression vector is generally done after selection of so-called stable clones, i.e. allowing coordinated replication of the expression vector and the host genome. This coordination is enabled through the integration of the expression vector into the cellular genome or, when the expression vector is episomal, through selective pressure. Such selective pressure is applied by treating the transfected cell culture with a toxic agent that can only be detoxified when the product of a gene carried by the expression vector is expressed within the cell. This results in synchronization between host and transgene replication. One advantageously uses episomal vectors derived from the Epstein-Barr virus which allow expression of 50 to 100 vector copies within a given cell (Deiss et al., (1996), EMBO J., 15: 3861-3870; Kissil et al., (1995), J. Biol. Chem, 270: 27932-27936).

The advantage of these antisense libraries related to the DATAS sequences they contain is that they not only allow identification of the gene the expression of which is inhibited to produce the selected phenotype, but also identification of which splicing isoform of this gene was affected. When the antisense fragment targets a given exon, it may be deduced therefrom that the protein domain and thus the function involving this domain counteracts the observed phenotype. In this respect coupling of DATAS with an antisense approach represents a shortcut towards functional genomics.

DNA Chips

The invention is further directed to any support material (membrane, filter, biochip, chip, etc.) comprising a nucleic acid composition or library as defined hereinabove. This may more particularly be a cell library or a nucleic acid library. The invention also concerns any kit or support material comprising several libraries according to the invention. In particular, it may be advantageous to use in parallel a library representative of the qualitative features of a test physiological condition with respect to a reference physiological condition and, as control, a library representative of the features of a reference physiological condition in relation to the test physiological condition (a "library pair"). An advantageous kit according to the invention thus comprises two differential qualitative libraries belonging to two physiological conditions (a "library pair"). According to one particular embodiment, the kits pursuant to the invention comprise several library pairs as defined hereinabove, corresponding to distinct physiological states or to different biological samples for example. The kits may comprise for example these different library pairs arranged serially on a common support.

Generation of Probes

Another use of the cDNA compositions according to the invention, representative of qualitative differences occurring between two pathophysiological states, consists in deriving probes thereof. Such probes may in fact be used to screen differential splicing events between two pathophysiological conditions.

These probes (see FIG. 1D) may be prepared by labeling nucleic acid libraries or populations according to conventional techniques known in the art. Thus, the labeling may be carried out by enzymatic, radioactive, fluorescent, immunological means, etc. The labeling is preferably radioactive or fluorescent. This type of labeling may be accomplished for example by introducing into the nucleic acid population (either after synthesis or during synthesis) labeled nucleotides, enabling their visualization by conventional methods.

One application is therefore to screen a conventional genomic library. Such a library may comprise, depending on whether the vector is derived from a phage or a cosmid, DNA fragments of 10 kb to 40 kb. The number of clones hybridizing with the probes generated by DATAS and representative of differential splicing events occurring between two conditions thus approximately reflects the number of genes affected by alternative splicings, according to whether they are expressed in one or the other condition being investigated.

Preferably, the probes of the invention are used to screen a genomic DNA library (generally of human origin) adapted to identifying splicing events. Such a genomic library is preferably composed of DNA fragments of restricted size (generally cloned into vectors), so as to yield statistically only a single differentially spliceable element, i.e. a single exon or a single exon. The genomic DNA library is therefore prepared by digesting genomic DNA with an enzyme having a recognition site restricted by 4 bases, thus providing the possibility of obtaining by controlled digestion DNA fragments with an average size of 1 kb. Such fragments require the generation of $10^7$ clones to constitute a DNA library representative of a higher eukaryotic genome. Such a library is equally an object of the present application. This library is then hybridized with the probes derived from qualitative differential screening. In fact, for each experiment being investigated and which compares two pathophysiological conditions A and B, two probes (probe pair) are obtained. One probe is enriched in splicing events characteristic of condition A and one probe is enriched in splicing markers characteristic of B. Clones in the genomic library which hybridize preferentially with one of either probe harbor sequences that are preferentially spliced in the corresponding pathophysiological conditions.

The methods of the invention thus provide for the systematic identification of qualitative differences in gene expression. These methods have many applications, related to the identification and/or cloning of molecules of interest, in the fields of toxicology, pharmacology or still, in pharmacogenomics for example.

Applications

The invention is therefore additionally concerned with the use of the methods, nucleic acids or libraries previously described for identifying molecules of therapeutic or diagnostic value. The invention is more specifically concerned with the use of the methods, nucleic acids or libraries described hereinabove for identifying proteins or protein domains that are altered in a pathology.

One of the major strengths of these techniques is, indeed, the identification, within a messenger, and consequently within the corresponding protein, of the functional domains which are affected in a given disorder. This makes it possible to assess the importance of a given domain in the development and persistence of a pathological state. The direct advantage of restricting to a given protein domain the impact of a pathological disorder resides in that the latter can be viewed as a relevant target for screening small molecules for therapeutic purposes. This information further constitutes a key for designing therapeutically active polypeptides that may be delivered by gene therapy; such polypeptides can notably be single chain antibodies derived from neutralizing antibodies directed against domains identified by the techniques herein described.

More specifically, the methods according to the invention provide molecules which:
  may be coding sequences derived from alternative exons.
  may correspond to noncoding sequences borne by introns differentially spliced between two pathophysiological states.

From these two points, different information can be obtained.

Alternative splicings of exons which discriminate between two pathophysiological states reflect a regulatory mechanism of gene expression is capable of modulating (in more precise terms suppressing or restoring) one or a number of functions of a particular protein. Therefore, as the majority of structural and functional domains (SH2, SH3, PTB, PDZ, and catalytic domains of various enzymes) are encoded by several contiguous exons, two configurations might be considered:
  i) the domains are truncated in the pathological condition (Zhu, Q. et al., (1994), J. Exp. Med., 180 (2): 461-470); this indicates that the signaling pathways involving such domains must be restored for therapeutical purposes.
  ii) the domains are retained in the course of a pathological disorder whereas they are absent in the healthy state; these domains can be considered as screening targets for low molecular weight compounds intended to antagonize signal transduction mediated by such domains.

The differentially spliced sequences may correspond to noncoding regions located 5' or 3' of the coding sequence or to introns occurring between two coding exons. In the noncoding regions, these differential splicings could reflect a modification of messenger stability or translatability (Bloom, T. J. and Beavo, J. A., (1995), Proc. Natl. Acad. Sci. USA, 93 (24): 14188-14192; Ambartsumian, N. et al., (1995), Gene, 159 (1): 125-130). A search for these phenomena should be conducted based on such information and might qualify the corresponding protein as a candidate target in view of its accumulation or disappearance. Retention of an intron in a coding sequence often results in the truncation of the native protein by introducing a stop codon within the reading frame (Varesco, L., et at., (1994), Hum. Genet., 93 (3): 281-286; Canton, H., et al., (1996), Mol. Pharmacol., 50 (4): 799-807; Ion, A., et al., (1996), Am. J. Hum. Genet., 58 (6): 1185-1191). Before such a stop codon is read, there generally occurs translation of a number of additional codons whereby a specific sequence is appended to the translated portion, which behaves as a protein marker of alternative splicing. These additional amino acids can be used to produce antibodies specific to the alternative form inherent to the pathological condition. These antibodies may subsequently be used as diagnostic tools. The truncated protein undergoes a change or even an alteration in properties. Thus enzymes may loose their catalytic or regulatory domain, becoming inactive or constitutively activated. Adaptors may lose their capacity to link different partners of a signal transduction cascade (Watanabe, K. et al., (1995), J. Biol. Chem., 270 (23): 13733-13739). Splicing products of receptors may lead to the formation of receptors having lost their ability to bind corresponding ligands (Nakajima, T. et al., (1996), Life Sci., 58 (9): 761-768) and may also generate soluble forms of receptor by release of their extracellular domain (Cheng J., (1994), Science, 263 (5154): 1759-1762). In this case, diagnostic tests can be designed, based on the presence of circulating soluble forms of receptor which bind a given ligand in different physiological fluids.

The invention is more specifically concerned with the use of the methods, nucleic acids or libraries described hereinabove for identifying antigenic domains that are specific for proteins involved in a pathology. The invention is equally directed to the use of the nucleic acids, proteins or peptides as described above for diagnosing pathological conditions.

The invention is equally directed to a method for identifying and/or producing proteins or protein domains involved in a pathology comprising:
  (a) hybridizing messenger RNAs of a pathological sample with cDNAs of a healthy sample, or vice versa, or both in parallel,
  (b) identifying, within the hybrids formed, regions corresponding to qualitative differences (unpaired (RNA) or paired (double stranded DNA)) which are specific to the pathological state in relation to the healthy state,
  (c) identifying and/or producing the protein or protein domain corresponding to one or several regions identified in step (b).

The regions so identified generally correspond to differential splicings, but they may also correspond to other genetic alterations such as insertion(s) or deletion(s), for example.

The protein(s) or protein domains may be isolated, sequenced, and used in therapeutic or diagnostic applications, notably for antibody production.

To better illustrate this point, the qualitative differential screening of the invention allows one to advantageously identify tumor suppressor genes. Indeed, may examples indicate that one way suppressor genes are inactivated in the course of tumor progression is inactivation by modulation of alternative forms of splicing.

Hence, in small cell lung carcinoma, the gene of protein p130 belonging to the RB family (retinoblastoma protein) is mutated at a consensus splicing site. This mutation results in the removal of exon 2 and in the absence of synthesis of the protein due to the presence of a premature stop codon. This observation was the first of its kind to underscore the importance of RB family members in tumorigenesis. Likewise, in certain non small cell lung cancers, the gene of protein p161NK4A, a protein which is an inhibitor of cyclin-dependent kinases cdk4 and cdk6, is mutated at a donor splicing site. This mutation results in the production of a truncated protein with a short half-life, leading to the accumulation of the inactive phosphorylated forms of RB. Furthermore, WT1, the Wilm's tumor suppressor gene, is transcribed into several messenger RNAs generated by alternative splicings. In breast cancers, the relative proportions of different variants are modified in comparison to healthy tissue, thereby yielding diagnostic tools or clues to understanding the importance of the various functional domains of WT1 in tumor progression. The same alteration process affecting ratios between different messenger RNA forms and protein isoforms during cellular transformation is again found in the case of neurofibrin NF1. In addition, the concept that modulation of splicing phenomena behaves as a marker of tumor progression is further supported by the example of HDM2 where five alternative splicing events are detected in ovarian and pancreatic carcinoma, the expression of which increases depending on the stage of tumor development. Furthermore, in head and neck cancers, one of the mechanisms by which p53 is inactivated involves a mutation at a consensus splicing site.

These few examples clearly illustrate the interest of the methods of the invention based on systematic screening for alternative splicing patterns which discriminate between a given tumor and an adjacent healthy tissue. Results thus obtained allow not only the characterization of known tumor suppressor genes but also, in view of the original and systematic aspect of qualitative differential screening methods, the identification of novel alternative splicings specific to tumors that are likely to affect new tumor suppressor genes.

The invention is therefore further directed to identifying and/or cloning tumor suppressor genes or genetic alterations (eg., splicing events) within those tumor suppressor genes, as previously defined. This method may advantageously comprise the following steps:
  (a) hybridizing messenger RNAs of a tumor sample with cDNAs of a healthy sample, or vice versa, or both in parallel,
  (b) identifying, within the hybrids formed, regions specific to the tumor sample in relation to the healthy sample, (c) identifying and/or cloning the protein or protein domain corresponding to one or more regions identified in step (b).

The tumor suppressor properties of the proteins or protein domains identified may then be tested in different known models. These proteins, or their native forms (displaying the splicing pattern observed in healthy tissue) may then be use for various therapeutic or diagnostic applications, notably for antitumoral gene therapy.

The present application therefore relates not only to different aspects of embodying the present technology but also to the exploitation of the resulting information in research, development of screening assays for chemical compounds of low molecular weight, and development of gene therapy or diagnostic tools.

In this connection, the invention further concerns the use of the methods, nucleic acids or libraries described above in genotoxicology, i.e. to predict the toxicity of test compounds.

The genetic programs initiated during treatment of cells or tissues by toxic agents are predominantly correlated with apoptotic processes, or programmed cell death. The importance of alternative splicing processes in regulating such apoptotic mechanisms is well described in the literature. However, no single gene engineering technique described to date allows exhaustive screening and isolation of sequence variations due to alternative splicings distinctive of two given pathophysiological conditions. The qualitative differential splicing screening methods developed by the present invention make it possible to gather all splicing differences occurring between two conditions within cDNA libraries. Comparing RNA sequences (for example messenger RNAs) of a tissue (or of a cell culture) either treated or not with a standard toxic compound allows the generation of cDNA libraries which comprise gene expression qualitative differences characterizing the toxic effect being investigated. These cDNA libraries may then be hybridized with probes derived from RNA arising from the same tissues or cells treated with the chemical being assessed for toxicity. The relative capacity of these probes to hybridize with the genetic sequences specific to a given standard toxic condition allows toxicity of the compound to be determined. Furthermore, in addition to the use of DATAS for the generation and utilization of qualitative differential libraries induced by toxic agents, a part of the invention consists equally in demonstrating that regulation defects in the splicing of certain messenger RNAs may be induced by certain toxic agents, at doses lower than the IC50 determined in the cytotoxicity and apoptosis tests known to those skilled in the art. Such regulation defects (or deregulations) may be used as markers to assess the toxicity and/or potency of molecules (chemical or genetic).

The invention therefore equally concerns any method for detecting or monitoring the toxicity and/or therapeutic potential of a compound based on the detection of splicing forms and/or patterns induced by this compound on a biological sample. It further concerns the use of any modification of splicing forms and/or patterns as a marker to assess the toxicity and/or potency of molecules.

Toxicity assessment or monitoring may be performed more specifically following two approaches:

According to a first approach, the qualitative differential screening may be accomplished between a reference tissue or cell culture not subjected to treatment on the one hand, and treated by the product whose toxicity is to be assessed on the other hand. The analysis of clones representative of qualitative differences specifically induced by this product subsequently provides for the eventual detection within these clones of events closely related to cDNA involved in toxic reactions such as apoptosis.

Such markers are monitored as they arise as a function of the dose and duration of treatment by the product in question so that the toxicological profile thereof may be established.

The present application is therefore equally directed to a method for identifying, by means of qualitative differential screening according to the methods set forth above, toxicity markers induced in a model biological system by a chemical compound whose toxicity is to be measured. In this respect, the invention relates in particular to a method for identifying and/or cloning nucleic acids specific of a toxic state of a given biological sample comprising preparing qualitative differential libraries between the cDNAs and the RNAs of the sample either subjected or not to treatment by the test toxic compound, and searching for toxicity markers specific to the properties of the sample post-treatment.

According to the second approach, abacus are prepared for different classes of toxic products, that are fully representative of the toxicity profiles as a function of dosage and treatment duration for a given reference tissue or cell model. For each abacus dot, cDNA libraries representative of qualitative genetic differences can be generated. The latter represent qualitative differential libraries, i.e. they are obtained by extracting genetic information from the dot selected in the abacus diagram and from the corresponding dot in the control tissue or cell model. As set forth in the examples, the qualitative differential screening is based on hybridizing mRNA derived from one condition with cDNAs derived from another condition. As noted above, the qualitative differential screening may also be conducted using total RNAs or nuclear RNAs containing premessenger species.

In this respect, the invention concerns a method for determining or assessing the toxicity of a test compound to a given biological sample comprising hybridizing:
differential libraries between cDNAs and RNAs of said biological sample from a healthy state and at various stages of toxicity resulting from treatment of said sample with a reference toxic compound, with,
a nucleic acid preparation of the biological sample treated by said test compound, and
assessing the toxicity of the test compound by determining the extent of hybridization with the different libraries.

According to this method, it is advantageous to proceed with two cross hybridizations for each condition (compound dosage and/or incubation time), between:
RNAs from condition A (test) and cDNAs from condition B (reference) (rA/cB)
RNAs from condition B (reference) and cDNAs from condition A (test) (rB/cA).

Each reference toxic condition, at each abacus dot, thus corresponds to two qualitative differential screening libraries. One of such libraries is a full collection of qualitative differences, i.e. notably the alternative splicing events, specific to the normal reference condition whereas the other library is a full collection of splicing events specific to the toxic situations. These libraries are replica-plated on solid support materials such as nylon or nitrocellulose filters or advantageously on chips. These libraries initially formed of cDNA fragments of variable length (according to the splicing events being considered) may be optimized by using oligonucleotides derived from previously isolated sequences.

Where a chemical compound is a candidate for pharmaceutical development, this may be tested with the same tissue or cell models as those recorded in the toxicity abacus diagram. Molecular probes may then be synthesized from mRNAs extracted from the biological samples treated with the chemical compound of interest. These probes are then hybridized on filters bearing cDNA of rA/cB and rB/cA libraries. For instance, the rA/cB library may contain sequences specific to the normal condition and the rB/cA library may contain alternative spliced species specific to the toxic condition. Innocuity or toxicity of the chemical compound is then readily assessed by examining the hybridization profile of an mRNA-derived probe belonging to the reference tissue or cell model that has been treated by the test compound:

efficient hybridization with the rA/cB library and no signal in the rB/cA library demonstrates that the compound has no toxicity in the model under study positive hybridization between the probe and the rB/cA library clones is evidence of test compound-induced toxicity.

Practical applications related to such libraries may be provided by hepatocyte culture models, such as the HepG2 line, renal epithelial cells, such as the HK-2 line, or endothelial cells, such as the ECV304 line, following treatment by toxic agents such as ethanol, camptothecin or PMA.

A preferred example may be provided by use in cosmetic testing of skin culture models subjected or not to treatment by toxic agents or irritants.

A further object of the present application is therefore differential screening libraries (between cDNAs and RNAs) made from reference organs, tissues or cell cultures treated by chemical compounds representative of broad classes of toxic agents according to abacus charts disclosed in the literature. The invention further encompasses the spreading of these libraries on filters or support materials known to those skilled in the art (nitrocellulose, nylon . . . ). Advantageously, these support materials may be chips which hence define genotoxicity chips. The invention is further concerned with the potential exploitation of the sequencing data about different clones making up these libraries in order to understand the mechanisms underlying the action of various toxic agents, as well as with the use of such libraries in hybridization with probes derived from cells or tissues treated by a chemical compound or a pharmaceutical product whose toxicity is to be determined. Advantageously, the invention relates to nucleic acid libraries such as of the type defined above, prepared from skin cells treated under different toxic conditions. The invention is further concerned with a kit comprising these individual skin differential libraries.

The invention is further directed to the use of the methods, nucleic acids or libraries previously described to assess (predict) or enhance the therapeutic effectiveness of test compounds (genopharmacology).

In this particular use, the underlying principle is very similar to that previously described. Reference differential libraries are established between cDNAs and RNA from a control cell culture of organ and counterparts thereof simulating a pathological model. The therapeutic efficacy of a product may then be evaluated by monitoring its potential to antagonize qualitative variations of gene expression which are specific of the pathological model. This is demonstrated by a change in the hybridization profile of a probe derived from the pathological model with the reference libraries: in the absence of treatment, the probe only hybridizes with the library containing the specific markers of the disease. Following treatment with an effective product, the probe, though it is derived from the pathological model, hybridizes preferentially with the other library, which bears the markers of the healthy model equivalent.

In this respect, the model is further directed to a method for determining or assessing the therapeutic efficacy of a test compound on a given biological sample comprising hybridizing:

differential libraries between cDNAs and RNAs from said biological sample in a healthy state and in a pathological state (at different development stages), with, a preparation of nucleic acids derived from the biological sample treated by said test compound, and assessing the therapeutic potential of the test compound by determining the extent of hybridization with the different libraries.

Such an application is exemplified by an apoptosis model simulating certain aspects of neurodegeneration which are antagonized by standard trophic factors. Thus, cells derived from the PC12 pheochromocytoma line which differentiate into neurites in the presence of NGF enter into apoptosis upon removal of this growth factor. This apoptotic process is accompanied by expression of many programmed cell death markers, several of which are regulated by alternative splicing and downregulated by IGF1. Two libraries derived from qualitative differential screening are generated from mRNA extracts of differentiated PC12 cells in the process of apoptosis following NGF removal on the one hand and from differentiated PC12 cells prevented from undergoing apoptosis by supplementing IGF-1 on the other hand. To these libraries, may be hybridized probes prepared from mRNA derived from differentiated PC12 in the process of apoptosis and whose survival is enhanced by treatment with a neuroprotective product to be tested. The efficiency of the test compound to reverse the qualitative characteristics can thus be appreciated by monitoring the capacity of the probe to selectively hybridize to those specific library clones representing cells having a better survival rate. This test could be subsequently used to test the efficiency of derivatives of such a compound or any other novel family of neuroprotective compounds and to improve the pharmacological profile thereof.

In a specific embodiment, the method of the invention allows one to assess the efficacy of a neuroprotective test compound by carrying out hybridization with a differential library according to the invention derived from a healthy nerve cell and this neurodegenerative model cell.

In another embodiment, one is interested in testing an antitumor compound using differential libraries established from tumor and healthy cell samples.

As already noted, the method of the invention could furthermore be used to improve the properties of a compound, by testing the capacity of various derivatives thereof to induce a hybridization profile similar to that of the library representative of the healthy sample.

The invention is further directed to the use of the methods, nucleic acids or libraries described hereinabove in pharmacogenomics, i.e. to assess (predict) the response of a patient to a test compound or treatment.

Pharmacogenomics is aimed at establishing genetic profiles of patients with a view to determine which treatment would reasonably be successful for a given pathology. The techniques described in the present invention make it possible in this respect to establish cDNA libraries that are representative of qualitative differences occurring between a pathological condition which is responsive to a given treatment and another condition which is unresponsive or poorly responsive thereto, and thus may qualify for a different therapeutic strategy. Once these standard libraries are established, they can be hybridized with probes prepared from the patients messenger RNAs. The hybridization results allow one to determine which patient has a hybridization profile corresponding to the responsive or non responsive condition and thus refine treatment choice in patient management.

In this application, the purpose is on the one hand to suggest depending on the patient's history the most appropriate treatment regimen likely to be successful and on the other hand to enroll in a given treatment regimen those patients most likely to benefit therefrom. As with other applications, two qualitative differential screening libraries are prepared: one based on a pathological model or sample known to respond to a given treatment, and another based on a further pathological model or sample which is poorly responsive or unresponsive to therapy. These two libraries are then hybridized with probes derived from mRNAs extracted from biopsy tissues of individual patients. Depending on whether such probes preferentially hybridize with the alternatively spliced forms specific to one particular condition, the patients may be divided into responsive and unresponsive subjects to the standard treatment which initially served to define the models.

In this respect, the invention is also directed to a method for determining or assessing the response of a patient to a test compound or treatment comprising hybridizing:
- differential libraries between cDNAs and RNAs from a biological sample responsive to said compound/treatment and from a biological sample which is poorly responsive or unresponsive to said compound/treatment, with,
- a nucleic acid preparation derived from a pathological biological sample of the patient, and
- assessing the responsiveness of the patient by determining the extent of hybridization with the different libraries.

A preferred example of the usefulness of qualitative differential screening in pharmacogenomics is illustrated by a qualitative differential screening between two tumors of the same histological origin, one of which showing regression when treated with an antitumor compound (for example transfer of cDNA coding for wild type p53 protein by gene therapy), while the other being unresponsive to such treatment. The first benefit derived from constructing qualitative differential libraries between these two conditions is the ability to determine, by analyzing clones making up these libraries, which molecular mechanisms are elicited during regression as observed in the first model and absent in the second.

Subsequently, the use of filters or any other support material bearing cDNAs derived from these libraries allows one to conduct hybridization with probes derived from mRNAs of tumor biopsies whose response to said treatment is to be predicted. It is possible by looking at the results to assign patients to an optimized treatment regimen.

One particular example of this method consists in determining the tumor response to p53 tumor suppressor gene therapy. It has indeed been reported that certain patients and certain tumors respond more or less to this type of treatment (Roth et al., (1995) Nature Medicine, 2: 958). It is therefore essential to be able to determine which types of tumors and/or which patients are sensitive to wild type p53 gene therapy, in order to optimize treatment and make the best choice regarding the enrollment of patients in clinical trials being undertaken. Advantageously, the method of the invention makes it possible to simplify the procedure by providing libraries specific to qualitative characteristics of p53-responsive cells and non responsive cells. Examples of cell models sensitive or resistant to p53 are described for instance by Sabbatini et al. (Genes Dev., (1995), 9: 2184) or by Roemer et al. (Oncogene, (1996), 12: 2069). Hybridization of these libraries with probes derived from patients' biopsy samples will make assessment of patient responsiveness easier. In addition, the specific libraries will allow identification of nucleic acids involved in p53 responsiveness.

The present application is therefore also directed to the establishment of differential screening libraries from pathological samples, or pathological models, which vary in responsiveness to at least one pharmacological agent. These libraries can be restricted, complex or autologous libraries as defined supra. It is also concerned with the spreading of these libraries upon filters or support materials known to those skilled in the art (nitrocellulose, nylon . . . ). In an advantageous manner, these support materials may be chips which thus define pharmacogenomic chips. The invention further relates to the potential exploitation of sequencing data of different clones forming such libraries with a view to elucidate the mechanisms which lead the pathological samples to respond differently to various treatments, as well as to the use of such libraries for conducting hybridization with probes derived from biopsy tissue originating from pathological conditions one wishes to predict the response to the standard treatment initially used to define those libraries.

The present invention thus describes that variations in splicing forms and/or patterns represent sources of pharmacogenomic markers, i.e. sources of markers by which to determine the capacity of and the manner in which a patient will respond to treatments. In this respect, the invention is thus further directed to the use of inter-individual variability in the isoforms generated by alternative splicing (spliceosome analysis) as a source of pharmacogenomic markers. The invention also concerns the use of splicing modifications induced by treatments as a source of pharmacogenomic markers. Thus, as explained hereinabove, the DATAS methods of the invention make it possible to generate nucleic acids representative of qualitative differences occurring between two biological samples. Such nucleic acids, or derivatives thereof (probes, primers, complementary acids, etc.) may be used to analyze the spliceosome of subjects, with a view to demonstrating their capacity and manner of responding to treatments, or their predisposition to a given treatment/pathology, etc.

These various general examples illustrate the usefulness of qualitative differential screening libraries in studies of genotoxicity, genopharmacology and pharmacogenomics as well as in research on potential diagnostic or therapeutic targets. Such libraries are derived from cloning the qualitative differences occurring between two pathophysiological situations. Since another use of the cDNAs representative of these qualitative differences is to generate probes designed to screen a genomic DNA library whose characteristics are described hereinabove, such an approach may also be implemented for any study of genotoxicity, genopharmacology and pharmacogenomics as well as for gene identification. In genotoxicity studies for instance, genomic clones statistically restricted by the size of their insertions to a single intron or to a single exon are arranged on fitters according to their hybridization with DATAS probes derived from qualitative differential analysis between a reference cell or tissue sample and the same cells or tissues treated by a reference toxic compound. Once such clones representative of different classes of toxicity are selected, they can then be hybridized with a probe derived from total messenger RNAs of a same cell population or a same tissue sample treated by a compound whose toxicity is to be assessed.

Figure 7:
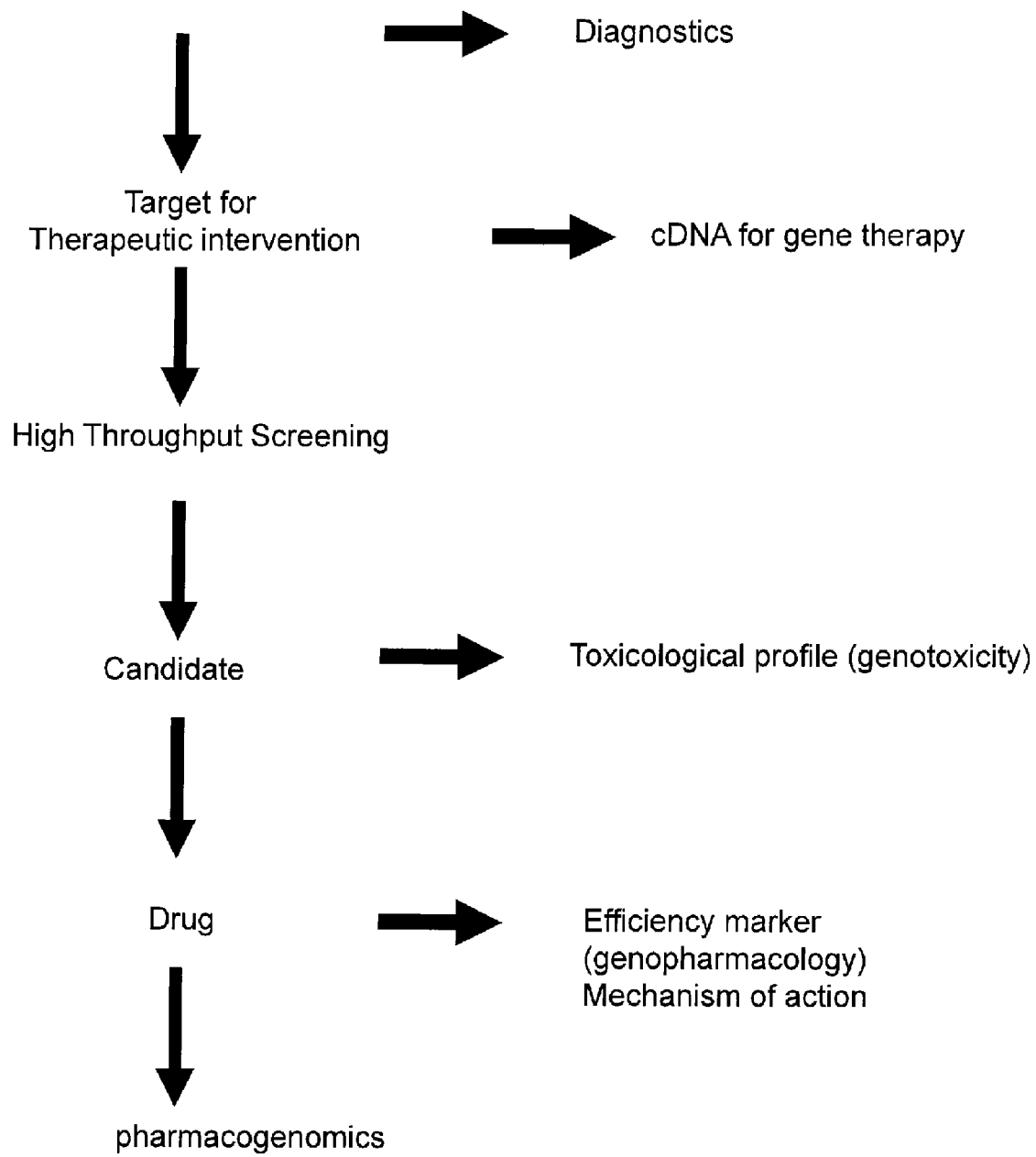

Other advantages and practical applications of the present invention will become more apparent from the following examples which are given for purposes of illustration and not by way of limitation. The fields of application of the invention are shown in FIG. 7.

LEGENDS TO FIGURES

FIG. 1. Schematic representation of differential screening assays according to the invention (FIG. 1A) using one (FIG. 1B) or two (FIG. 1C) hybridization procedures, and use of nucleic acids (FIG. 1D).

FIG. 2. Schematic representation of the production of RNA/DNA hybrids allowing characterization of single stranded RNA sequences, specific markers of the pathological or healthy state.

FIG. 3. Schematic representation of a method for isolating and characterizing by sequencing single stranded RNA sequences specific to a pathological or healthy, condition.

FIG. 4. Schematic representation of another means for characterizing by sequencing all or part of the single stranded RNAs specific to a pathological or healthy condition.

FIG. 5. Schematic representation of the isolation of alternatively spliced products based on R-loop structures.

Figure 6B:
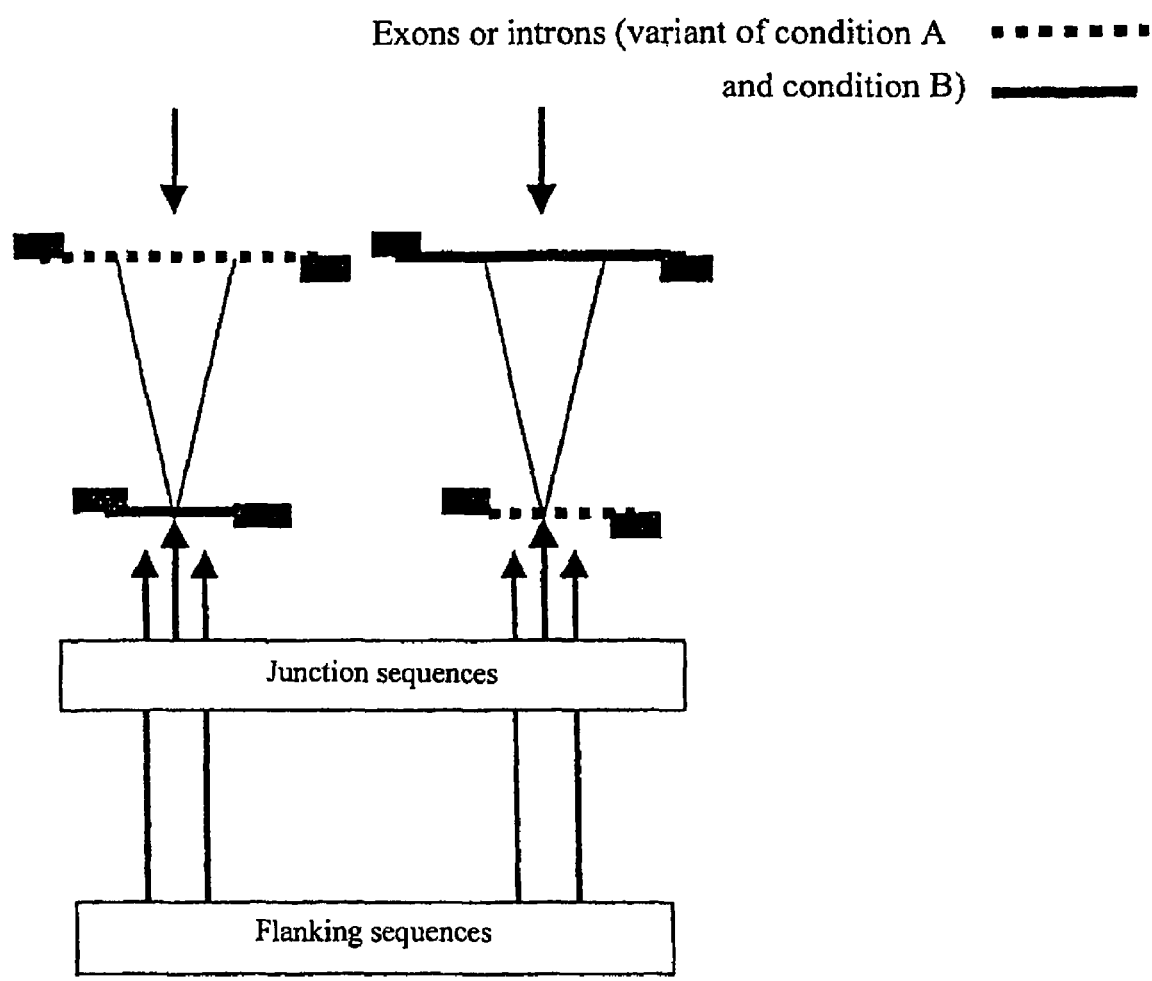

FIG. 6. Schematic representation of qualitative differential screening by loop restriction (formation of ds cDNA/cDNA homoduplexes and extraction of data, FIG. 6A) and description of the data obtained (FIG. 6B).

FIG. 7. Benefits of qualitative differential screening at different stages of pharmaceutical research and development.

FIG. 8. Isolation of a differentially spliced domain in the grb2/grb33 model. A) Production of synthetic grb2 and grb33 RNAs. B) Description of the first steps of DATAS leading to characterization of an RNA fragment corresponding to a differentially spliced domain; 1: grb2 RNA, 2: Hybridization between grb2 RNA and grb33 cDNA, 3: Hybridization between grb2 RNA and grb2 cDNA, 4: Hybridization between grb2 RNA and water, 5: Supernatant after passage of (2) on streptavidin beads, 6: Supernatant after passage of (3) on streptavidin beads, 7: Supernatant after passage of (4) on streptavidin beads, 8: RNase H digestion of grb2 RNA/grb33 cDNA duplex, 9: RNase H digestion of grb2 RNA/grb2 cDNA duplex, 10: RNase H digestion of grb2 RNA, 11: same as (8) after passage on an exclusion column, 12: same as (9) after passage on an exclusion column, 13: same as (10) after passage on an exclusion column.

Figure 9:
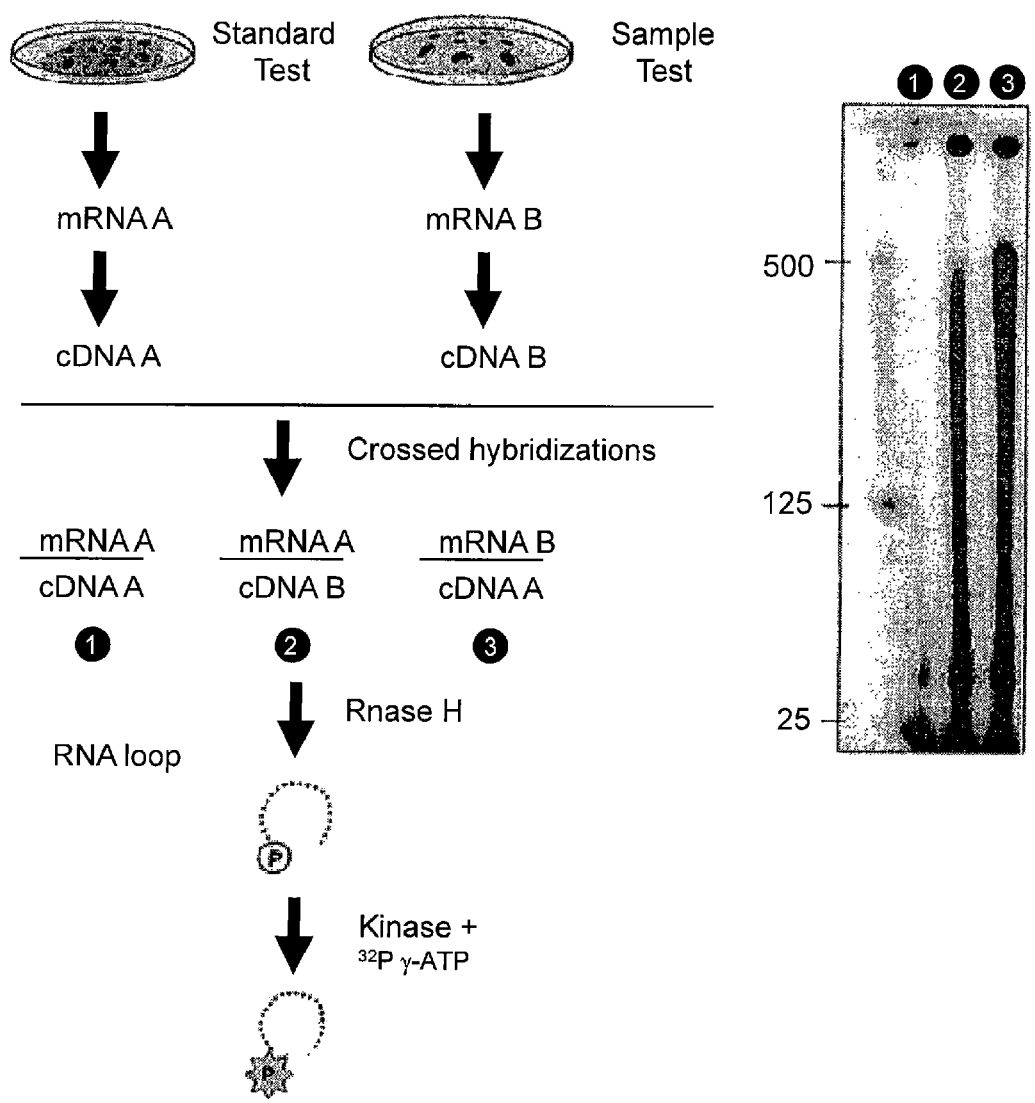

FIG. 9. Representation of unpaired RNAs derived from RNase H digestion of RNA/single stranded cDNA duplexes originating from HepG2 cells treated or not by ethanol.

Figure 10:
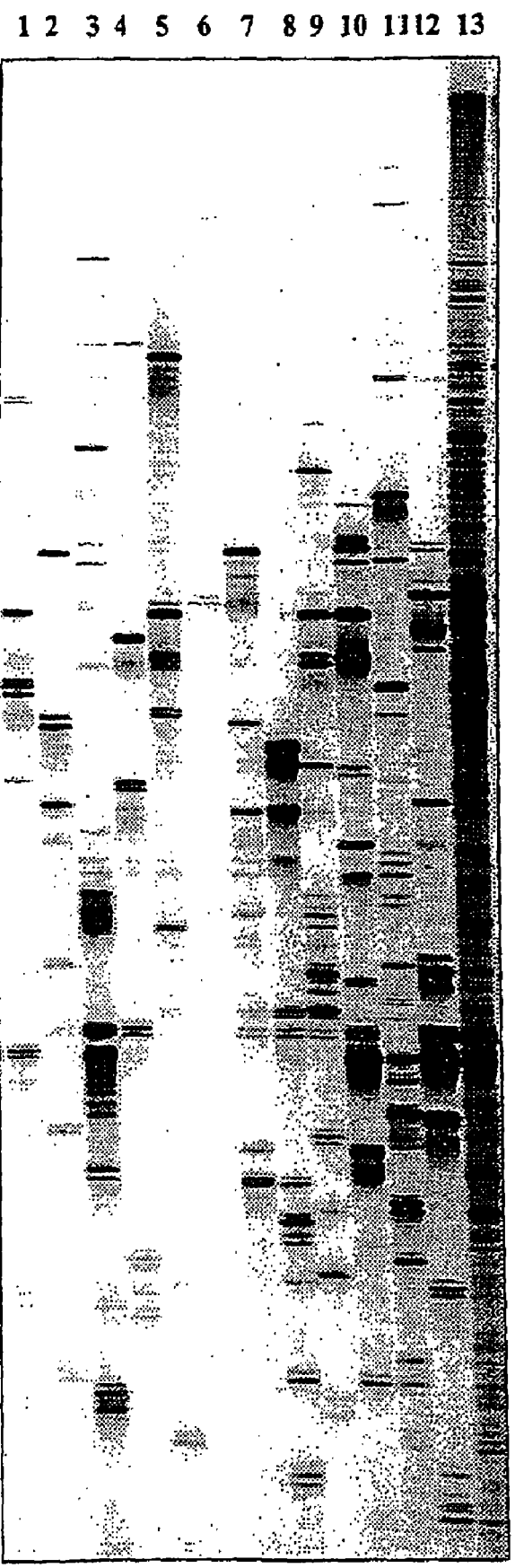

FIG. 10. Representation of double stranded cDNAs generated by one of the DATAS variants. 1 to 12: PCR on RNA loop populations derived from RNase H digestion, 13: PCR on total cDNA.

FIG. 11. Application of the DATAS variant involving double stranded cDNA in the grb2/grb33 model. A) Agarose gel analysis of the complexes following hybridization: 1: double stranded grb2 cDNA/grb33 RNA, 2: double stranded grb2 cDNA/grb2 RNA, 3: double stranded grb2 cDNA/water. B) Digestion of samples 1, 2 and 3 in (A) by nuclease S1 and mung bean nuclease: 1 to 3: complexes 1 to 3 before glyoxal treatment; 4 to 6: complexes 1 to 3 after glyoxal treatment; 7 to 9: Nuclease S1 digestion of 1 to 3; 10 to 12: Mung bean nuclease digestion of 1 to 3.

FIG. 12. Application of the DATAS variant involving single stranded cDNA and RNase H in a HepG2 cell system treated or not with 0.1 M ethanol for 18 hours. Cloned inserts were transferred to a membrane after agarose gel electrophoresis and hybridized with probes corresponding to the treated (Tr) and untreated (NT) conditions.

Figure 13:
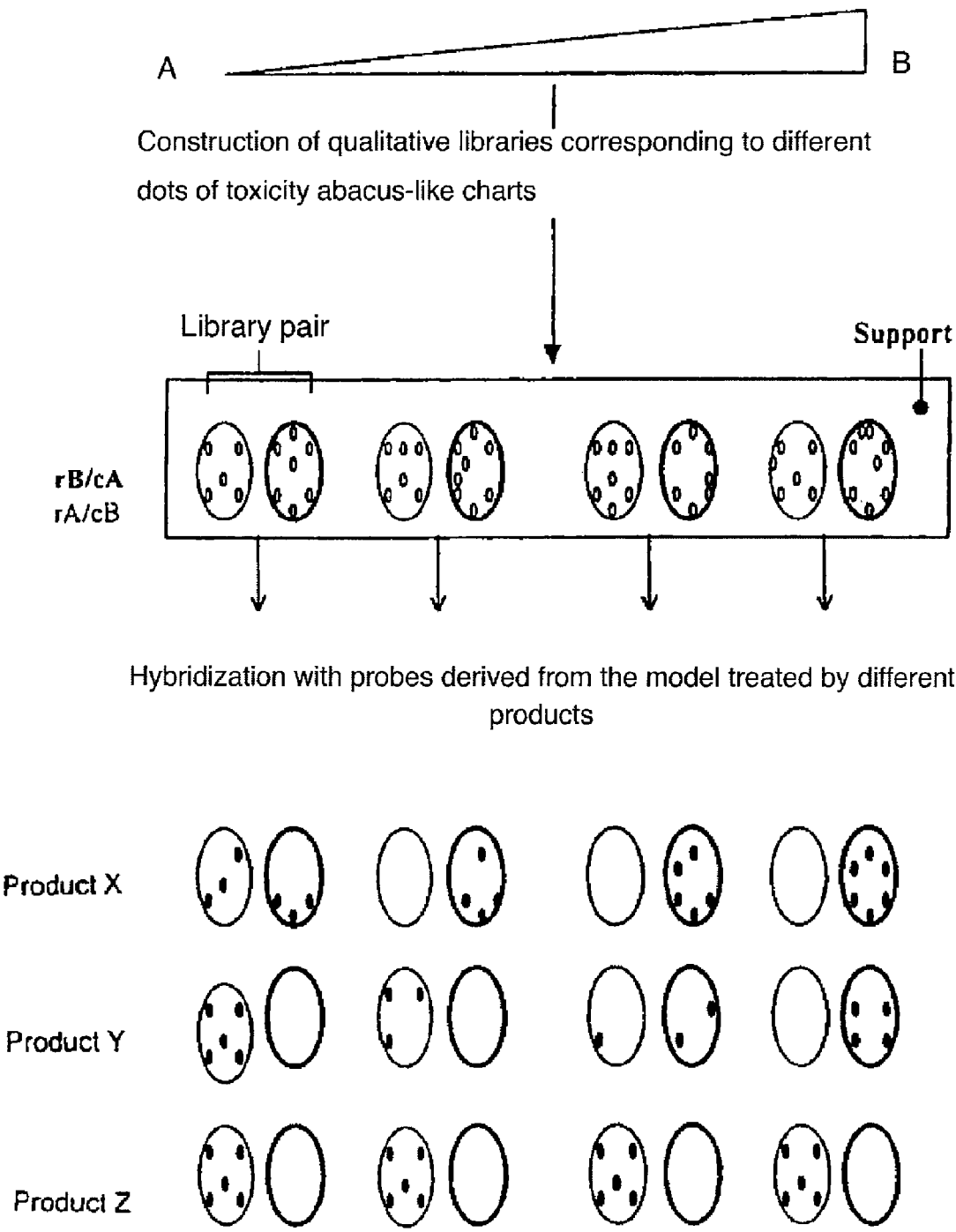

FIG. 13. Experimental procedure for assessing the toxicity of a product.

Figure 14:
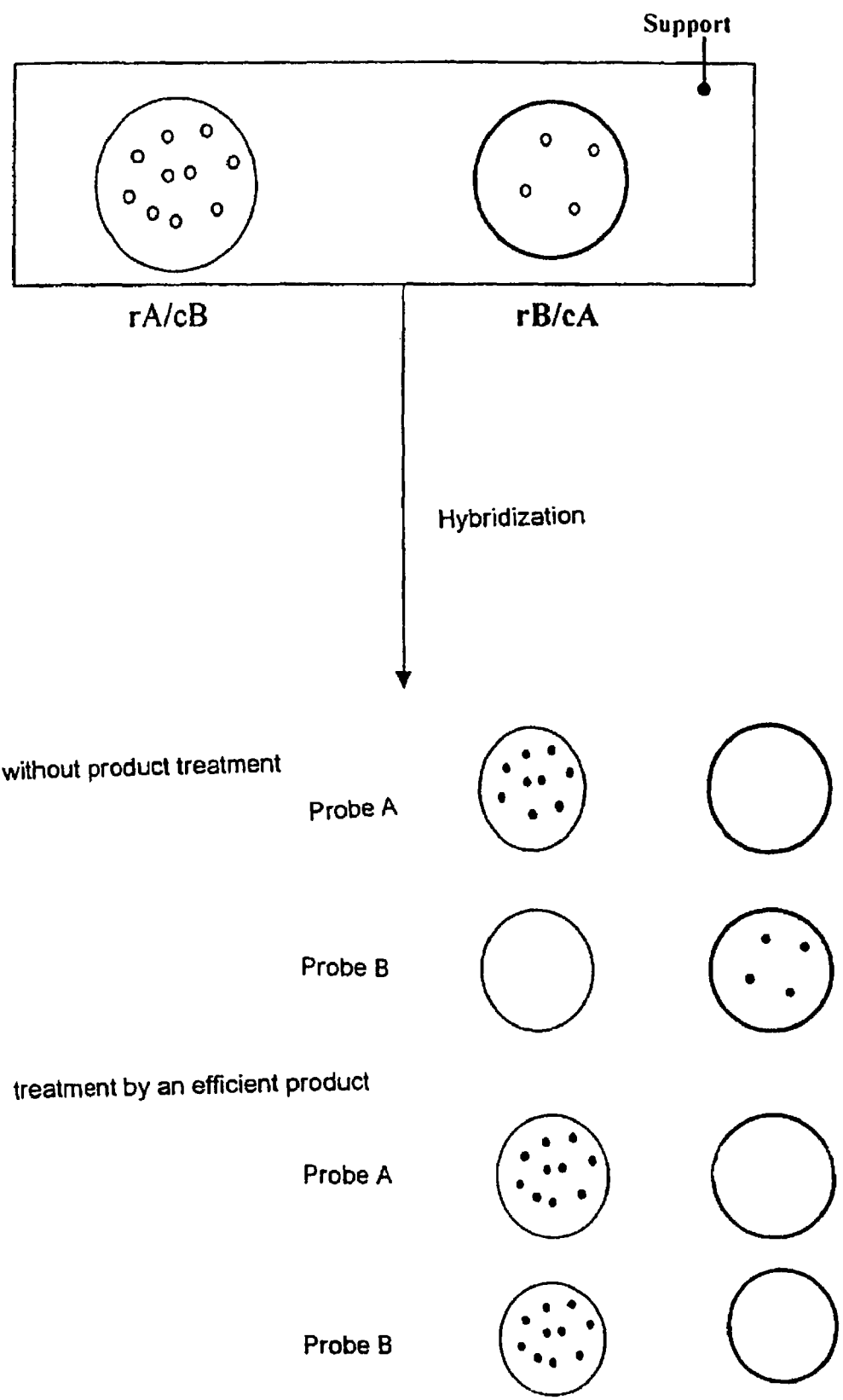

FIG. 14. Experimental procedure for monitoring the efficacy of a product.

FIG. 15. Experimental procedure for investigating the sensitivity of a pathological condition to a treatment.

Figure 16:
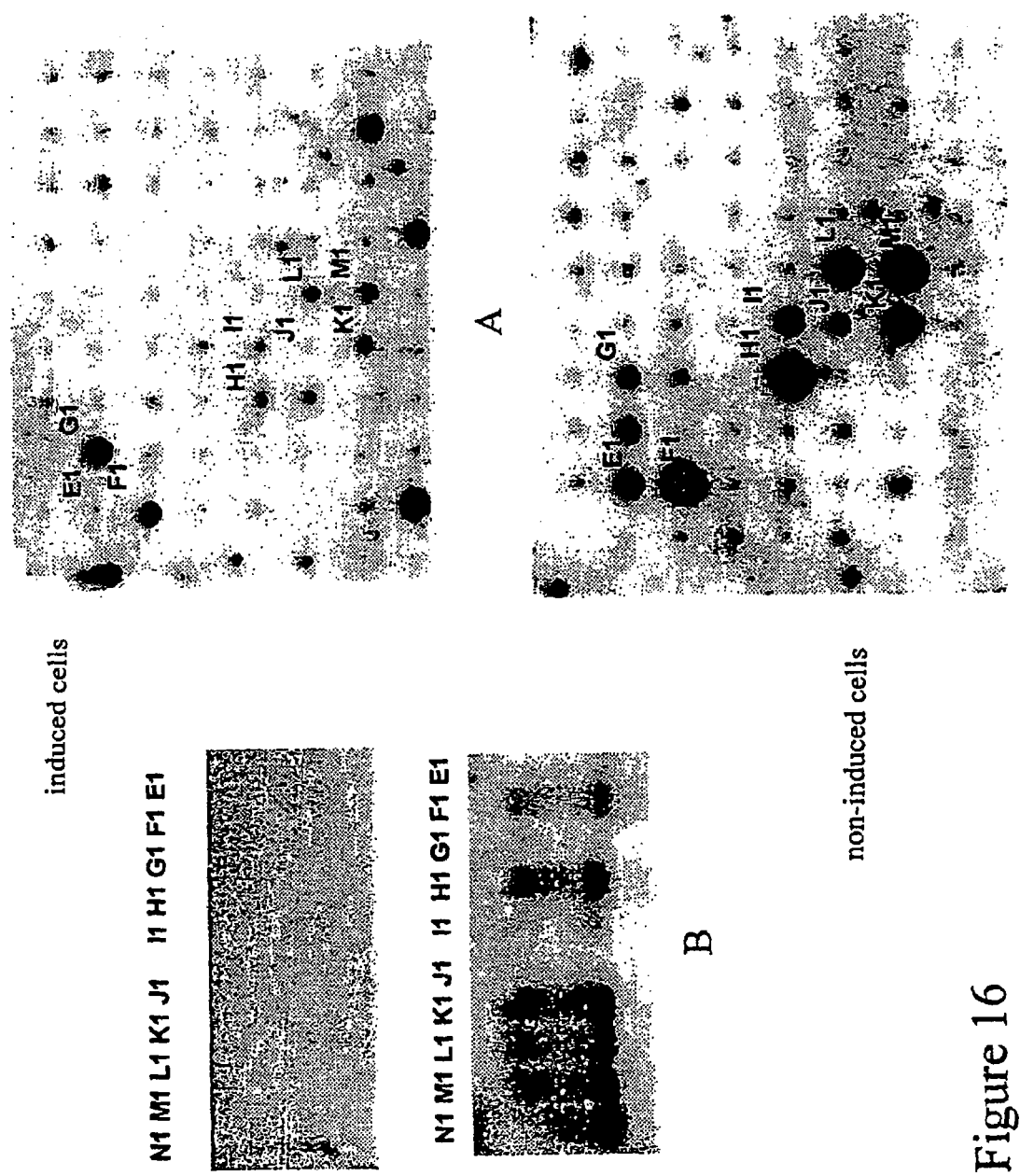

FIG. 16. Analysis of differential hybridization of clones derived from DATAS using RNAs from induced cells and cDNAs from non-induced cells. A) Use of bacterial colonies deposited and lysed on a membrane. B) Southern blot on a selection of clones from A.

FIG. 17. Nucleotide and peptide sequence of ΔSHC (SEQ ID NO: 9 and 10).

Figure 18C:
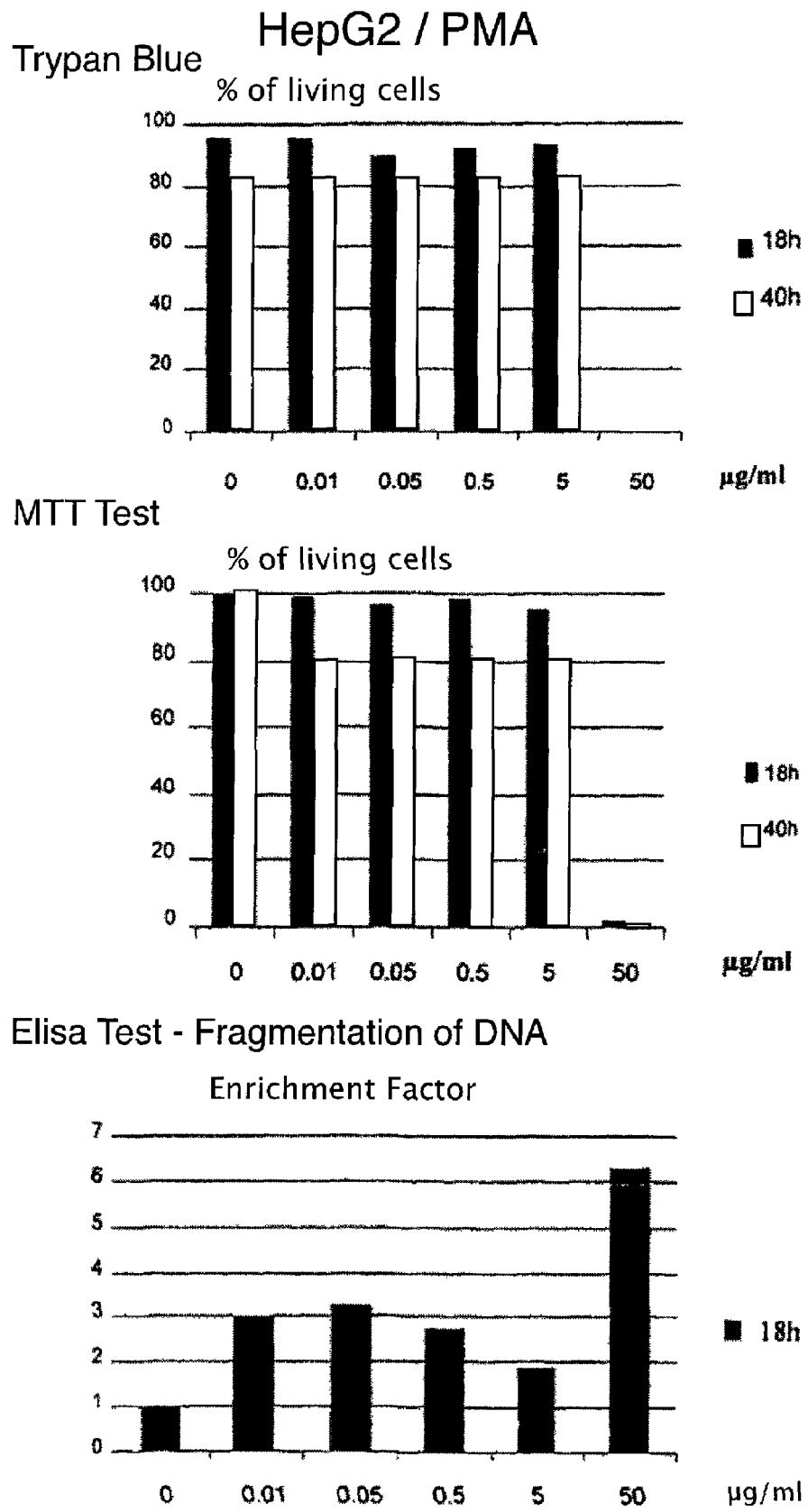

FIG. 18. Cytotoxicity and apoptosis tests on HepG2 cells treated with A) ethanol; B) camptothecin; C) PMA.

FIG. 19. RT-PCR reactions using RNAs derived from HepG2 cells treated or not (NT) with ethanol (Eth.), camptothecin (Camp.) and PMA (PMA) allowing amplification of the fragments corresponding to MACH-a, BCL-X, FASR domains and using beta-actin as normalization control.

In the examples and the description of the invention, reference is made to sequences from the List of Sequences, which contains the following free text:

<223> OLIGO
<223> OLIGO
<223> OLIGO
<223> OLIGO
<223> OLIGO
<223> OLIGO
<223> OLIGO
<223> OLIGO
<223> OLIGO
<223> OLIGO
<223> OLIGO
<223> OLIGO

EXAMPLES

1. Differential Cloning of Alternative Splicings and Other Qualitative Modifications in RNAs Using Single Stranded cDNAs Messenger RNAs corresponding to two conditions, one being normal (mN) and the other being of a pathological origin (mP), are isolated from biopsy samples or cultured cells. These messenger RNAs are converted into complementary DNAs (cN) and (cP) by means of reverse transcriptase (RT). mN/cP and cN/mP hybrids are then prepared in a liquid phase (see the diagram of FIG. 2 illustrating one of either cases leading to the formation of cN/mP).

These hybrids are advantageously prepared in phenol emulsion (PERT technique or Phenol Emulsion DNA Reassociation Technique) continuously subjected to thermocycling (Miller, R., D. and Riblet, R., (1995), Nucleic Acids Research, 23 (12): 2339-2340). Typically, this hybridization is executed using between 0.1 and 1 µg of polyA+ RNA and 0.1 to 2 µg of complementary DNA in an emulsion formed of an aqueous phase (120 mM sodium phosphate buffer, 2.5 M NaCl, 10 mM EDTA) and an organic phase representing 8% of the aqueous phase and formed of twice distilled phenol.

Another method is also advantageously employed to obtain the heteroduplexes: after the reverse transcription reaction, the newly synthesized cDNA is separated from the biotinylated oligodT primer by exclusion chromatography. 0.1 to 2 µg of this cDNA is coprecipitated with 0.1 to 1 µg of polyA+ RNA in the presence of 0.3 M sodium acetate and two volumes of ethanol. These coprecipitated nucleic acids are taken up in 30 µl of a hybridization buffer composed of 80% formamide, 40 mM PIPES (piperazinebis(2-ethanesulfonic acid)) pH 6.4, 0.4 M NaCl and 1 mM EDTA.

The nucleic acids in solution are heat-denatured at 85° C. for 10 min and hybridization is then carried out at 40° C. for at least 16 h and up to 48 h.

The advantage of the formamide hybridization procedure is that it provides more highly selective conditions for cDNA and RNA strand pairing.

As a result of these two hybridization techniques there is obtained an RNA/DNA heteroduplex the base pairing extent of which depends on the ability of RT to synthesize the entire cDNA. Other single stranded structures observed are RNA (and DNA) regions corresponding to alternative splicings which distinguish the two pathophysiological states under study.

The method is then aimed at characterizing the genetic information borne by such splice loops.

To this end, the heteroduplexes are purified by capture of cDNAs (primed with biotinylated oligo-dT) by means of streptavidin-coated beads. Advantageously these beads are beads having magnetic properties, allowing them to be separated from RNAs not engaged in the heteroduplex structures by the action of a magnetic separator. Such beads and such separators are commercially available.

At this stage of the procedure are isolated heteroduplexes and cDNAs not engaged in hybridization with RNAs. This material is then subjected to the action of RNase H which will selectively hydrolyze regions of RNA hybridized with cDNAs. The products of this hydrolysis are on the one hand cDNAs and on the other hand, RNA fragments which correspond to splice loops or non hybridized regions as a result of incomplete reverse transcriptase reaction. The RNA fragments are separated from DNA by magnetic separation according to the same experimental procedure as set forth above and by digestion with DNase free of contaminating RNase activity.

1.1. Validation of the DATAS Method on Splicing Variants of the Grb2 Gene

The feasibility of this approach was demonstrated in an in vitro system using RNA corresponding to the coding region of Grb2 on the one hand and single stranded cDNA complementary to the coding region of Grb3.3. The Grb2 gene has an open reading frame of 651 base pairs. Grb33 is an isoform of grb2 generated by alternative splicing and comprising a deletion of 121 base pairs in the SH2 functional domain of grb2 (Fath et al., (1994), Science 264: 971-4). Grb2 and Grb33 RNAs are synthesized by methods known to those skilled in the art from a plasmid harboring the Grb2 or Grb33 coding sequence driven by the T7 promoter by means of the RiboMax kit (Promega). Analysis of the products shows that the synthesis is homogeneous (FIG. 8A). For purposes of visualization, Grb2 RNA was also radiolabeled by incorporation of a labeled base during in vitro transcription by means of the RiboProbe kit (Promega). Grb2 and Grb33 cDNAs were synthesized by reverse transcription from the above-obtained synthetic RNA products, using the Superscript II kit (Life Technologies) and a biotinylated oligonucleotide primer common to Grb2 and Grb33 corresponding to the complement of the Grb2 sequence (618-639). RNAs and cDNAs were treated according to the suppliers' instructions (Promega, Life Technologies), purified on an exclusion column (RNase-free Sephadex G25 or G50, 5 Prime, 3 Prime) and quantified by spectrophotometry.

The first steps of DATAS were executed by combining in suspension 10 ng of labeled Grb2 RNA with:
1. 100 ng of biotinylated grb33 cDNA,
2. 100 ng of biotinylated grb2 cDNA,
3: water in 30 µl of a hybridization buffer containing 80% formamide, 40 mM PIPES (pH 6.4), 0.4 M NaCl, 1 mM EDTA. The nucleic acids are denatured by heating for 10 min at 85° C., after which the hybridization is carried out for 16 hours at 40° C. After capture on streptavidin beads, the samples are treated with RNase H as described hereinabove.

These steps are analyzed by electrophoresis on a 6% acrylamide gel followed by processing of the gels with an Instant Imager (Packard instruments) which allows the qualification and quantification of the species derived from labeled grb2 RNA (FIG. 8B). Thus, lanes 2, 3 and 4 show that grb2/grb33 and grb2/grb2 duplexes are formed quantitatively. Migration of the grb2/grb33 complex is slower relative to that of grb2 RNA (lane 2) while that of the grb2/grb2 complex is faster (lane 3). Lanes 5, 6 and 7 correspond to samples not retained by the streptavidin beads showing that 80% of grb2/grb33 and grb2/grb2 complexes were captured by the beads whereas non-biotinylated grb2 RNA alone was found solely in the bead supernatant. Treatment with RNase H releases, in addition to free nucleotides which migrate faster than bromophenol blue (BPB), a species that migrates below xylene cyanol blue (XC) (indicated by an arrow in the figure) and this, specifically in lane 8 corresponding to the grb2/grb33 complex relative to lanes 9 and 10 which correspond to the grb2/grb2 complex and to grb2 RNA. Lanes 11, 12 and 13 correspond to lanes 8, 9 and 10 after passage of the samples through an exclusion column to remove free nucleotides. The migration observed in lanes 8 and 11 is that expected for an RNA molecule corresponding to the 121-nucleotide deletion that distinguishes grb2 from grb33.

This result clearly shows that it is possible to obtain RNA loops generated by the formation of heteroduplexes between two sequences derived from two splicing isoforms.

1.2. Application of the DATAS Method to Generate Qualitative Libraries of Hepatic Cells in a Healthy and Toxic State A more complex situation was examined. Within the scope of the application of DATAS technology as a tool to predict the toxicity of molecules, the human hepatocyte cell line HepG2 was treated with 0.1 M ethanol for 18 hours. RNAs were extracted from cells that were or were not subjected to treatment. The aforementioned DATAS variant (preparation of biotinylated ss cDNA, cross hybridizations in liquid phase, application of a magnetic field to separate the species, RNase H digestion) was effected with untreated cells in the reference condition (or condition A) and with treated cells in the test condition (or condition B) (FIG. 9). As the extracted RNAs were not radiolabeled, the RNAs generated by RNase H digestion were visualized by carrying out an exchange reaction to replace the RNA 5' phosphate with a labeled phosphate, by means of T4 polynucleotide kinase and gamma-$P^{32}$ATP. These labeled products were then loaded on an acrylamide/urea gel and analyzed by exposure using an Instant Imager (Packard Instruments). Complex signatures derived from A/B and B/A hybridizations could then be visualized with a first group of signals migrating slowly in the gel and corresponding to large nucleic acid sequences and a second group of signals migrating between 25 and 500 nucleotides. These signatures are of much lower intensity in condition A/A, suggesting that ethanol can induce a reprogramming of RNA splicing events, manifested as the presence of A/B and B/A signals.

1.3. Cloning and Preparation of Libraries from the Identified Nucleic Acids

Several experimental alternatives may then be considered to clone these RNA fragments resistant to the action of RNase H:

A. A first approach consists in isolating and cloning such loops (FIG. 3).

According to this approach, one proceeds with ligation of oligonucleotides to each end by means of RNA ligase according to conditions known in the art. These oligonucleotides are then used as primers to effect RT PCR. The PCR products are cloned and screened with total complementary DNA probes corresponding to the two pathophysiological conditions of interest. Only those clones preferentially hybridizing with one of either probes contain the splice loops which are then sequenced and/or used to generate libraries.

B. The second approach (FIG. 4) consists in carrying out a reverse transcription reaction on single stranded RNA released from the heteroduplex structures by RNase H digestion, initiated by means of at least partly random primers. Thus, these may be primers with random 3' and 5' sequences, primers with random 3' ends and defined 5' sequences, or yet semi-random oligonucleotides, i.e., comprising a region of degeneration and a defined region.

According to this strategy, the primers may therefore hybridize either anywhere along the single stranded RNA, or at each succession of bases determined by the choice of semi-random primer. PCR is then run using primers corresponding to the above-described oligonucleotides in order to obtain splice loop-derived sequences.

FIG. 10 (lanes 1 to 12) presents the acrylamide gel analysis of the PCR fragments obtained in several DATAS experiments and coupled to the use of the following semi-random oligonucleotides:

```
GAGAAGCGTTATNNNNNNNAGGT    (SEQ ID NO: 1, X = T)
GAGAAGCGTTATNNNNNNNAGGA    (SEQ ID NO: 1, X = A)
GAGAAGCGTTATNNNNNNNAGGC    (SEQ ID NO: 1, X = C)
GAGAAGCGTTATNNNNNNNAGGG    (SEQ ID NO: 1, X = G)
```

Comparing these results with the complexity of the signals obtained using the same oligonucleotides, but with total cDNA as the template (lane 13), demonstrates that DATAS makes it possible to filter (profile) the information corresponding to qualitative differences.

This variant was used to clone an event corresponding to the grb2 RNA domain generated by RNase H digestion of the grb2 RNA/grb33 single stranded cDNA duplex according to the above-described protocol (example 1.1). To do so, an oligonucleotide with the sequence: GAGAAGCGTTAT-NNNNNNNNTCCC (SEQ ID NO: 2), chosen from the model GAGAAGCGTTATNNNNNNNWXYZ (where N is defined as above, W, X and Y each represent a defined fixed base, and Z designates either a defined base, or a 3'-OH group, SEQ ID NO: 3) and selected so as to amplify a fragment in the grb2 deletion, was used, allowing generation of a PCR fragment which, after cloning and sequencing, was shown to indeed be derived from the grb2 deleted domain (194-281 in grb2).

These two approaches therefore allow the production of nucleic acid compositions representative of the differential splicings in both conditions being tested, which may be used as probes or to construct, qualitative differential cDNA libraries. The capacity of DATAS technology to generated profiled cDNA libraries representative of qualitative differences is further illustrated in example 1.4 below.

1.4. Production of Profiled Libraries Representative of Human Endothelial Cells

This example was carried out using a human endothelial cell line (ECV304). The qualitative analysis of gene expression was achieved by using cystolic RNA extracted from growing cells, on the one hand, and from cells in the process of anoikis (apoptosis induced by removing the adhesion support), on the other hand.

ECV cells were grown in 199 medium supplemented with Earle salts (Life Sciences). Anoikis was induced by passage for 4 hours on polyHEMA-treated culture dishes. For RNA preparation, cells were lysed in a buffer containing Nonidet P-40. Nuclei are then eliminated by centrifugation. The cytoplasmic solution was then adjusted so as to specifically fix the RNA to the Rneasy silica matrix according to the instructions of the Quiagen company. After washing, total RNA is eluted in DEPC-treated water. Messenger RNAs are prepared from total RNAs by separation on Dynabeads oligo $(dT)_{25}$ magnetic beads (Dynal). After suspending the beads in a fixation buffer, total RNA is incubated for 5 min at room temperature. After magnetic separation and washing, the beads are taken up in elution buffer and incubated at 65° C. to release messenger RNAs.

The first DNA strand is synthesized from the messenger RNA by means of SuperScript II or ThermoScript reverse transcriptase (Life Technologies) and olido-(dT) primers. After RNase H digestion, free nucleotides are eliminated by passage through a Sephadex G50 (5 Prime-3 Prime) column. Following phenol/chloroform extraction and ethanol precipitation, samples are quantified by UV absorbance.

The required quantities of RNA and cDNA (in this case 200 ng of each) are pooled and ethanol-precipitated. The samples are taken up in a volume of 30 µl in hybridization buffer (40 mM Hepes (pH 7.2), 400 mM NaCl, 1 mM EDTA) supplemented with deionized formamide (80% (v/v), except if otherwise indicated). After denaturation for 5 min at 70° C., samples are incubated overnight at 40° C.

The streptavidin beads (Dynal) are washed then reconditioned in fixation buffer (2×=10 mM Tris-HCl (pH 7.5), 2 M NaCl, 1 mM EDTA). The hybridization samples are diluted to a volume of 200 µl with water, then adjusted to 200 µl of beads and incubated for 60 min at 30° C. After magnetic capture and washing of the beads, the latter are suspended in 150 µl of RNase H buffer then incubated for 20 min at 37° C. After magnetic capture, nonhybridized regions are released into the supernatant which is treated with Dnase, then extracted with acidic phenol/chloroform and ethanol-precipitated. Ethanol precipitations of small quantities of nucleic acids are carried out using a commercial polymer SeeDNA (Amersham Pharmacia Biotech) allowing quantitative recovery of nucleic acids from very dilute solutions (in the ng/ml range).

Synthesis of cDNA from the RNA samples derived from RNase H digestion is carried out by means of random hexanucleotides and Superscript II reverse transcriptase. The RNA is then digested with a mixture of RNase H and RNase T1. The primer, the unincorporated nucleotides and the enzymes are separated from the cDNA by means of a Glass-MAX Spin cartridge. The cDNA corresponding to splice loops is then subjected to PCR using the semi-random oligonucleotides described, hereinabove in the invention. In this case the chosen oligonucleotides are as follows:

```
GAGAAGCGTTATNNNNNNCCA    (SEQ ID NO: 4)
```

The PCR reaction is effected using Taq Polymerase for 30 cycles:

Initial denaturation: 94° C. for 1 min.
94° C. for 30 s
55° C. for 30 s
72° C. for 30 s
Final elongation: 72° C. for 5 min.

The PCR products are cloned into the pGEM-T vector (Promega) with a floating T at the 3' ends so as to simplify cloning of the fragments derived from the activity of Taq polymerase. After transformation in competent JM109 bacteria (Promega), the resulting colonies are transferred to nitrocellulose filters, and hybridized with probes derived from the products of PCR carried out on total cDNA from growing cells on the one hand and in anoikis on the other hand. The same oligonucleotides GAGAAGCGTTAT-NNNNNCCA are used for these PR reactions. In a first experimental embodiment, 34 clones preferentially hybridizing with the probe from cells in apoptosis and 13 clones preferentially hybridizing with the probe from growing cells were isolated.

Among these 13 clones, 3 clones contain the same cDNA fragment derived from the SH2 domain of the SHC protein.

This fragment has the following sequence:

(SEQ ID NO: 5)
CCACACCTGGCCAGTATGTGCTCACTGGCTTGCAGAGTGGGCAGCCAG

CCTAAGCATTTGCACTGG

The use of PCR primers flanking the SHC SH2 domain (5' oligo: GGGACCTGTTTGACATGAAGCCC (SEQ ID NO:6); 3' oligo: CAGTTTCCGCTCCACAGGTTGC (SEQ ID NO:7)) allowed characterization of the SHC SH2 domain deletion which is specifically observed in ECV cells in anoikis. With this primer pair, a single amplification product corresponding to a 382 base pair cDNA fragment which contains the intact SH2 domain is obtained from RNA from exponentially growing ECV cells. A further 287 base pair fragment is observed when the PCR is carried out with RNA from cells in anoikis. This additional fragment derives from a messenger RNA derived from the SCH messenger but with a deletion.

This deletion has the following sequence:

(SEQ ID NO: 8)
GTACGGGAGAGCAGGACCACACCTGGCCAGTATGTGCTCACTGGCTTG

CAGAGTGGGCAGCCTAAGCATTTGCTACTGGTGGACCCTGAGGGTGTG.

This deletion corresponds to bases 1198 to 1293 of the messenger open reading frame encoding the 52 kDa and 46 kDa forms of the SHC protein (Pelicci, G. et al., (1992), Cell, 70: 93-104).

Structural data on the SH2 domains together with the literature indicate that such a deletion leads to the loss of affinity for phosphotyrosines since it encompasses the amino acids involved in interactions with phosphorylated tyrosines (Waksman, G. et al., (1992), Nature, 358: 646-653). As SHC proteins are adaptors which link different partners via their SH2 and PTB domains (PhosphoTyrosine Binding domain), this deletion therefore generates a native negative dominant form of SHC which we call ΔSHC As the SH2 domains of proteins for which the genes have been sequenced are carried on two exons, it is likely that the deletion identified by DATAS corresponds to an alternative exon of the SHC gene.

The protein and nucleic acid sequences of ΔSHC are given in FIG. 17 (SEQ ID NO: 9 and 10).

As the SHC SH2 domain is involved in the transduction of numerous signals involved in cell proliferation and viability, examination of the ΔSHC sequence makes it possible to predict its negative dominant properties on the SHC protein and its capacity to interfere with various cellular signals.

The invention equally concerns this new spliced form of SHC, the protein domain corresponding to the splicing, any antibody or nucleic acid probe allowing its detection in a biological sample, and their use for diagnostic or therapeutic purposes, for example.

The invention particularly concerns any SHC variant comprising at least one deletion corresponding to bases 1198 to 1293, more particularly a deletion of sequence SEQ ID NO: 8. The invention more specifically concerns the ΔSHC variant possessing the sequence SEQ ID NO: 9, coded by the sequence SEQ ID NO: 10.

The invention therefore concerns any nucleic acid probe, oligonucleotide or antibody by which to identify the hereinabove ΔSHC variant, and/or any alteration of the SHC/ΔSHC ratio in a biological sample. This may notably be a probe or oligonucleotide complementary to all or part of the sequence SEQ ID NO: 8, or an antibody directed against the protein domain encoded by this sequence. Such probes, oligonucleotides or antibodies make it possible to detect the presence of the nonspliced form (eg., SHC) in a biological sample.

The materials may further be used in parallel with the probes, oligonucleotides and/or antibodies specific of the spliced form (eg., ΔSHC), i.e. corresponding for example to the junction region resulting from splicing (located around nucleotide 1198 in sequence SEQ ID NO: 10).

Such materials may be used for the diagnosis of diseases related to immune suppression (cancer, immunosuppressive therapy, AIDS, etc.).

The invention also concerns any screening method for molecules based on blocking (i) the spliced domain in the SHC protein (especially in order to induce a state of immune tolerance for example in autoimmune diseases or graft rejection and cancer) or (ii) the added functions acquired by the ΔSHC protein.

The invention is further directed to the therapeutic use of ΔSHC, and notably to the treatment of cancerous cells or cancers (ex vivo or in vivo) in which SHC protein hyperphosphorylation can be demonstrated, for example. In this respect, the invention therefore concerns any vector, notably a viral vector, comprising a sequence coding for ΔSHC. This vector is preferably capable of transfecting cancerous or growing cells, such as smooth muscle cells, endothelial cells (restenosis), fibroblasts (fibrosis), preferably of mammalian, notably human, origin. Viral vectors may be exemplified in particular by adenoviral, retroviral, AAV, herpes vectors, etc.

2. Differential Cloning of Alternative Splicings and Other Qualitative Modifications of RNA Using Double Stranded cDNA (FIG. 5)

Messenger RNAs corresponding to normal (mN) and pathological (mP) conditions are produced, as well as corresponding double stranded complementary DNAs (dsN and dsP) by standard molecular biology procedures. R-loop structures are then obtained by hybridizing mN with dsP and mP with dsN in a solution containing 70% formamide. Differentially spliced nucleic acid domains between conditions N and P will remain in the form of double stranded DNA. Displaced single stranded DNAs are then treated with glyoxal to avoid further displacement of the RNA strand upon removal of formamide. After removal of formamide and glyoxal and treatment with RNase H, there are obtained bee-type structures, the unpaired single stranded DNAs being representative of the bee wings and the paired double stranded domain of interest being reminiscent of the bee's body. The use of enzymes which specifically digest single stranded DNA such as nuclease S1 or mung bean nuclease allows the isolation of DNA that has remained in double stranded form, which is next cloned and sequenced. This second technique allows for direct formation of a double stranded DNA fingerprint of the domain of interest, when compared to the first procedure which yields an RNA fingerprint of this domain.

This approach was carried out on the grb2/grb33 model described above. Grb2 double stranded DNA was produced by PCR amplification of grb2 single stranded, cDNA using two nucleotide primers corresponding to the sequence (1-22) of grb2 and to the complementary sequence (618-639) of grb2. This PCR fragment was purified on an agarose gel, cleaned on an affinity column (JetQuick, Genomed) and quantified by spectrophotometry. At the same time, two synthetic RNAs corresponding to the grb2 and grb33 reading frames were produced from plasmid vectors harboring grb2 or grb33 cDNAs under the control of the T7 promoter, by means of the RiboMax kit (Promega). The RNAs were purified as instructed by the supplier and cleaned on an exclusion column (Sephadex G50, 5 prime-3 prime). 600 ng of double stranded grb2 DNA (1-639) were combined with:

1. 3 µg of grb33 RNA
2. 3 µg of grb2 RNA
3. water in three separate reactions, in the following buffer:

100 mM PIPES (pH 7.2), 35 mM NaCl, 10 mM EDTA, 70% deionized formamide (Sigma).

The samples were heated to 56° C., then cooled to 44° C. by −0.2° C. increments every 10 minutes. They are then stored at 4° C. Analysis of the agarose gel reveals the altered migration patterns of lanes 1 and 2 as compared with the control lane 3 (FIG. 11A), indicating that new complexes were formed. Samples are then treated with deionized glyoxal (Sigma) (5% v/v or 1 M) for 2 h at 12° C. The complexes are then precipitated with ethanol (0.1 M NaCl, 2 volumes of ethanol), washed with 70% ethanol, dried, then resuspended in water. They are next treated by RNase H (Life Technologies), then by an enzyme specific for single stranded DNA. Nuclease S1 and mung bean nuclease have such a property and are commercially available (Life Technologies, Amersham). Such digestions (incubations for 5 minutes in the buffers supplied with the enzymes) were analyzed on agarose gels (FIG. 11B). Significant digest products were obtained only from the complexes derived from reaction 1 (grb2/grb33) (FIG. 11B, lanes 7 and 10). These digestions appear more complete with nuclease S1 (lane 7) than with mung bean nuclease (lane 10). Thus, the band corresponding to a size slightly greater than 100 base pairs (indicated by an arrow on lane 7) was purified, cloned into the pMos-Blue vector (Amersham) and sequenced. This fragment corresponds to the 120 base pair domain of grb2 which is deleted in grb33.

This approach may now be implemented starting with a total messenger RNA population and a total double stranded cDNA population produced according to methods known to those skilled in the art. RNAs corresponding to the reference condition are hybridized with double stranded cDNAs derived from the test condition and vice versa. After application of the hereinabove protocol, the digests are loaded on agarose gels so as to isolate and purify the bands corresponding to sizes ranging from 50 to 300 base pairs. Such bands are then cloned in a vector (pMos-Blue, Amersham) to generate a library of inserts enriched in qualitative differential events.

3. Construction of Libraries Derived from Qualitative Differential Screening

The two examples described hereinabove lead to the cloning of cDNAs representative of all or part of differentially spliced sequences occurring between two given pathophysiological conditions. These cDNAs allow the construction of libraries by insertion of such cDNAs into plasmid or phage vectors. These libraries may be deposited on nitrocellulose filters or any other support material known in the art, such as chips or biochips or membranes. The aforementioned libraries may be stored in a cold place, away from light. These libraries, once deposited and fixed on support materials by conventional techniques, may be treated by compounds to eliminate the host bacteria which allowed the replication of the plasmids or phages. These libraries may also be advantageously composed of cDNA fragments corresponding to cloned cDNAs but prepared by PCR so as to deposit on the filter only those sequences derived from alternative splicing events.

One of the features as well as one of the original characteristics of qualitative differential screening is that this method advantageously leads to not only one but two differential libraries ("library pair") which represent the whole array of qualitative differences occurring between two given conditions. In particular, one of the differential splicing libraries of the invention represents the unique qualitative markers of the test physiological condition as compared to the reference physiological condition, while the other library represents the unique qualitative markers of the reference physiological condition in relation to the test physiological condition. This couple of libraries is equally termed a library pair or "differential splicing library".

As one of the benefits of qualitative differential screening is that it, makes it possible to assess the toxicity of a compound, as will be set forth in the next section, a good example of the implementation of the technology is the use of DATAS to obtain cDNA clones corresponding to sequences specific of untreated HepG2 cells, on the one hand, and ethanol-treated cells, on the other hand. The latter cells exhibit signs of cytotoxicity and DNA degradation via internucleosomal fragmentation starting from 18 hours of exposure to 1 M ethanol. In order to obtain early markers of ethanol toxicity, messenger RNAs were prepared from untreated cells and from cells treated with 0.1 M ethanol for 18 h. After execution of the DATAS variant which makes use of single stranded cDNA and RNase H, the resulting cloned cDNAs were amplified by PCR, electrophoresed on agarose gels and then transferred to a nylon filter according to techniques known to those skilled in the art. For each set of clones specific on the one hand of specific qualitative differences of the untreated state and on the other hand of sequences specific of ethanol-treated cells, two identical filter duplicates are prepared. Thus the fingerprints of each set of clones are hybridized on the one hand with a probe specific to untreated cells and on the other hand with a probe specific to cells treated with 0.1 M ethanol for 18 h.

The differential hybridization profile obtained and shown in FIG. 12 makes it possible to appreciate the quality of the subtraction afforded by the DATAS technique. Thus the clones derived from hybridization of mRNA from untreated cells (NT) with cDNA from treated cells (Tr) and which should correspond to qualitative differences specific of the untreated condition, hybridize preferentially with a probe representing the total messenger RNA population of untreated cells. Conversely, clones derived from products resistant to the action of RNase H on RNA(Tr)/cDNA(NT) heteroduplexes hybridize preferentially with a probe derived from total messenger RNAs from treated cells.

The two sets of clones specific on the one hand to the treated condition and on the other hand to the untreated condition represent an example of qualitative differential libraries characteristic of two distinct cell states.

4. Uses and Benefits of Qualitative Differential Libraries

The potential applications of the differential splicing libraries of the invention are illustrated notably in FIGS. 13 to 15. Thus, these libraries are useful for:

4.1. Evaluating the Toxicity of a Compound (FIG. 13):

In this example, the reference condition is designated A and the toxic condition is designated B. Toxicity abacus charts are obtained by treating condition A in the presence of various concentrations of a reference toxic compound, for different periods of time. For different dots of toxicity abacus charts, qualitative differential libraries are constructed (library pairs), namely in this example, restricted libraries rA/cB and rB/cA. The library pairs are advantageously deposited on a support. The support is then hybridized with probes derived from the original biological sample treated with different doses of test compounds: products X, Y and Z. The hybridization reaction is developed in order to determine the toxicity potential of the test products: in this example, product Z is highly toxic and product Y shows an intermediate profile. The feasibility of constructing toxicity abacus charts is clearly illustrated in the aforementioned example regarding the construction of qualitative differential screening libraries involving ethanol treatment and HepG2 cells.

4.2. Assessing the Potency of a Pharmaceutical Composition (FIG. 14):

In this example, a restricted library pair according to the invention is constructed starting with a pathological model B and a healthy model A (or a pathological model treated with a reference active product). The differential libraries rA/cB and rB/cA are optionally deposited on a support. This library pair is fully representative of the differences in splicing which occur between both conditions. This library pair allows the efficacy of a test compound to be assessed, i.e. to determine its capacity to generate a "healthy-like" profile (rA/cB) starting from a pathological-type profile (rB/cA). In this example, the library pair is hybridized with probes prepared from conditions A and B either treated or not by the test compound. The hybridization profile that can be obtained is shown in FIG. 14. The feasibility of this application is identical to that of the aforementioned construction of qualitative differential libraries characteristic of healthy and toxic conditions. The toxic condition is replaced by the pathological condition and one assesses the capacity, of a test compound to produce a probe hybridizing more or less preferentially with the reference or pathological conditions.

4.3. Predicting the Response of a Pathological Sample to a Treatment (FIG. 15):

In this example, a restricted library pair according to the invention is constructed starting with two pathological models, one of which is responsive to treatment with a given product (the wild type p53 gene for example): condition A; while the other being unresponsive: condition B. This library pair (rA/cB; rB/cA) is deposited on a support.

This library pair is then used to determine the sensitivity of a pathological test sample to the same product. For that purpose, this library pair is hybridized with probes derived from patients' biopsy tissues one wishes to evaluate the response to the reference treatment. The hybridization profile of a responsive biopsy sample and of an unresponsive biopsy sample is presented in FIG. 15.

4.4 Identification of Ligands for Orphan Receptors

The activation of membrane or nuclear receptors by their ligands can specifically induce regulation defects in the splicing of certain RNAs. Identification of these events by the DATAS methods of the invention provides a tool (markers, libraries, kits, etc.) by which to monitor receptor activation, which can be used to search for natural or synthetic ligands for receptors, especially orphan receptors. According to this application, markers associated with regulation defects are identified and deposited on supports. Total cellular RNA, (over)expressing the receptor under study, treated or not by different compositions and/or test compounds, is extracted and used as probe in a hybridization reaction with the supports. Detection of hybridization with some or even all of the markers deposited on the support, indicates that the receptor of interest was activated, and therefore that the corresponding composition/compound constitutes or contains the ligand of said receptor.

4.5 Identification of Targets of Therapeutic Interest:

This is accomplished by identifying genes the splicing of which is altered in a pathology or in a pathological model and more specifically by identifying the modified exons or introns. This approach should make it possible to determine the sequences which code for functional domains that are altered in pathologies or in any pathophysiological process involving the phenomena of growth, differentiation or apoptosis for example.

An example of the benefit of qualitative differential screening for identifying differentially spliced genes is provided by the application of DATAS to a model of apoptosis induction via induction of wild type p53 expression. This cellular model was established by transfecting an inducible p53 tumor suppressor gene expression system. In order to identify qualitative differences which are specifically associated with p53-induced apoptosis, DATAS was implemented starting with messenger RNAs derived from induced and non-induced cells. For these experiments 200 ng of polyA+ RNA and 200 ng of cDNA were used for heteroduplex formation. About 100 clones were obtained from each cross hybridization. Hybridization of these bacterial clones, then of the cDNA fragments they contain, with probes representative of total messenger RNAs from the original conditions allowed identification of sequences specifically expressed during the potent p53 induction which leads to cell death (FIG. 16).

These fragments derive from exon or intron sequences which modulate the quality of the message present and qualify the functional domains in which they participate or which they interrupt, as targets for treatment to induce or to inhibit cell death.

Such an approach equally leads to the construction of a library pair comprising all the differential splicing events between a non-apoptotic condition and an apoptotic condition. This library pair may be used to test the hybridizing capacity of a probe derived from another pathophysiological condition or a given treatment. The results of such a hybridization will give an indication as to the potential commitment of the gene expression program of the test condition towards apoptosis.

As is apparent from the above description, the invention is further concerned with:

- any nucleic acid probe, any oligonucleotide, any antibody which recognizes a sequence identified by the method described in the present application and characterized in that they are characteristic of a pathological condition,
- the use of information derived from applying the techniques disclosed herein for the search of organic molecules for therapeutic purposes by devising screening assays characterized in that they target differentially spliced domains occurring between a healthy and a pathological condition or else characterized in that they are based on the inhibition of functions acquired by the protein as a result of differential splicing,
- the utilization of the information derived from the methods described in the present application for gene therapy applications,
- the use of cDNAs delivered by gene therapy, wherein said cDNAs behave as antagonists or agonists of defined cell signal transduction pathways, any construction or any use of molecular libraries of alternative exons or introns for purposes of:
   commercial production of diagnostic means or reagents for research purposes
   generation or search of molecules, polypeptides, nucleic acids for therapeutical applications.
any construction or any use of all computerized virtual libraries containing an array of alternative exons or introns characterized in that said libraries allow the design of nucleic acid probes or oligonucleotide primers in order to characterize alternative splicing forms which distinguish two different pathophysiological conditions.
any pharmaceutical or diagnostic composition comprising polypeptides, sense or antisense nucleic acids or chemical compounds capable of interfering with alternative splicing products identified and cloned by the methods of the invention,
any pharmaceutical or diagnostic composition comprising polypeptides, sense or antisense nucleic acids, or chemical compounds capable of restoring a splicing pattern representative of a normal condition in contrast to an alternative splicing event inherent to a pathological condition.

5. Deregulations of RNA Splicing Mechanisms by Toxic Compounds

This example shows that differential splicing forms and/or profiles may be used as markers to monitor and/or determine the toxicity and/or the efficacy of compounds.

The effects of toxic compounds on RNA splicing regulation defects were tested as follows. HepG2 hepatocyte cells were treated with different doses of three toxic compounds (ethanol, camptothecin, PMA (phorbol 12-myristate 13-acetate)). Two cytotoxicity tests (trypan blue, MTT) were performed at different time points: 4 h and 18 h for ethanol; 4 h and 18 h for camptothecin; 18 h and 40 h for PMA.

Trypan blue is a dye that can be incorporated by living cells. Simple counting of "blue" and "white" cells under a microscope gives the percentage of living cells after treatment or the percentage of survival. The experimental points are determined in triplicate.

The MTT test is a colorimetric test measuring the capacity of living cells to convert soluble tetrazolium salts (MTT) into an insoluble formazan precipitate. These dark blue formazan crystals can be dissolved and their concentration determined by measuring absorbance at 550 nm. Thus, after overnight seeding of 24-well dishes with 150,000 cells, followed by treatment of the cells with the toxic compounds, 50 μl of MTT (Sigma) are added (at a concentration of 5 mg/ml in PBS). The formazan crystal formation reaction is carried out for 5 h in a CO2 incubator (37° C., 5% CO2, 95% humidity). After addition of 500 μl of solubilization solution (0.1 N HCl in isopropanol-Triton X-100 (10%)), the crystals are dissolved with stirring and their absorbance is measured at 550 to 660 nm. Determinations are done in triplicate with suitable controls (viability, cell death, blanks).

A test of apoptosis or programmed cell death was also performed by measuring DNA fragmentation with an anti-histone antibody and ELISA. The Cell Death ELISA Plus from Roche was used.

The results of these three tests (FIGS. 18A, B, C) indicate that the following concentrations:
   ethanol: 0.1 M
   camptothecin: 1 μg/ml
   PMA: 50 ng/ml
were well below the measured IC50 values.

HepG2 cells were thus treated with these three concentrations of these three compounds for 4 h in the case of ethanol and camptothecin and for 18 h in the case of PMA. Messenger RNAs were purified on Dynal-Oligo-(dT) beads starting from total RNAs purified with the Rneasy kit (Quiagen). cDNA was synthesized from these messenger RNAs using Superscript reverse transcriptase (Life Technologies) and random hexamers as primers These initial strands served as templates for PCR amplification reactions (94° C. 1 min, 55° C. 1 min, 72° C. 1 min, 30 cycles) by means of the following oligonucleotide primers:

```
MACH-α:
5'-TGCCCAAATCAACAAGAGC-3'    (SEQ ID NO: 11)

5'-CCCCTGACAAGCCTGAATA-3'    (SEQ ID NO: 12)
```

These primers correspond to the regions common to the different described isoforms of MACH-α (1, 2 and 3, respectively amplifying 595, 550 and 343 base pairs). MACH-α (Caspase-8) is a protease involved in programmed cell death (Boldin et al., (1996), Cell, 85: 803-815).

```
BCL-X:
5' ATGTCTCAGAGCAACCGGGAGCTG 3'    (SEQ ID NO: 13)

5' GTGGCTCCATTCACCGCGGGGCTG 3'    (SEQ ID NO: 14)
```

These primers correspond to the regions common to the different described isoforms of bcl-X (bcl-XI, bcl-Xs, BCL-Xβ) (Boise et al., (1993), Cell 74: 597-608; U72398 (Genbank)) and should amplify a single 204 base pair fragment for these three isoforms.

```
FASR:
5'-TGCCAAGAAGGGAAGGAGT-3'    (SEQ ID NO: 15)

5'-TGTCATGACTCCAGCAATAG-3'   (SEQ ID NO: 16)
```

These primers correspond to the regions common to certain FASR isoforms and should amplify a 478 base pair fragment for wild type form FasR, 452 base pairs for isoform Δ8 and 415 for isoform ΔTM.

The results presented in FIG. 19 indicate that:
Camptothecin induces a decrease in the expression of isoform MACH-α1 and an increase in isoform MACH-α3.
Camptothecin induces the appearance of a new bcl-X isoform (upper band in the doublet near 200 base pairs).
Camptothecin induces a decrease in the wild type form of the fas receptor, replaced by expression of a shorter isoform which may correspond to Fas ΔTM.
Ethanol induces the disappearance of bcl-x which is replaced by a shorter isoform.
Ethanol induces an increase in the long wild type form of the fas receptor at the expense of the shorter isoform.

These results demonstrate that treatment with low concentrations of toxic compounds can induce regulation defects in the alternative splicings of certain RNAs, and this in a specific manner. The identification of these regulation defects at the post-transcriptional level, notably by application of DATAS technology, thus constitutes a tool to predict the toxicity of molecules.

The invention claimed is:

1. A device for identifying the presence or absence of at least a first differentially spliced product of a first gene or RNA, wherein said device comprises
a solid support material and single-stranded oligonucleotides of between 5 and 100 nucleotides in length attached to said support material, wherein at least one of said oligonucleotides has a length of 25-100 nucleotides,
wherein said oligonucleotides comprise at least a first and a second oligonucleotide molecule arranged serially on the support material,
wherein said first oligonucleotide molecule comprises a first sequence that is complementary to and specific for a first exon or exon-exon or exon-intron junction region of said first gene or RNA, and wherein said first sequence corresponds to a region of variability in at least one product of said first gene or RNA due to differential splicing, and
wherein said second oligonucleotide molecule comprises a second sequence that is complementary to and specific for a second exon or exon-exon or exon-intron junction region of said first gene or RNA, and wherein said second sequence corresponds to a region of variability in at least one product of said first gene or RNA due to differential splicing,
said device allowing, when contacted with a diverse population of nucleic acid molecules prepared from a biological sample under conditions allowing hybridisation to occur, the determination of the presence or absence of said first differentially spliced product relative to at least a second differentially spliced product of said first gene or RNA.

2. The device of claim 1, wherein said first and second oligonucleotide molecules are available from a compilation of published sequences or sequence information from at least one database.

3. The device of claim 1, wherein the support material is selected from the group consisting of a filter, a membrane and a chip.

4. The device of claim 1, wherein said single-stranded oligonucleotides are RNA molecules.

5. The device of claim 1, wherein said single-stranded oligonucleotides comprise oligonucleotides of less than 50 nucleotides in length.

6. The device of claim 5, wherein said single-stranded oligonucleotides comprise oligonucleotides of 25 nucleotides in length.

7. The device of claim 1, wherein said single-stranded oligonucleotides are specific for alternative splicings representative of a cell or tissue in a given pathological condition.

8. The device of claim 7, wherein said single-stranded oligonucleotides are specific for alternative splicings representative of a tumor cell or tissue.

9. The device of claim 7, wherein said single-stranded oligonucleotides are specific for alternative splicings representative of a cell or tissue undergoing apoptosis.

10. The device of claim 7, wherein said device further comprises one or more single-stranded oligonucleotides specific for a product of said first gene or RNA expressed under normal conditions.

11. The device of claim 1, where said device is useful to evaluate the toxicity of a compound or treatment to a cell, tissue, or organism by determining the presence or absence of said first differentially spliced product in a sample treated with said compound or treatment.

12. The device of claim 1, where said device is useful to evaluate the therapeutic efficacy of a compound to a cell, tissue, or organism by determining the presence or absence of said first differentially spliced product in a sample from said cell, tissue, or organism.

13. The device of claim 1, where said device is useful to evaluate the responsiveness of a subject to a compound or treatment by determining the presence or absence of said first differentially spliced product in a sample from said subject exposed to said compound or treatment.

14. The device of claim 1, wherein said device allows the determination of the presence or absence of two or more differentially spliced products of said first gene or RNA.

15. The device of claim 1, wherein said device allows the determination of the presence or absence of one or more differentially spliced products of two or more genes or RNAs.

16. The device of claim 15, wherein said device further comprises one or more single-stranded oligonucleotides specific for a product of said two or more genes or RNAs expressed under normal conditions.

17. The device of claim 1, wherein said single-stranded oligonucleotides are DNA molecules.

18. The device of claim 1, wherein said first sequence of said first oligonucleotide molecule is complementary to and specific for said first exon-exon or exon-intron junction region of said first gene or RNA, and wherein said second sequence of said second oligonucleotide molecule is complementary to and specific for said second exon-exon or exon-intron junction region of said first gene or RNA.

19. The device of claim 1, wherein said device consists essentially of single-stranded, differentially spliced oligonucleotides.

20. The device of claim 1, wherein each of said single-stranded oligonucleotides are directly attached to said support material.

21. The device of claim 1, wherein said second sequence of said second oligonucleotide molecule is complementary to and specific for said second exon-exon or exon-intron junction region of said first gene or RNA.

22. The device of claim 1 further comprising a third oligonucleotide molecule comprising a third sequence that is complementary to and specific for a second gene or RNA, wherein said third sequence corresponds to a region of variability in at least one product of said second gene or RNA due to differential splicing, said device allowing the determination of the presence or absence of a differentially spliced product of said second gene or RNA.

23. The device of claim 1, wherein said single-stranded oligonucleotides comprise oligonucleotides of 25 to 100 nucleotides in length.

24. The device of claim 1, wherein said devices comprises at least one single-stranded oligonucleotide having a length of 25 nucleotides.

\* \* \* \* \*

SEQUENCE LISTING

<160> NUMBER OF SEQ ID NOS: 16

<210> SEQ ID NO 1
<211> LENGTH: 23
<212> TYPE: DNA
<213> ORGANISM: Artificial Sequence
<220> FEATURE:
<223> OTHER INFORMATION: Synthetic Construct
<220> FEATURE:
<221> NAME/KEY: misc_feature
<222> LOCATION: (13)..(19)
<223> OTHER INFORMATION: n= A,T,C or G
<220> FEATURE:
<221> NAME/KEY: misc_feature
<222> LOCATION: (23)..(23)
<223> OTHER INFORMATION: n= A,T,C or G

<400> SEQUENCE: 1
gagaagcgtt atnnnnnnna ggn                                           23

<210> SEQ ID NO 2
<211> LENGTH: 24
<212> TYPE: DNA
<213> ORGANISM: Artificial Sequence
<220> FEATURE:
<223> OTHER INFORMATION: Synthetic Construct
<220> FEATURE:
<221> NAME/KEY: misc_feature
<222> LOCATION: (13)..(20)
<223> OTHER INFORMATION: n= A,T,C, or G

<400> SEQUENCE: 2
gagaagcgtt atnnnnnnnn tccc                                          24

<210> SEQ ID NO 3
<211> LENGTH: 23
<212> TYPE: DNA
<213> ORGANISM: Artificial Sequence
<220> FEATURE:
<223> OTHER INFORMATION: Synthetic Construct
<220> FEATURE:
<221> NAME/KEY: misc_feature
<222> LOCATION: (13)..(23)
<223> OTHER INFORMATION: n= A,T, C, or G
<220> FEATURE:
<221> NAME/KEY: misc_feature
<222> LOCATION: (13)..(23)
<223> OTHER INFORMATION: n= A,T,C, or G

<400> SEQUENCE: 3
gagaagcgtt atnnnnnnnn nnn                                           23

<210> SEQ ID NO 4
<211> LENGTH: 20
<212> TYPE: DNA
<213> ORGANISM: Artificial Sequence
<220> FEATURE:
<223> OTHER INFORMATION: Synthetic Construct
<220> FEATURE:
<221> NAME/KEY: misc_feature
<222> LOCATION: (13)..(17)
<223> OTHER INFORMATION: n= A, T, C, or G

<400> SEQUENCE: 4
gagaagcgtt atnnnnncca                                               20

<210> SEQ ID NO 5
<211> LENGTH: 66
<212> TYPE: DNA

-continued

```
<213> ORGANISM: Artificial Sequence
<220> FEATURE:
<223> OTHER INFORMATION: Synthetic Construct

<400> SEQUENCE: 5
ccacacctgg ccagtatgtg ctcactggct tgcagagtgg gcagccagcc taagcatttg    60
cactgg                                                                66

<210> SEQ ID NO 6
<211> LENGTH: 23
<212> TYPE: DNA
<213> ORGANISM: Artificial Sequence
<220> FEATURE:
<223> OTHER INFORMATION: Synthetic Construct

<400> SEQUENCE: 6
gggacctgtt tgacatgaag ccc                                             23

<210> SEQ ID NO 7
<211> LENGTH: 22
<212> TYPE: DNA
<213> ORGANISM: Artificial Sequence
<220> FEATURE:
<223> OTHER INFORMATION: Synthetic Construct

<400> SEQUENCE: 7
cagtttccgc tccacaggtt gc                                              22

<210> SEQ ID NO 8
<211> LENGTH: 96
<212> TYPE: DNA
<213> ORGANISM: Artificial Sequence
<220> FEATURE:
<223> OTHER INFORMATION: Synthetic Construct

<400> SEQUENCE: 8
gtacgggaga gcacgaccac acctggccag tatgtgctca ctggcttgca gagtgggcag    60
cctaagcatt tgctactggt ggaccctgag ggtgtg                              96

<210> SEQ ID NO 9
<211> LENGTH: 441
<212> TYPE: PRT
<213> ORGANISM: Artificial Sequence
<220> FEATURE:
<223> OTHER INFORMATION: Synthetic construct

<400> SEQUENCE: 9
```

Met Asn Lys Leu Ser Gly Gly Gly Arg Arg Thr Arg Val Glu Gly
1               5                   10                  15

Gly Gln Leu Gly Gly Glu Glu Trp Thr Arg His Gly Ser Phe Val Asn
            20                  25                  30

Lys Pro Thr Arg Gly Trp Leu His Pro Asn Asp Lys Val Met Gly Pro
        35                  40                  45

Gly Val Ser Tyr Leu Val Arg Tyr Met Gly Cys Val Glu Val Leu Gln
    50                  55                  60

Ser Met Arg Ala Leu Asp Phe Asn Thr Arg Thr Gln Val Thr Arg Glu
65                  70                  75                  80

Ala Ile Ser Leu Val Cys Glu Ala Val Pro Gly Ala Lys Gly Ala Thr
                85                  90                  95

Arg Arg Arg Lys Pro Cys Ser Arg Pro Leu Ser Ser Ile Leu Gly Arg
            100                 105                 110

Ser Asn Leu Lys Phe Ala Gly Met Pro Ile Thr Leu Thr Val Ser Ile

```
                115                 120                 125
Ser Ser Leu Asn Leu Met Ala Ala Asp Cys Lys Gln Ile Ile Ala Asn
        130                 135                 140

His His Met Gln Ser Ile Ser Phe Ala Ser Gly Gly Asp Pro Asp Thr
145                 150                 155                 160

Ala Glu Tyr Val Ala Tyr Val Ala Lys Asp Pro Val Asn Gln Arg Ala
                165                 170                 175

Cys His Ile Leu Glu Cys Pro Glu Gly Leu Ala Gln Asp Val Ile Ser
            180                 185                 190

Thr Ile Gly Gln Ala Phe Glu Leu Arg Phe Lys Gln Tyr Leu Arg Asn
        195                 200                 205

Pro Pro Lys Leu Val Thr Pro His Asp Arg Met Ala Gly Phe Asp Gly
    210                 215                 220

Ser Ala Trp Asp Glu Glu Glu Glu Pro Pro Asp His Gln Tyr Tyr
225                 230                 235                 240

Asn Asp Phe Pro Gly Lys Glu Pro Leu Gly Gly Val Val Asp Met
                245                 250                 255

Arg Leu Arg Glu Gly Ala Ala Pro Gly Ala Ala Arg Pro Thr Ala Pro
            260                 265                 270

Asn Ala Gln Thr Pro Ser His Leu Gly Ala Thr Leu Pro Val Gly Gln
        275                 280                 285

Pro Val Gly Gly Asp Pro Glu Val Arg Lys Gln Met Pro Pro Pro
    290                 295                 300

Pro Cys Pro Gly Arg Glu Leu Phe Asp Asp Pro Ser Tyr Val Asn Val
305                 310                 315                 320

Gln Asn Leu Asp Lys Ala Arg Gln Ala Val Gly Gly Ala Gly Pro Pro
                325                 330                 335

Asn Pro Ala Ile Asn Gly Ser Ala Pro Arg Asp Leu Phe Asp Met Lys
            340                 345                 350

Pro Phe Glu Asp Ala Leu Arg Val Pro Pro Pro Gln Ser Val Ser
        355                 360                 365

Met Ala Glu Gln Leu Arg Gly Glu Pro Trp Phe His Gly Lys Leu Ser
    370                 375                 380

Arg Arg Glu Ala Glu Ala Leu Leu Asn Leu Asn Gly Asp Phe Leu Val
385                 390                 395                 400

Arg Thr Lys Asp His Arg Phe Glu Ser Val Ser His Leu Ile Ser Tyr
                405                 410                 415

His Met Asp Asn His Leu Pro Ile Ile Ser Ala Gly Ser Glu Leu Cys
            420                 425                 430

Leu Gln Gln Pro Val Glu Arg Lys Leu
        435                 440

<210> SEQ ID NO 10
<211> LENGTH: 1320
<212> TYPE: DNA
<213> ORGANISM: Artificial Sequence
<220> FEATURE:
<223> OTHER INFORMATION: Synthetic construct

<400> SEQUENCE: 10
atgaacaagc tgagtggagg cggcgggcgc aggactcggg tggaagggggg ccagcttggg      60 ggcgaggagt ggacccgcca cgggagcttt gtcaataagc ccacgcgggg ctggctgcat     120
cccaacgaca aagtcatggg acccggggtt cctacttgg ttcggtacat gggttgtgtg      180
gaggtcctcc agtcaatgcg tgccctggac ttcaacaccc ggactcaggt caccagggag     240
```

```
gccatcagtc tggtgtgtga ggctgtgccg ggtgctaagg gggcgacaag gaggagaaag      300
ccctgtagcc gcccgctcag ctctatcctg gggaggagta acctgaaatt tgctggaatg      360
ccaatcactc tcaccgtctc caccagcagc ctcaacctca tggccgcaga ctgcaaacag      420
atcatcgcca accaccacat gcaatctatc tcatttgcat ccggcgggga tccggacaca      480
gccgagtatg tcgcctatgt tgccaaagac cctgtgaatc agagagcctg ccacattctg      540
gagtgtcccg aagggcttgc ccaggatgtc atcagcacca ttggccaggc cttcgagttg      600
cgcttcaaac aatacctcag gaacccaccc aaactggtca cccctcatga caggatggct      660
ggctttgatg gctcagcatg ggatgaggag gaggaagagc cacctgacca tcagtactat      720
aatgacttcc cggggaagga acccccttg ggggggtgg tagacatgag gcttcgggaa       780
ggagccgctc cagggggctgc tcgacccact gcacccaatg cccagacccc cagccacttg     840
ggagctacat tgcctgtagg acagcctgtt gggggagatc cagaagtccg caaacagatg      900
ccacctccac caccctgtcc aggcagagag cttttttgatg atccctccta tgtcaacgtg     960
cagaacctag acaaggcccg gcaagcagtg ggtggtgctg ggccccccaa tcctgctatc     1020
aatggcagtg caccccggga cctgtttgac atgaagccct tcgaagatgc tcttcgggtg     1080
cctccacctc cccagtcggt gtccatggct gagcagctcc gaggggagcc ctggttccat     1140
gggaagctga gccggcggga ggctgaggca ctgctgcagc tcaatgggga cttcttggtt     1200
cggactaagg atcaccgctt tgaaagtgtc agtcaccta tcagctacca catggacaat      1260
cacttgccca tcatctctgc gggcagcgaa ctgtgtctac agcaacctgt ggagcggaaa     1320
```

<210> SEQ ID NO 11
<211> LENGTH: 19
<212> TYPE: DNA
<213> ORGANISM: Artificial Sequence
<220> FEATURE:
<223> OTHER INFORMATION: Synthetic construct

<400> SEQUENCE: 11
tgcccaaatc aacaagagc                                                    19

<210> SEQ ID NO 12
<211> LENGTH: 19
<212> TYPE: DNA
<213> ORGANISM: Artificial Sequence
<220> FEATURE:
<223> OTHER INFORMATION: Synthetic construct

<400> SEQUENCE: 12
cccctgacaa gcctgaata                                                    19

<210> SEQ ID NO 13
<211> LENGTH: 24
<212> TYPE: DNA
<213> ORGANISM: Artificial Sequence
<220> FEATURE:
<223> OTHER INFORMATION: Synthetic construct

<400> SEQUENCE: 13
atgtctcaga gcaaccggga gctg                                              24

<210> SEQ ID NO 14
<211> LENGTH: 24
<212> TYPE: DNA
<213> ORGANISM: Artificial Sequence
<220> FEATURE:
<223> OTHER INFORMATION: Synthetic construct

```
<400> SEQUENCE: 14
gtggctccat tcaccgcggg gctg                                          24

<210> SEQ ID NO 15
<211> LENGTH: 19
<212> TYPE: DNA
<213> ORGANISM: Artificial Sequence
<220> FEATURE:
<223> OTHER INFORMATION: Synthetic construct

<400> SEQUENCE: 15
tgccaagaag ggaaggagt                                                19

<210> SEQ ID NO 16
<211> LENGTH: 20
<212> TYPE: DNA
<213> ORGANISM: Artificial Sequence
<220> FEATURE:
<223> OTHER INFORMATION: Synthetic construct

<400> SEQUENCE: 16
tgtcatgact ccagcaatag                                               20
```